(12) United States Patent
Hatakeyama et al.

(10) Patent No.: US 10,726,967 B2
(45) Date of Patent: Jul. 28, 2020

(54) POLYMERIZABLE MONOMER, POLYMER COMPOUND, BIOLOGICAL ELECTRODE COMPOSITION, BIOLOGICAL ELECTRODE, AND METHOD FOR PRODUCING BIOLOGICAL ELECTRODE

(71) Applicant: SHIN-ETSU CHEMICAL CO., LTD., Tokyo (JP)

(72) Inventors: Jun Hatakeyama, Jyoetsu (JP); Osamu Watanabe, Jyoetsu (JP); Motoaki Iwabuchi, Jyoetsu (JP); Takayuki Fujiwara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 404 days.

(21) Appl. No.: 15/858,365

(22) Filed: Dec. 29, 2017

(65) Prior Publication Data
US 2018/0197653 A1 Jul. 12, 2018

(30) Foreign Application Priority Data

Jan. 6, 2017 (JP) .................. 2017-000962
Jul. 7, 2017 (JP) .................. 2017-134032

(51) Int. Cl.
H01B 1/24 (2006.01)
A61L 27/50 (2006.01)
(Continued)

(52) U.S. Cl.
CPC ............... *H01B 1/24* (2013.01); *A61L 27/50* (2013.01); *A61L 31/126* (2013.01); *A61N 1/00* (2013.01);
(Continued)

(58) Field of Classification Search
CPC ......... H01B 1/24; A61L 27/50; A61L 31/126; A61L 2420/02; A61N 1/00; A61N 1/0404
(Continued)

(56) References Cited

U.S. PATENT DOCUMENTS 2,995,542 A * 8/1961 Brown .................... C08F 20/58
526/243
2002/0177039 A1 11/2002 Lu et al.
2016/0155530 A1 6/2016 Someya et al.

FOREIGN PATENT DOCUMENTS

JP H05-095924 A 4/1993
JP 2003-225217 A 8/2003
(Continued)

Primary Examiner — William K Cheung
(74) Attorney, Agent, or Firm — Oliff PLC

(57) ABSTRACT

The present invention provides: a biological electrode composition formable a living body contact layer for a biological electrode which is excellent in conductivity and biocompatibility, as well as light in the weight thereof and producible at a low cost, and in addition, which does not cause a significant decrease in the conductivity thereof regardless of under a water-wet condition and a dry condition; a polymer compound which can be suitably used for the biological electrode composition; a polymerizable monomer suitable as a raw material of the polymer compound; a biological
(Continued)

electrode having a living body contact layer formed of the biological electrode composition; and a method for producing the same; and wherein, the polymerizable monomer is represented by the following general formula (1).

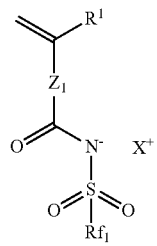

(1)

20 Claims, 2 Drawing Sheets

(51) Int. Cl.
    *A61N 1/00*     (2006.01)
    *A61L 31/12*     (2006.01)
    *A61N 1/04*     (2006.01)

(52) U.S. Cl.
    CPC ........ *A61N 1/0404* (2013.01); *A61L 2420/02* (2013.01)

(58) Field of Classification Search
    USPC .......................................... 428/457
    See application file for complete search history.

(56) References Cited

FOREIGN PATENT DOCUMENTS

| | | |
|---|---|---|
| JP | 2004-527902 A | 9/2004 |
| JP | 2015-019806 A | 2/2015 |
| JP | 2015-100673 A | 6/2015 |
| WO | 2013/039151 A1 | 3/2013 |

* cited by examiner (a)

(b)

1'  DISTANCE OF 15  1'
    CM

POLYMERIZABLE MONOMER, POLYMER COMPOUND, BIOLOGICAL ELECTRODE COMPOSITION, BIOLOGICAL ELECTRODE, AND METHOD FOR PRODUCING BIOLOGICAL ELECTRODE

TECHNICAL FIELD

The present invention relates to: a biological electrode with which body's conditions such as heart rate can be detected by an electric signal from a body's skin that is contacted thereto, as well as a method for producing the same; a biological electrode composition to be suitably used for the biological electrode; a polymer compound to be suitably used for the biological electrode composition; and a polymerizable monomer suitable for the polymer compound.

BACKGROUND ART

In recent years, with growth of IoT (Internet of Things), development of a wearable device is advancing. Typical examples thereof are a clock and an eye glass that can be connected to an internet. In a medical field and a sport field, too, a wearable device that can always monitor a body's condition is wanted; and thus, this is a growing field from now on.

In a medical field, for example, as in the case of electrocardiogram measurement with which the heart movement is detected by an electric signal, a wearable device that can monitor the condition of a body's organ by sensing a weak electric current is being studied. In electrocardiogram measurement, the measurement is carried out by attaching to a body an electrode applied with a conductive paste, but this is for only one measurement with a short measurement time. On the other hand, the wearable device for medical treatment as mentioned above aims development of a device with which a health condition can be always monitored for several weeks continuously. Accordingly, the biological electrode to be used in the wearable device for medical treatment is required not to change in conductivity even for a long period of usage as well as not to cause an allergy to a skin. In addition to these, the biological electrode is also required to be light in the weight thereof and producible at a low cost.

With regard to the wearable device for medical treatment, there are a body-attachment type and a cloth-incorporation type. With regard to the body-attachment type, a biological electrode using a water-soluble gel, which is the above-mentioned conductive paste material including water and an electrolyte, is proposed (Patent Literature 1). The water-soluble gel includes, as the electrolyte, sodium, potassium, and calcium in a water-soluble polymer to hold water therein, whereby converting a change of the ion concentration from a skin to electricity. On the other hand, with regard to the cloth-incorporated type, a method to use an electrode which has a silver paste or a conductive polymer such as PEDOT-PSS (poly-3,4-ethylenedioxythiophene-polystyrenesulfonate) incorporated into a cloth is proposed (Patent Literature 2).

However, in the case that the water-soluble gel including water and the electrolyte is used, there has been a problem that the conductivity is lost when water is lost by drying. On the other hand, in the case that a metal having a high ionization tendency such as copper is used, there is a problem of a risk to cause a skin allergy depending on a person; and also in the case that the conductive polymer such as PEDOT-PSS is used, there has been a problem of a risk to cause a skin allergy because acidity of the conductive polymer is high.

Also, use of a metal nanowire, a carbon black, a carbon nanotube, and or like as the electrode material is being studied because these materials have an excellent conductivity (Patent Literatures 3, 4, and 5). The metal nanowire has a high probability of contact among the wires themselves so that the energization can take place with a small addition amount thereof. However, because the metal nanowire is a material having a sharp and fine edge, it can cause a skin allergy. For the same reason, the carbon nanotube can irritate a living body. The carbon black is not as harmful as the carbon nanotube, but it still has a little bit of skin irritation. Therefore, even if the material itself does not induce an allergy reaction, biocompatibility can be deteriorated because of the shape and irritation property of the material; and thus, it has been difficult to satisfy both the conductivity and the biocompatibility at the same time.

It may be presumed that a metal film can function as an excellent biological electrode because it has a very high conductivity, but it is not necessarily the case. It is not a very weak electric current that is discharged from a heart beating; but those that are discharged are a sodium ion, a potassium ion, and a calcium ion. Therefore, it is necessary to convert the change in concentration of these ions to an electric current; but noble metals are poor in efficiency to convert these ions from a skin to an electric current because they are sluggish in ionization. Therefore, the biological electrodes using noble metals have high impedance so that energization with a skin is highly resisted.

On the other hand, a battery added with an ionic liquid are being studied (Patent Literature 6). The ionic liquid has characteristics of high thermal and chemical stabilities as well as excellent conductivity, and thus, the application thereof is extending to the use in battery. However, the ionic liquids such as those described in Patent Literature 6 have small molecular weights so that they are soluble in water; and thus, when the biological electrode added with the ionic liquid is used, this is extracted from a skin by a sweat. Therefore, this causes not only deterioration of conductivity but also a rough skin due to penetration of the ionic liquid into a skin.

The biological electrode cannot receive information from a body when it is departed from a skin. In addition, even a change in a contact area can cause a change in an electric amount of energization thereby causing the change in a base line of the electrocardiogram (electric signal). Therefore, in order to obtain a stable electric signal from a body, it is necessary that the biological electrode be always contacted to a skin and that the contact area thereof does not change. For this reason, it is preferable that the biological electrode has adhesiveness. In addition, the biological electrode needs to have elasticity and flexibility so as to follow the skin's expansion and contraction as well as the change in bending thereof.

PRIOR ART DOCUMENTS

Patent Documents

Patent Literature 1: International Patent Laid-Open Publication No. 2013/039151
Patent Literature 2: Japanese Patent Laid-Open Publication No. 2015-100673
Patent Literature 3: Japanese Patent Laid-Open Publication No. H05-095924

Patent Literature 4: Japanese Patent Laid-Open Publication No. 2003-225217
Patent Literature 5: Japanese Patent Laid-Open Publication No. 2015-019806
Patent Literature 6: Japanese Patent Application Publication No. 2004-527902

SUMMARY OF INVENTION

Technical Problem

The present invention was made in order to solve the problems mentioned above, and has an objective to provide: a biological electrode composition formable a living body contact layer for a biological electrode which is excellent in conductivity and biocompatibility, as well as light in the weight thereof and producible at a low cost, and in addition, which does not cause a significant decrease in the conductivity thereof regardless of under a water-wet condition and a dry condition; a polymer compound which can be suitably used for the biological electrode composition; a polymerizable monomer suitable as a raw material of the polymer compound; a biological electrode having a living body contact layer formed of the biological electrode composition; and a method for producing the same.

Solution to Problem

In order to solve the problems mentioned above, the present invention provides a polymerizable monomer represented by following general formula (1),

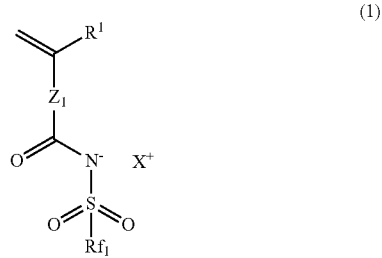

(1)

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of $-C(=O)-O-R^2-$; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

The polymerizable monomer as mentioned above can be a suitable raw material for the polymer compound to be used for the biological electrode composition formable the living body contact layer for the biological electrode which is excellent in conductivity and biocompatibility, as well as light in the weight thereof and producible at a low cost, and in addition, which does not cause a significant decrease in the conductivity thereof regardless of under a water-wet condition and a dry condition.

In addition, the present invention provides a polymer compound having a repeating unit represented by following general formula (2) and a weight average molecular weight of 500 or more,

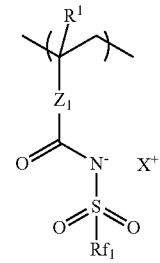

(2)

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of $-C(=O)-O-R^2-$; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

The polymer compound as mentioned above can give the biological electrode composition formable the living body contact layer for the biological electrode which is excellent in conductivity and biocompatibility, as well as light in the weight thereof and producible at a low cost, and in addition, which does not cause a significant decrease in the conductivity thereof regardless of under a water-wet condition and a dry condition.

In addition, the present invention provides a biological electrode composition comprising a polymer compound having both an ionic repeating unit "a" and a (meth)acrylate repeating unit "b", wherein the ionic repeating unit "a" is a repeating unit having a partial structure of a sodium salt, a potassium salt, or an ammonium salt, as represented by following general formula (3), and the (meth)acrylate repeating unit "b" is a repeating unit represented by following general formula (4),

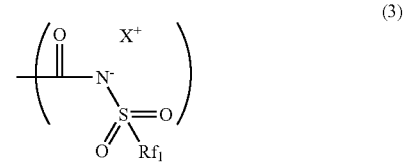

(3)

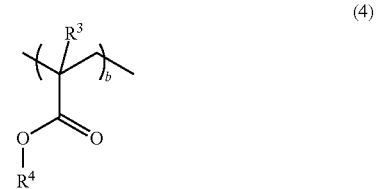

(4)

and wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^3$ represents a hydrogen atom or a methyl group; $R^4$ represents a linear, a branched, or a cyclic alkyl group having 1 to 39 carbon atoms, or a linear, a branched, or a cyclic alkenyl group having 2 to 30 carbon atoms, or a linear, a branched, or a cyclic alkynyl group having 2 to 30 carbon atoms, or a phenyl group, or a naphthyl group, and wherein, when $R^4$ is the alkyl group, the alkenyl group, or the alkynyl group, $R^4$ may contain a hydroxy group, an ether group, an ester group, or an aromatic group therein; and $0<a<1.0$, $0<b<1.0$, and $0<a+b\leq1.0$.

The biological electrode composition as mentioned above can be a suitable biological electrode composition formable the living body contact layer for the biological electrode which is excellent in conductivity and biocompatibility, as well as light in the weight thereof and producible at a low cost, and in addition, which does not cause a significant decrease in the conductivity thereof regardless of under a water-wet condition and a dry condition.

At this time, it is preferable that the repeating unit "a" be a repeating unit a1 represented by following general formula (2'),

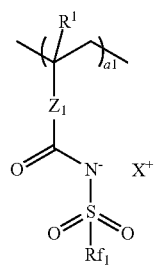

wherein, $Rf_1$ and $X^+$ represent the same groups as those mentioned before; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein; and $0<a1<1.0$.

When the repeating unit "a" is the repeating unit a1 as mentioned above, the effects of the present invention can be enhanced furthermore.

At this time, it is preferable that the polymer compound be a copolymerized polymer compound further having, in addition to the repeating unit "a" and the repeating unit "b", any one or both of a repeating unit "c" having a fluorine atom or a silicon atom and a repeating unit "d" having one or more groups selected from a hydroxy group, a carboxyl group, an oxirane group, and an oxetane group.

When the repeating unit "c" is copolymerized thereto, a water-repelling property can be obtained so that the change in conductivity due to sweat and washing can be avoided. Also, when the repeating unit "d" is copolymerized thereto, the copolymer thus obtained can have a crosslinking property so that peeling-off from a conductive substrate can be avoided.

At this time, it is preferable that the biological electrode composition further contain a carbon material, an ITO particle, or a particle coated with a metal selected from silver, gold, platinum, copper, and nickel.

The biological electrode composition as mentioned above can form the living body contact layer which has a further enhanced conductivity.

At this time, it is preferable that the carbon material be any one or both of a carbon black and a carbon nanotube.

In the biological electrode composition of the present invention, the carbon material as mentioned above can be used especially suitably.

In addition, the present invention provides a biological electrode, which is a biological electrode having a conductive substrate and a living body contact layer formed on the conductive substrate, wherein the living body contact layer is a cured product of the biological electrode composition.

The biological electrode as mentioned above is excellent in conductivity and biocompatibility, as well as light in the weight thereof and producible at a low cost, and can be a biological electrode formed with the living body contact layer for the biological electrode which does not cause a significant decrease in the conductivity thereof regardless of under a water-wet condition and a dry condition.

At this time, it is preferable that the conductive substrate contains one or more substances selected from gold, silver, silver chloride, platinum, aluminum, magnesium, tin, tungsten, iron, copper, nickel, stainless steel, chromium, titanium, and carbon.

In the biological electrode of the present invention, the conductive substrate as mentioned above can be used especially suitably.

In addition, the present invention provides a method for producing a biological electrode, which is a method for producing a biological electrode having a conductive substrate and a living body contact layer formed on the conductive substrate, wherein the method comprises application of the biological electrode composition on the conductive substrate followed by curing the composition to form the living body contact layer.

According to the method for producing the biological electrode as mentioned above, the biological electrode formed with the living body contact layer which is excellent in conductivity and biocompatibility, as well as light in the weight thereof, and in addition, which does not cause a significant decrease in the conductivity thereof regardless of under a water-wet condition and a dry condition can be produced at a low cost.

At this time, it is preferable to use the conductive substrate containing one or more substances selected from gold, silver, silver chloride, platinum, aluminum, magnesium, tin, tungsten, iron, copper, nickel, stainless steel, chromium, titanium, and carbon.

In the method for producing the biological electrode of the present invention, the conductive substrate as mentioned above can be used especially suitably.

Advantageous Effects of Invention

As mentioned above, the present invention can provide: a biological electrode composition formable a living body contact layer which can efficiently transmit an electric signal from a skin to a device (namely, this is excellent in the conductivity), which hardly causes an allergy even if it is attached to a skin for a long period of time (namely, this is excellent in the biocompatibility), which is light in the weight thereof and producible at a low cost, and which does not cause a decrease in the conductivity thereof regardless of under a water-wet condition and a dry condition; a polymer compound which can be suitably used for the biological electrode composition like this; and a polymerizable monomer which is suitable as a raw material of the polymer compound like this. In addition, in the biological electrode composition of the present invention, when a carbon material, a metal-coated particle, or an ITO particle is added thereto, the conductivity thereof can be further enhanced;

and when a polymer compound having adhesiveness and elasticity is combined therewith, a biological electrode having especially high adhesiveness and elasticity can be produced. Accordingly, the biological electrode formed with the living body contact layer by using the biological electrode composition of the present invention as mentioned above is especially suitable as a biological electrode to be used for a wearable device for medical treatment. In addition, according to the method for producing the biological electrode of the present invention, the biological electrode as mentioned above can be easily produced at a low cost.

DESCRIPTION OF EMBODIMENTS

Figure 1:
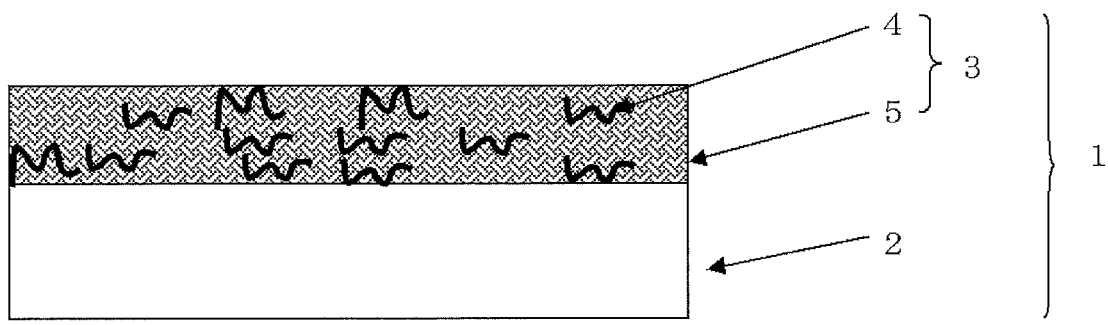
FIG. 1 is a rough cross section view illustrating one example of the biological electrode of the present invention.

As mentioned above, there have been wanted: a biological electrode composition formable a living body contact layer for a biological electrode which is excellent in conductivity and biocompatibility, as well as light in the weight thereof and producible at a low cost, and in addition, which does not cause a significant decrease in the conductivity thereof regardless of under a water-wet condition and a dry condition; a polymer compound which can be suitably used for the biological electrode composition; a polymerizable monomer suitable as a raw material of the polymer compound; a biological electrode having a living body contact layer formed of the biological electrode composition; and a method for producing the same.

Inventors of the present invention noted alkaline metal salts such as sodium salts and potassium salts of a fluorosulfonic acid and a bisfluorosulfonyl imidic acid, as well as ammonium salts thereof, all having been generally known as an ionic liquid to be blended into a biological electrode composition for forming a living body contact layer for a biological electrode. However, these salts generally have a high hydration property, so that in the biological electrode formed with a living body contact layer by using the biological electrode composition added with these salts, the salts are extracted by sweat or washing; and thus, there has been a problem of decrease in the conductivity thereof. In addition, the imidic acid having a fluoroalkyl group in each side of the bissulfonyl imidic acid has a higher acidity than an α-fluorosulfonic acid; and thus, even if this is neutralized with sodium or potassium, they have a high irritation property to a skin. Moreover, an ionic liquid having a small molecular weight can pass through a skin when it contacts to a skin thereby increasing a risk of causing a skin allergy.

On the other hand, because a polymer-type ionic compound does not pass through a skin, a risk to cause a skin allergy due to this compound decreases. With regard to the polymer-type fluorosulfonic acid, a copolymer of tetrafluoroethylene and perfluoro [2-(fluorosulfonylethoxy) propyl vinyl ether] (registered trade name of Nafion) has been known. This copolymer has high proton mobility, and is being studied for a fuel cell. However, because Nafion has a very high acidity, even its neutralized salts with sodium, potassium, and ammonium have a high skin irritation property. Further, Nafion lacks an adhesive function, so that there is a problem in this point, too, when it is applied to the biological electrode.

There is a proposal of an antibacterial composition using a polymer copolymerized with a methide acid (Japanese Patent Laid-Open Publication No. 2012-92088). However, similarly to Nafion, the methide acid also has such a high acidity so as to be able to sterilize bacteria; and thus, this also has a problem when it is used for the biological electrode. On the other hand, the biological electrode using sodium salt or the like of polymethacrylic acid has a problem of a low conductivity. In order to obtain a high ionic conductivity, a neutralized salt of the salt having a high acidity is necessary. Therefore, development of a material satisfying both the acidity and the biocompatibility is necessary.

Accordingly, inventors of the present invention carried out an extensive investigation on the problems as mentioned above, and as a result, they developed an acid having a lower acidity than the imidic acid having a fluoroalkyl group in both sides of the bissulfonyl imide. Namely, the inventors noted a sulfonamide having a nitrogen atom sandwiched between a fluoroalkyl sulfonyl group on one side and a carbonyl group on another side. Because the sulfonamide like this has an appropriate acidity, both the high conductivity and the biological compatibility can be satisfied when this is used as a neutralized salt. In addition, when the sulfonamide has a polymerizable double bond, it can be polymerized to a polymer. Accordingly, the inventors presumed that when the sulfonamide is polymerized, and then an alkaline metal salt or an ammonium salt of this polymerized sulfonamide is used, it may not dissolve into water thereby giving the biological electrode without decrease in the conductivity by extraction with sweat or without a risk to cause a rough skin. In fact, it became apparent that the biological electrode using a polymer obtained by polymerizing a synthesized monomer of an alkaline metal salt or an ammonium salt of the sulfonamide having a polymerizable double bond could satisfy both the conductivity and the biological compatibility, and that the conductivity did not change regardless of under a water-wet condition and a dry condition. Further, when a polymer obtained by copolymerizing, in addition to the monomer mentioned above, a copolymerizable monomer giving a repeating unit capable of giving adhesiveness was used, it was found that the biological electrode always adhering to a skin thereby stably receiving an electric signal for a long period of time could be obtained, so that the present invention could be completed.

Namely, the present invention is a polymerizable monomer represented by the following general formula (1),

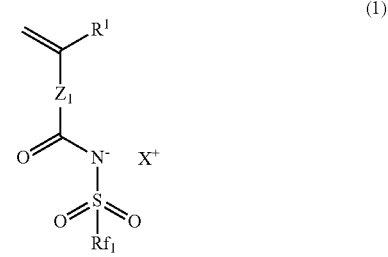

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

Hereunder, the present invention will be explained in detail; but the present invention is not limited to the description below.

<Polymerizable Monomer>

The present invention provides a novel polymerizable monomer represented by the following general formula (1).

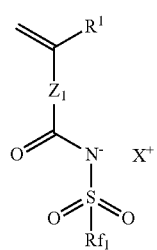

(1)

wherein, $Rf_1$ represents a linear or a branched alkyl group having 1 to 4 carbon atoms and includes one or more fluorine atoms; represents any of a sodium ion, a potassium ion, and an ammonium ion; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

Specific example of the polymerizable monomer of the sulfonamide represented by the general formula (1) includes the following monomers,

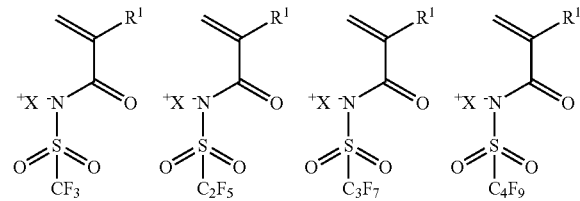

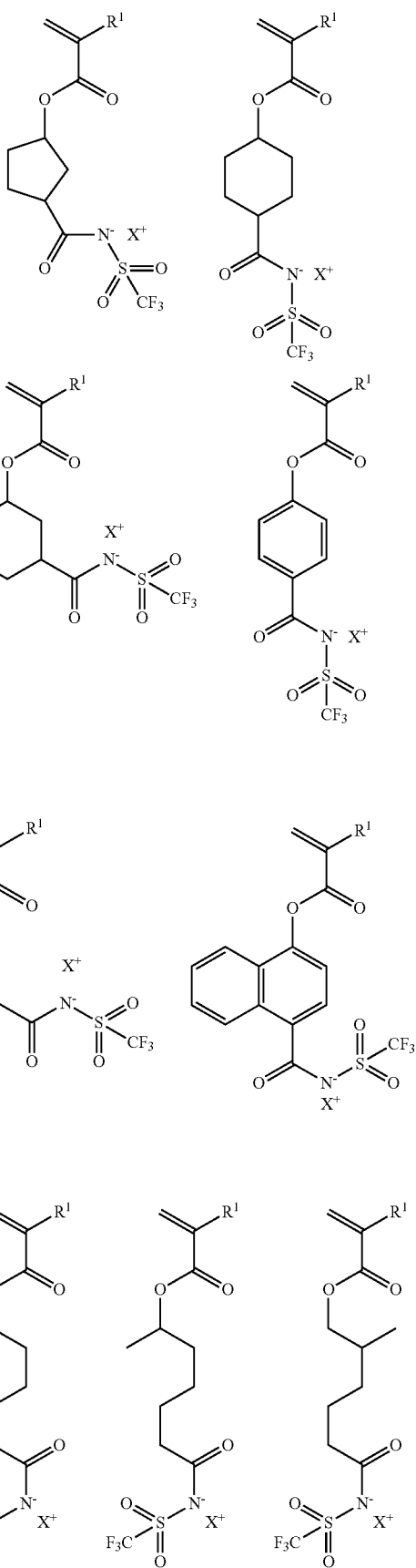

-continued
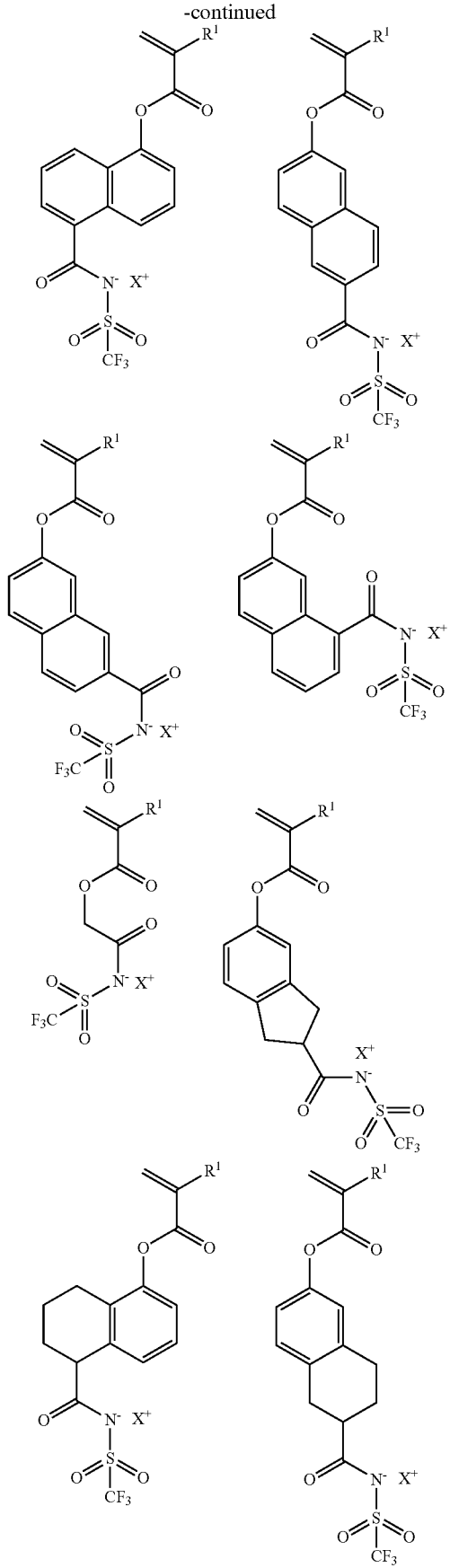
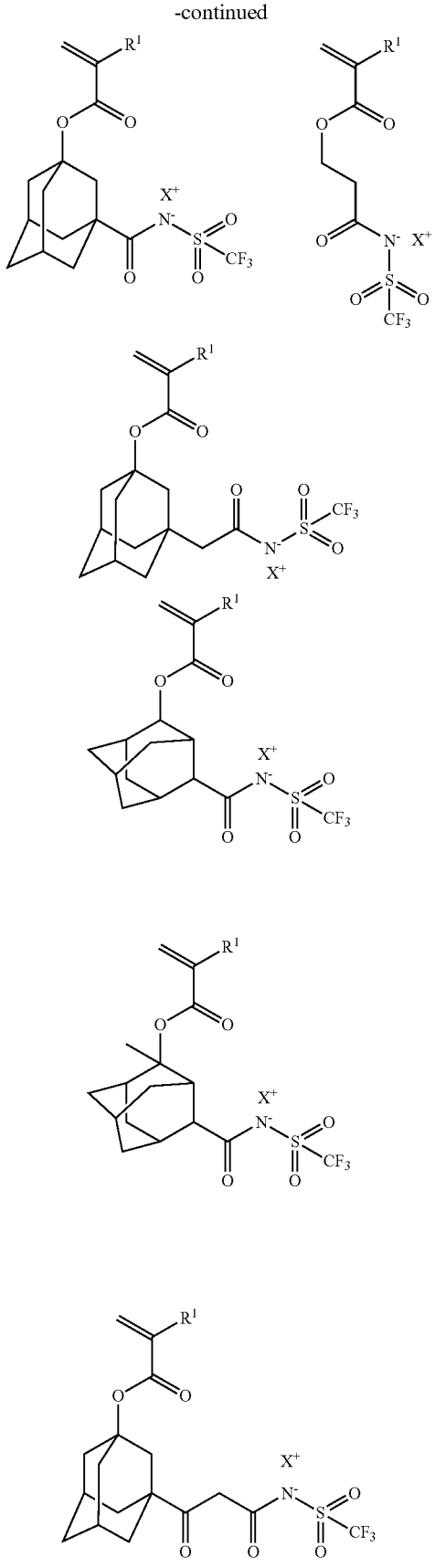

-continued
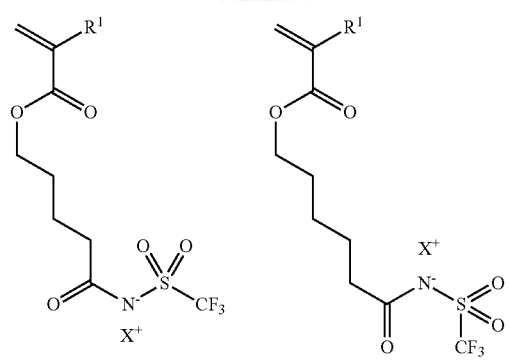
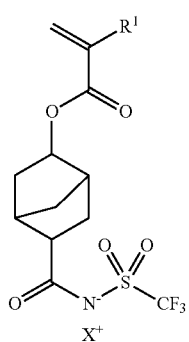
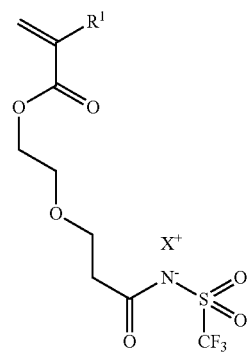
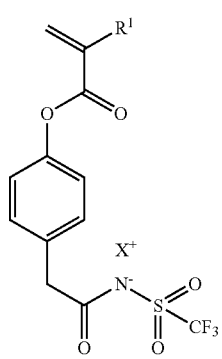
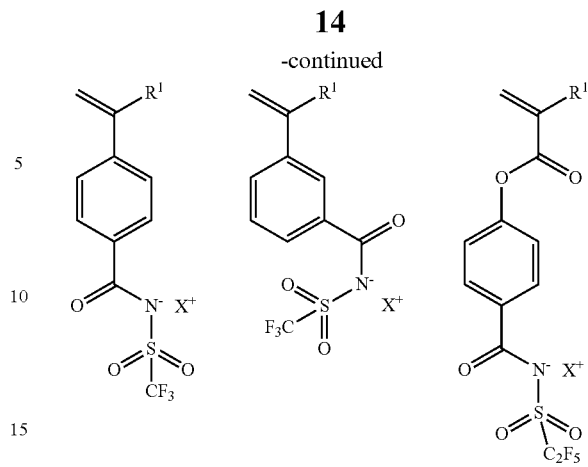
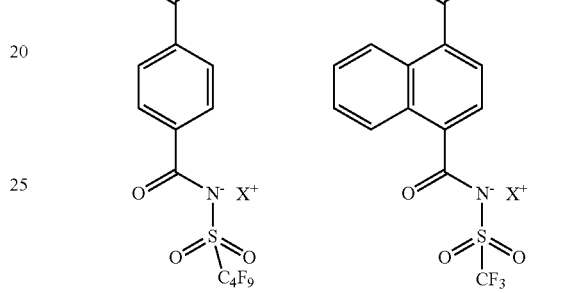
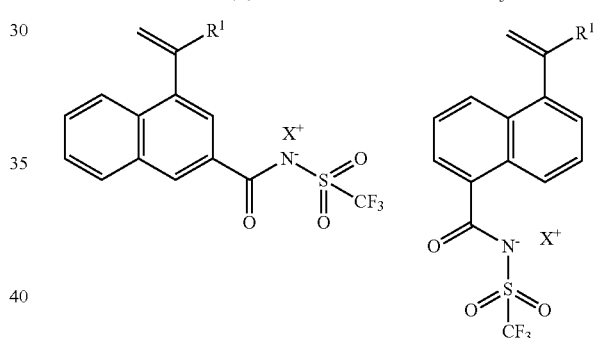
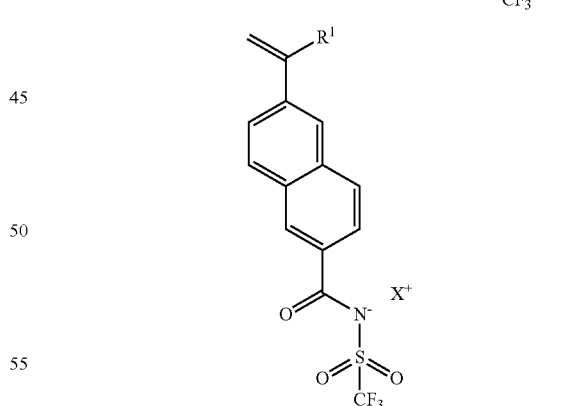
wherein, $R^1$ and $X^+$ represent the same groups as those described before.
In the present invention, $X^+$ in the general formula (1) is any of a sodium ion, a potassium ion, and an ammonium ion. With regard to the example when $X^+$ is an ammonium ion, the monomer represented by the following general formula (5) may be mentioned,

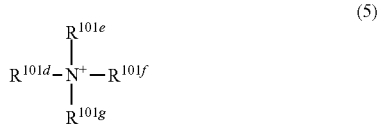

(5)

wherein, each of $R^{101d}$, $R^{101e}$, $R^{101f}$, and $R^{101g}$ represents a hydrogen atom, or a linear, a branched, or a cyclic, alkyl, alkenyl, oxoalkyl, or oxoalkenyl group each having 1 to 12 carbon atoms, or an aryl group having 6 to 20 carbon atoms, or an aralkyl or an aryloxoalkyl group each having 7 to 12 carbon atoms, and wherein, a part or all of hydrogen atoms in these groups may be substituted by an alkoxy group; $R^{101d}$ and $R^{101e}$, as well as $R^{101d}$ and $R^{101e}$ and $R^{101f}$ may be bonded to form a ring together with the nitrogen atom to which these groups are bonded, and when the ring is formed, $R^{101d}$ and $R^{101e}$, as well as $R^{101d}$ and $R^{101e}$ and $R^{101f}$ forms an alkylene group having 3 to 10 carbon atoms or a heterocyclic aromatic ring incorporated therein with the nitrogen atom shown in the formula.

With regard to the synthesis method of the sodium salt, the potassium salt, or the ammonium salt of the polymerizable monomer represented by the general formula (1), the method may be mentioned, for example, in which an acid chloride having a polymerizable group is caused to react with a fluoroalkane sulfonamide in the presence of a base in an organic solvent thereby obtaining the said monomer, as illustrated in the following reaction formula. Meanwhile, the present invention is not limited to this,

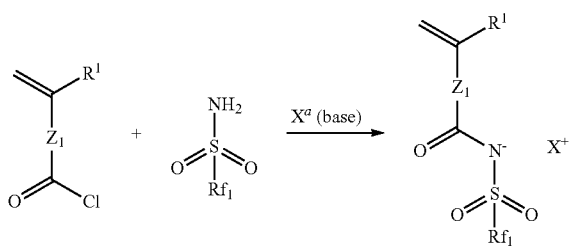

and wherein, $R^1$, $Z_1$, $Rf_1$, and $X^+$ represent the same groups as those described before; and $X^a$ represents a base.

In the reaction formula mentioned above, the use amount of the acid chloride is preferably 0.5 to 3 moles, while more preferably 0.8 to 1.5 moles, relative to 1 mole of the fluoroalkane sulfonamide. The acid chloride can be synthesized from a corresponding carboxylic acid by a heretofore known method. With regard to the method like this, for example, a method in which oxaryl chloride or thionyl chloride is caused to act to the carboxylic acid in an organic solvent may be mentioned.

With regard to the fluoroalkane sulfonamide, a commercially available compound may be used; or alternatively, it may be synthesized by a reaction of ammonia with a corresponding fluoroalkane sulfonyl halide or fluoroalkane sulfonic anhydride.

The base $X^a$ is not particularly restricted, wherein illustrative example thereof includes sodium carbonate, sodium hydroxide, sodium hydride, potassium carbonate, potassium hydroxide, potassium hydride, trimethyl amine, triethyl amine, diisopropyl ethyl amine, pyridine, lutidine, collidine, and N,N-dimethylaminopyridine. Use amount of the base is preferably 1.0 to 4.0 moles relative to 1 mole of the fluoroalkane sulfonamide. The respective monomers may be synthesized by using the foregoing sodium-based bases when $X^+$ is a sodium ion, the foregoing potassium-based bases when $X^+$ is a potassium ion, and the corresponding tertiary amines when $X^+$ is a tertiary ammonium ion. When $X^+$ is an ammonium ion, the synthesis may be done by cation-exchange with a monomer of a sodium ion or of a potassium ion.

Illustrative example of the reaction solvent to be used includes acetonitrile, methylene chloride, dichloroethane, acetone, 2-butanone, ethyl acetate, dimethylformamide, N-methylpyrrolidone, tetrahydrofuran, 1,4-dioxane, toluene, xylene, hexane, heptane, and chlorobenzene. They may be used singly or as a mixture of them. Alternatively, the reaction may be carried out without solvent. The reaction temperature is −10° C. to about a boiling point of the solvent, while preferably 0° C. to a boiling point of the solvent. The reaction time is usually about 30 minutes to 40 hours.

In the above reaction formula, a similar reaction may also be carried out by using an acid anhydride in place of the acid chloride; and alternatively, a similar reaction may also be carried out by using, in place of the fluoroalkane sulfonamide, a corresponding sulfonamide salt, such as for example, a potassium salt of trifluoromethane sulfonamide.

As mentioned before, the polymerizable monomer of the present invention can be a suitable raw material of the polymer compound to be used for the biological electrode composition formable the living body contact layer for the biological electrode which can efficiently transmit an electric signal from a skin to a device (namely, this is excellent in the conductivity), which hardly causes an allergy even if it is attached to a skin for a long period of time (namely, this is excellent in the biocompatibility), which is light in the weight thereof and producible at a low cost, and which does not cause a significant decrease in the conductivity thereof regardless of under a water-wet condition and a dry condition.

<Polymer Compound Having Repeating Unit Represented by the General Formula (2)>

In addition, the present invention provides a novel polymer compound having a repeating unit represented by the following general formula (2) and a weight average molecular weight of 500 or more,

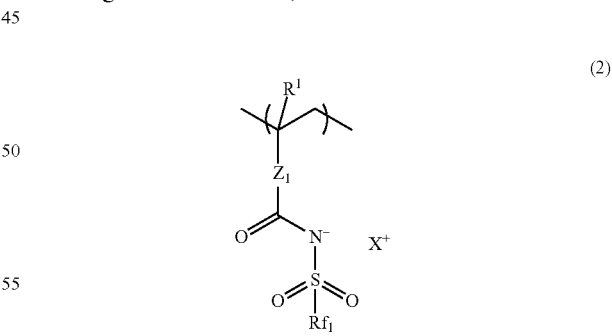

(2)

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

The repeating unit represented by the general formula (2) may be obtained, for example, by polymerizing the polymerizable monomer represented by the general formula (1). With regard to the specific example of the repeating unit represented by the general formula (2), polymers obtained by polymerizing those exemplified as the polymerizable monomer represented by the general formula (1) may be mentioned.

The molecular weight of the polymer compound having the repeating unit represented by the general formula (2) needs to be, as the weight average molecular weight, 500 or more, preferably 1,000 or more and 1,000,000 or less, while more preferably 2,000 or more and 500,000 or less.

As mentioned above, the polymer compound of the present invention can give the biological electrode composition formable the living body contact layer for the biological electrode which can efficiently transmit an electric signal from a skin to a device (namely, this is excellent in the conductivity), which hardly causes an allergy even if it is attached to a skin for a long period of time (namely, this is excellent in the biocompatibility), which is light in the weight thereof and producible at a low cost, and which does not cause a significant decrease in the conductivity thereof regardless of under a water-wet condition and a dry condition.

<Biological Electrode Composition>

The biological electrode composition of the present invention contains, as a polymer-type ionic material having an adhesive function, a polymer compound having both an ionic repeating unit "a" and a (meth)acrylate repeating unit "b" (hereinafter, this polymer compound is sometimes referred to as simply "polymer compound"). Hereunder, each component will be explained in more detail.

[Polymer Compound]

The polymer compound in the biological electrode composition of the present invention is a polymer-type salt that is blended thereto as a conductive material, wherein this polymer compound has both the ionic repeating unit "a" and the (meth)acrylate repeating unit "b".

The ionic repeating unit "a" is a repeating unit having a partial structure of a sodium salt, a potassium salt, or an ammonium salt, as represented by the following general formula (3),

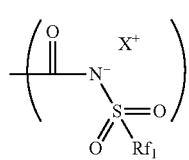

(3)

wherein, $Rf_1$ represents a linear or a branched alkyl group having 1 to 4 carbon atoms and includes one or more fluorine atoms; represents any of a sodium ion, a potassium ion, and an ammonium ion; and $0<a<1.0$.

It is preferable that the repeating unit "a" be a repeating unit a1 represented by following general formula (2'),

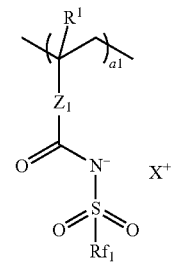

(2')

wherein, $Rf_1$ and $X^+$ represent the same groups as those mentioned before; $R^1$ represents a hydrogen atom or a methyl group; $Z_1$ represents a single bond, an arylene group having 6 to 12 carbon atoms, or a group of —C(=O)—O—R²—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein; and $0<a1<1.0$.

With regard to the monomer to obtain the repeating unit a1 represented by the general formula (2'), the same monomers as those exemplified as the polymerizable monomer represented by the general formula (1) may be mentioned.

The polymer compound in the biological electrode composition of the present invention has, in addition to the repeating unit "a", the (meth)acrylate repeating unit "b" represented by the following general formula (4) as the repeating unit giving an adhesive function,

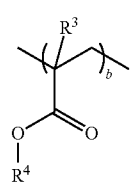

(4)

wherein, $R^3$ represents a hydrogen atom or a methyl group; $R^4$ represents a linear, a branched, or a cyclic alkyl group having 1 to 39 carbon atoms, or a linear, a branched, or a cyclic alkenyl group having 2 to 30 carbon atoms, or a linear, a branched, or a cyclic alkynyl group having 2 to 30 carbon atoms, or a phenyl group, or a naphthyl group, and wherein, when $R^4$ is the alkyl group, the alkenyl group, or the alkynyl group, $R^4$ may contain a hydroxy group, an ether group, an ester group, or an aromatic group therein; and $0<b<1.0$.

Meanwhile, the ratio of the repeating unit "a" and the repeating unit "b" is $0<a<1.0$, $0<b<1.0$, and $0<a+b\leq1.0$.

With regard to the monomer to obtain the repeating unit "b", the following monomers may be mentioned as the specific examples thereof.

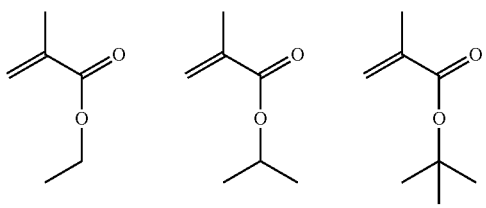

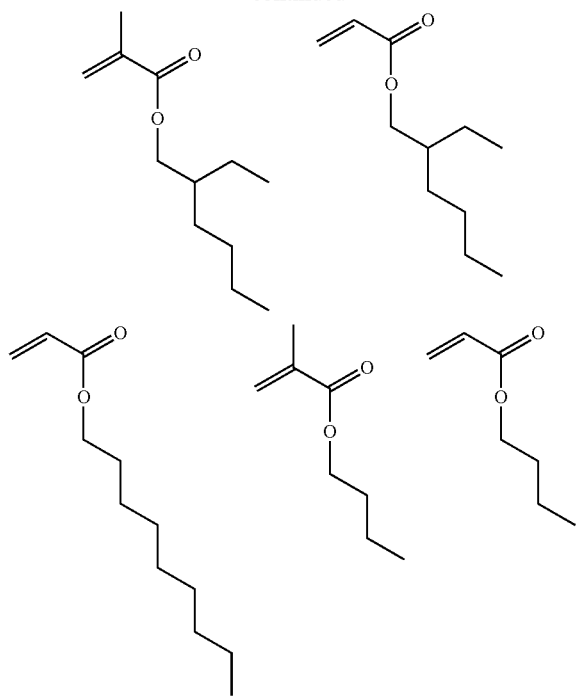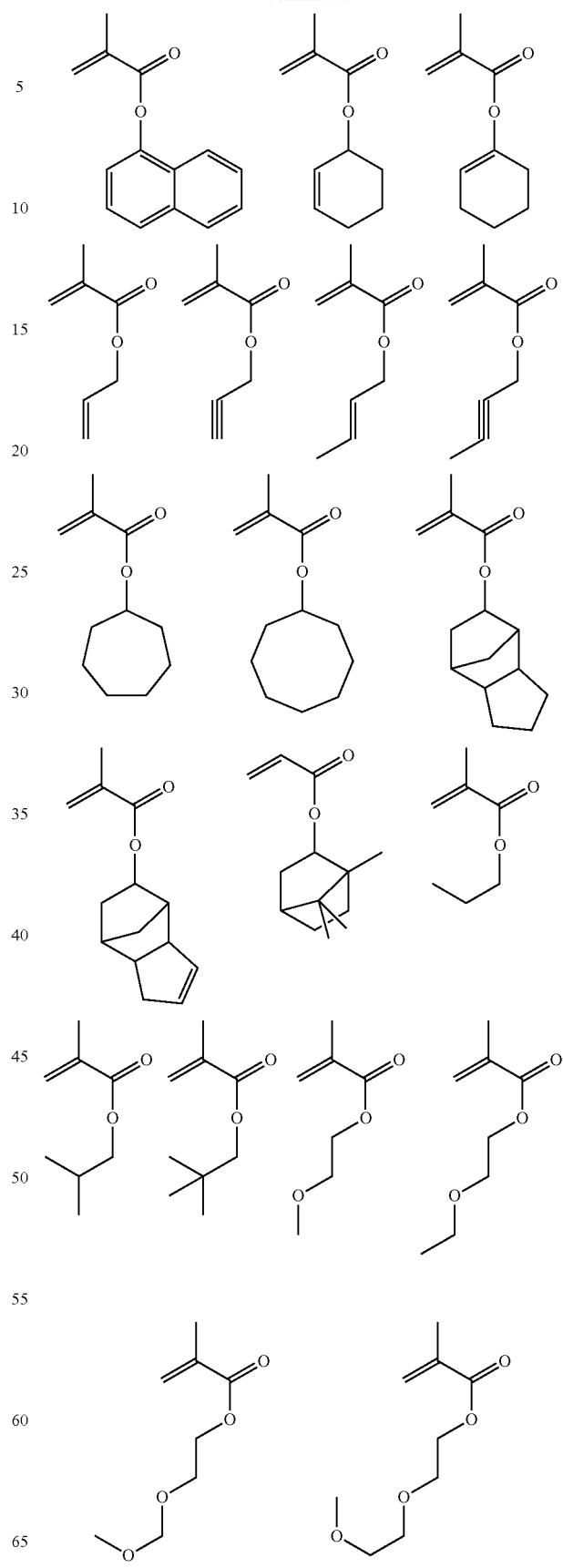

-continued
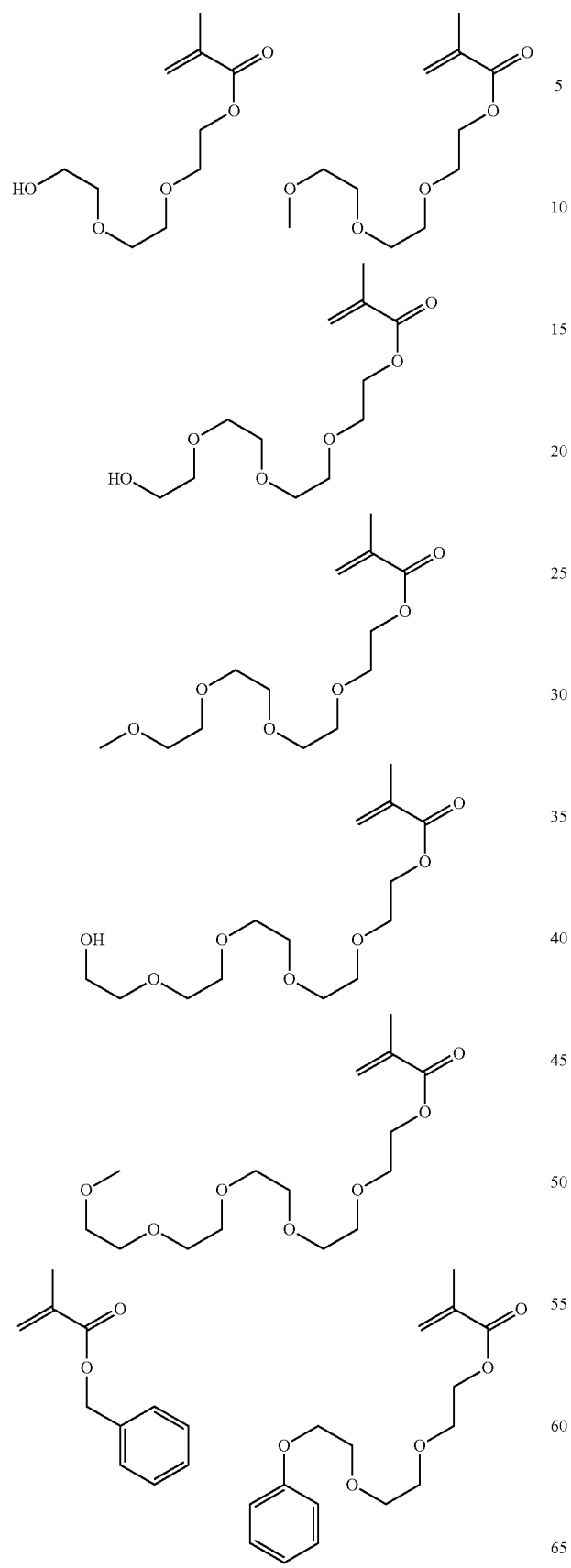
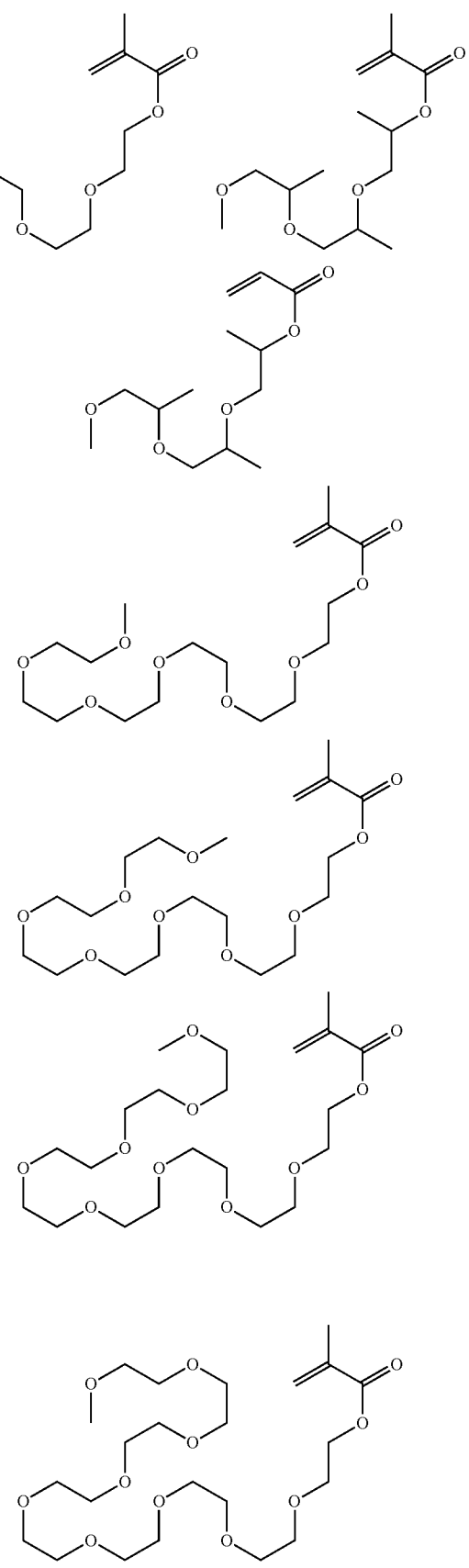

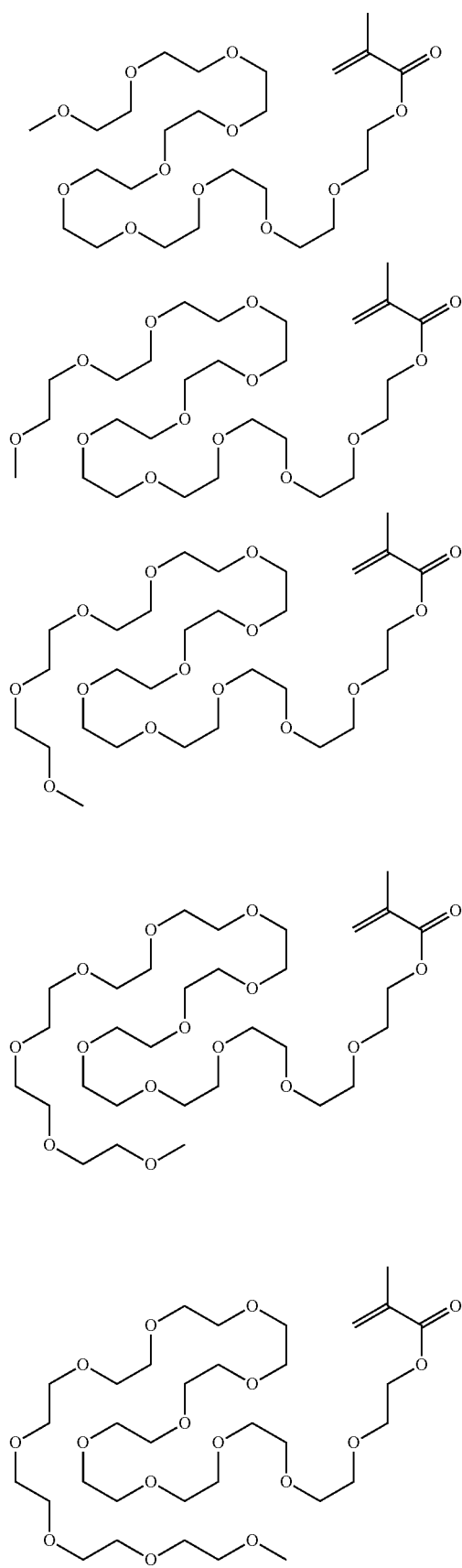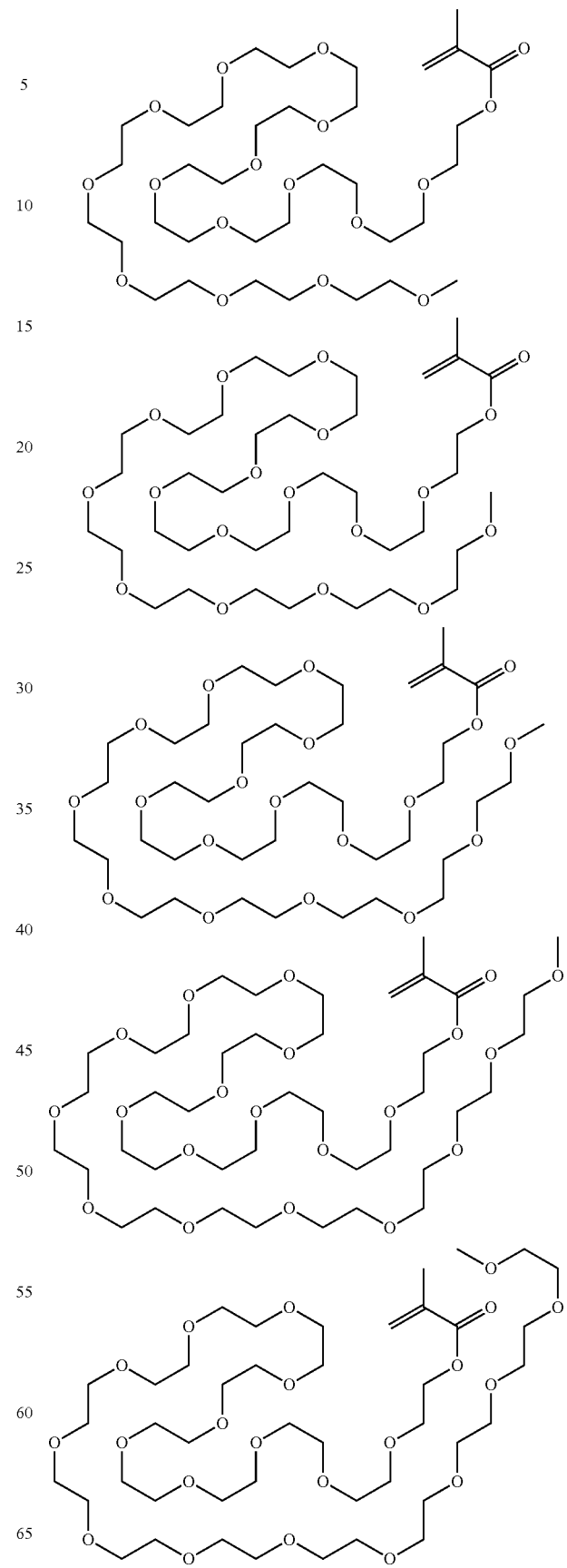

25
-continued
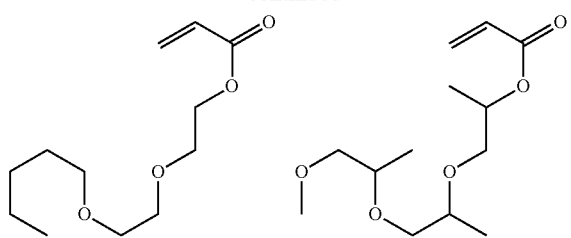
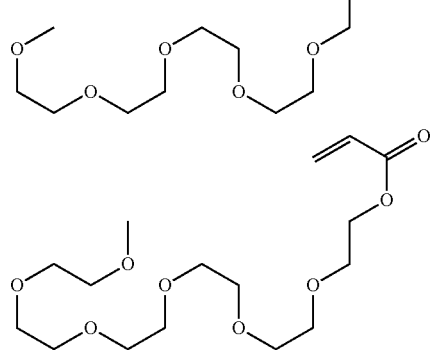
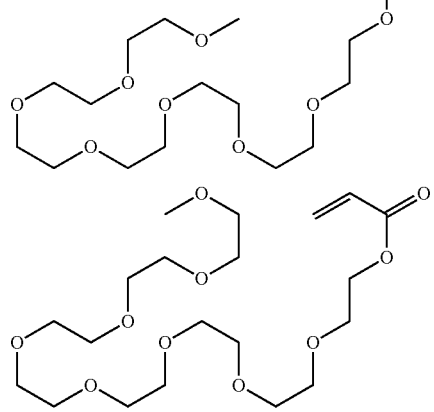
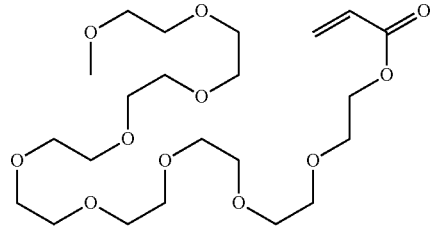
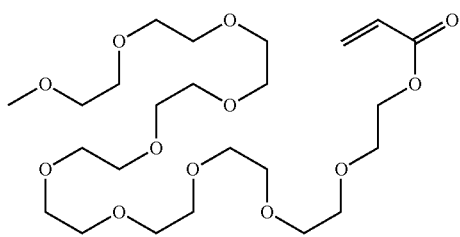
26
-continued
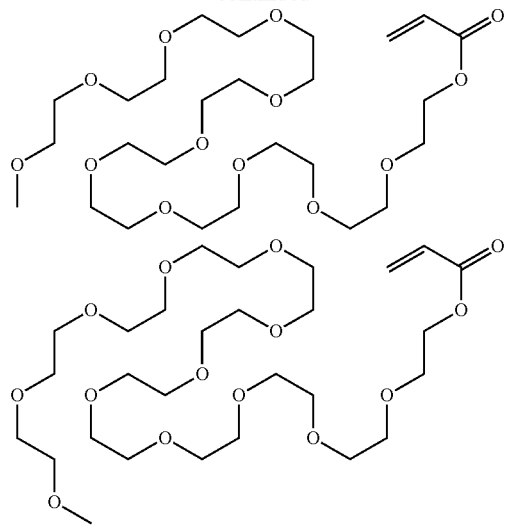
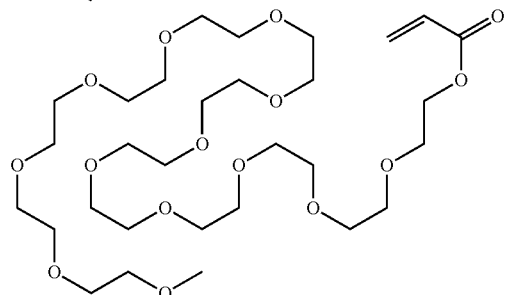
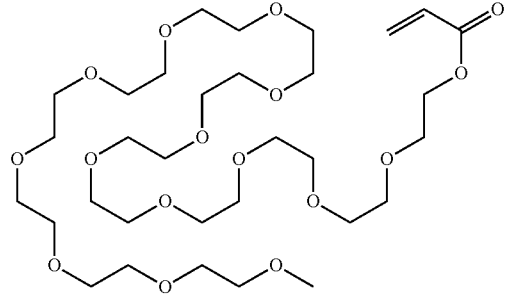
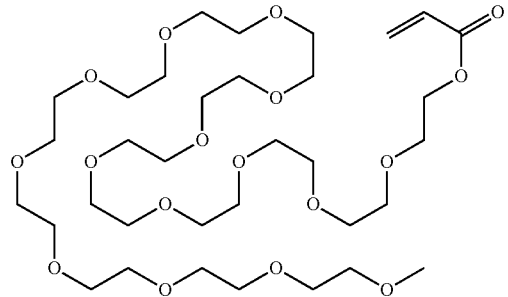
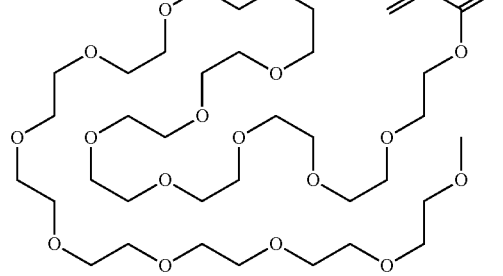

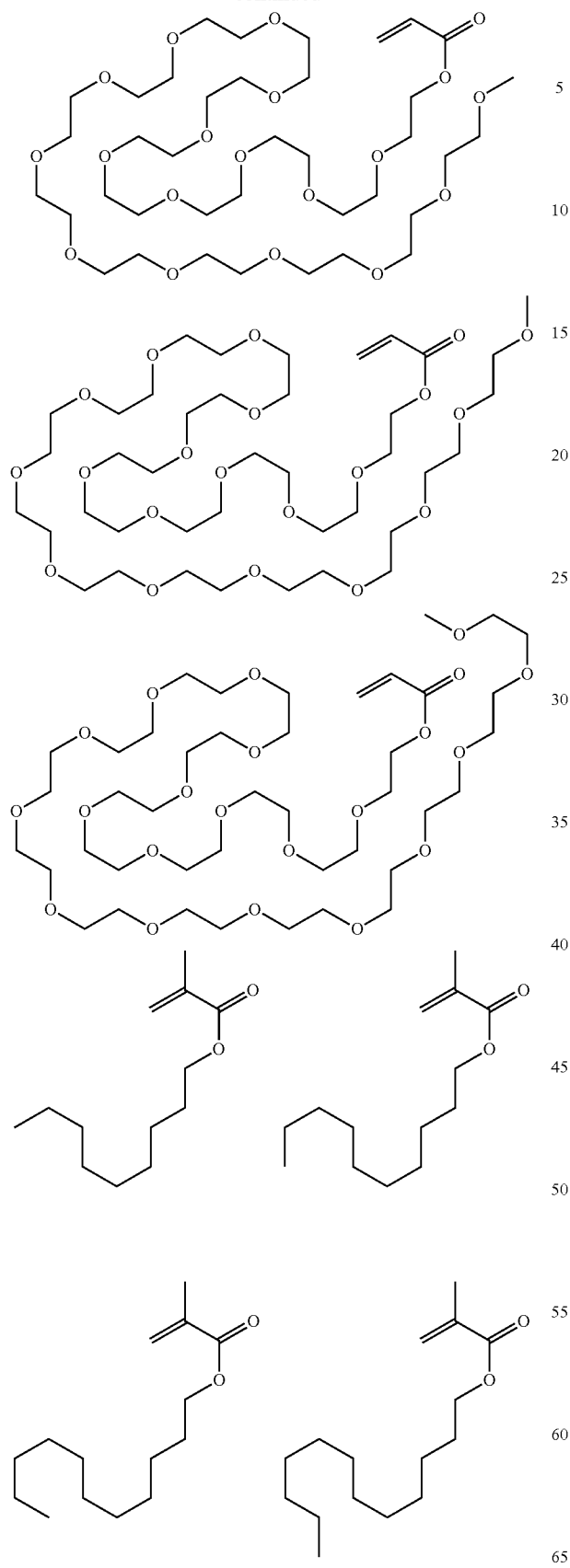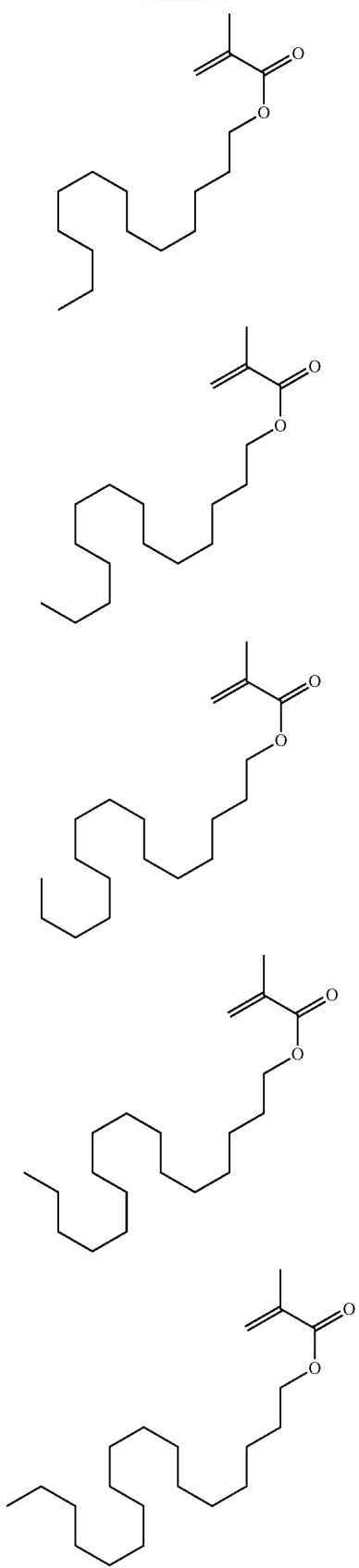

-continued
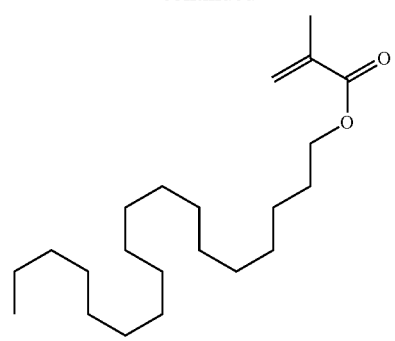
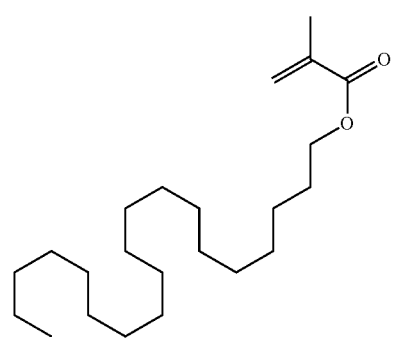
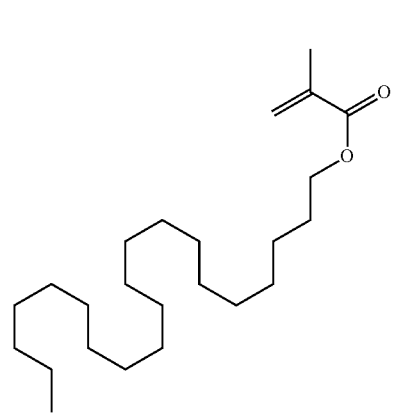
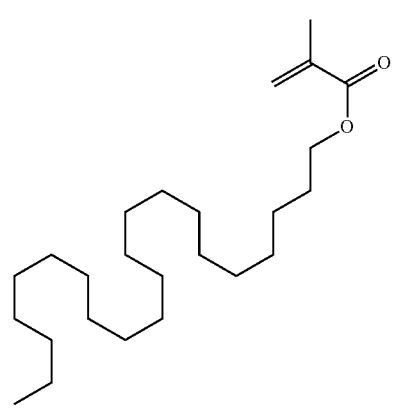
-continued
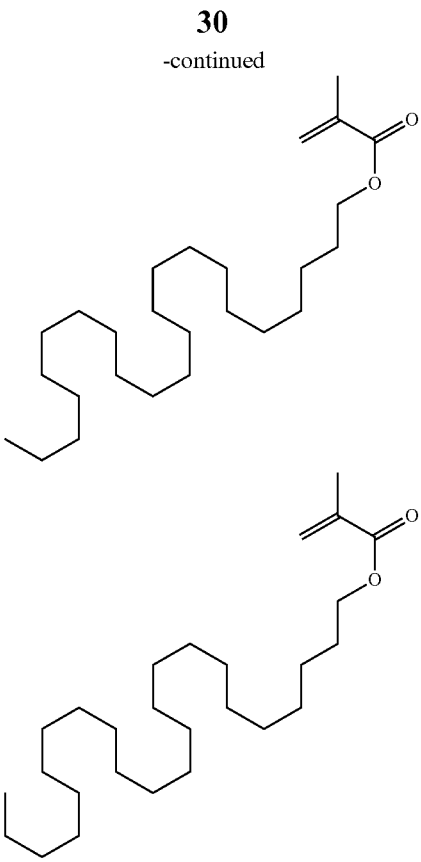
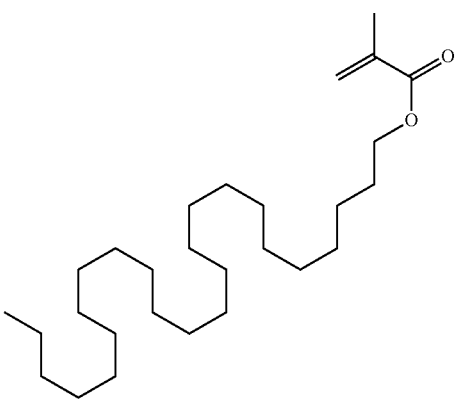
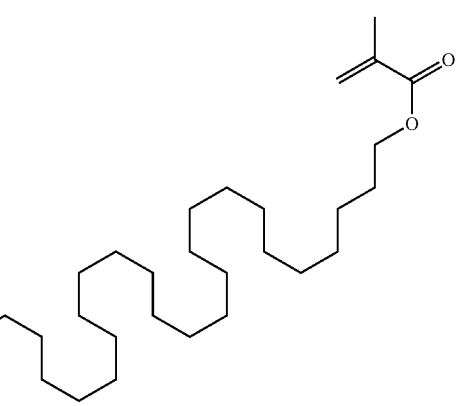

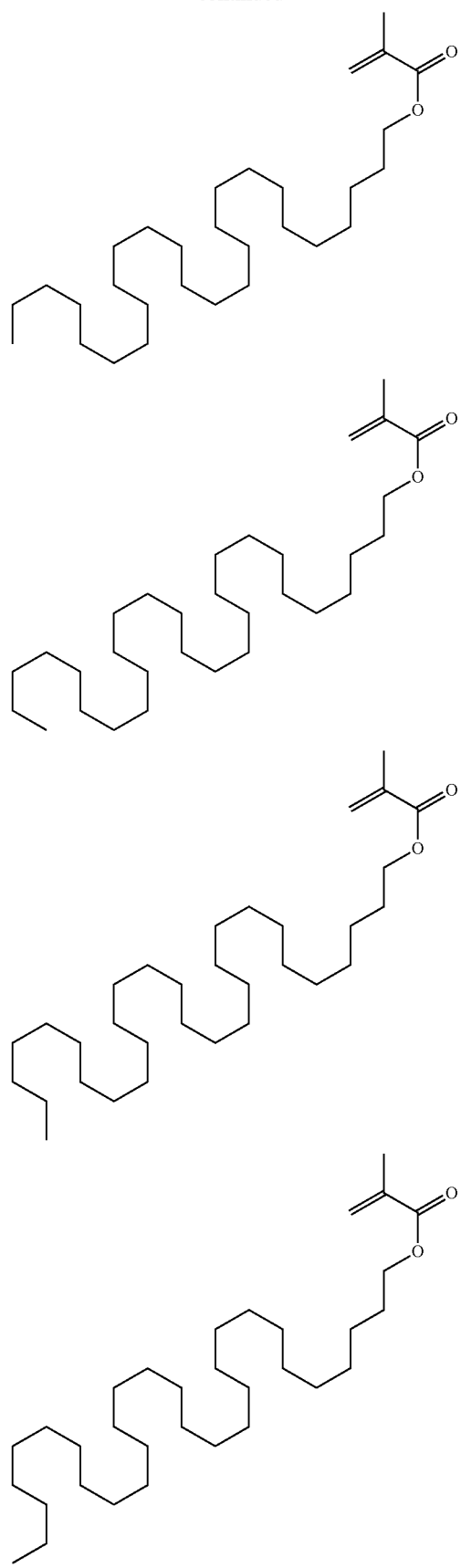
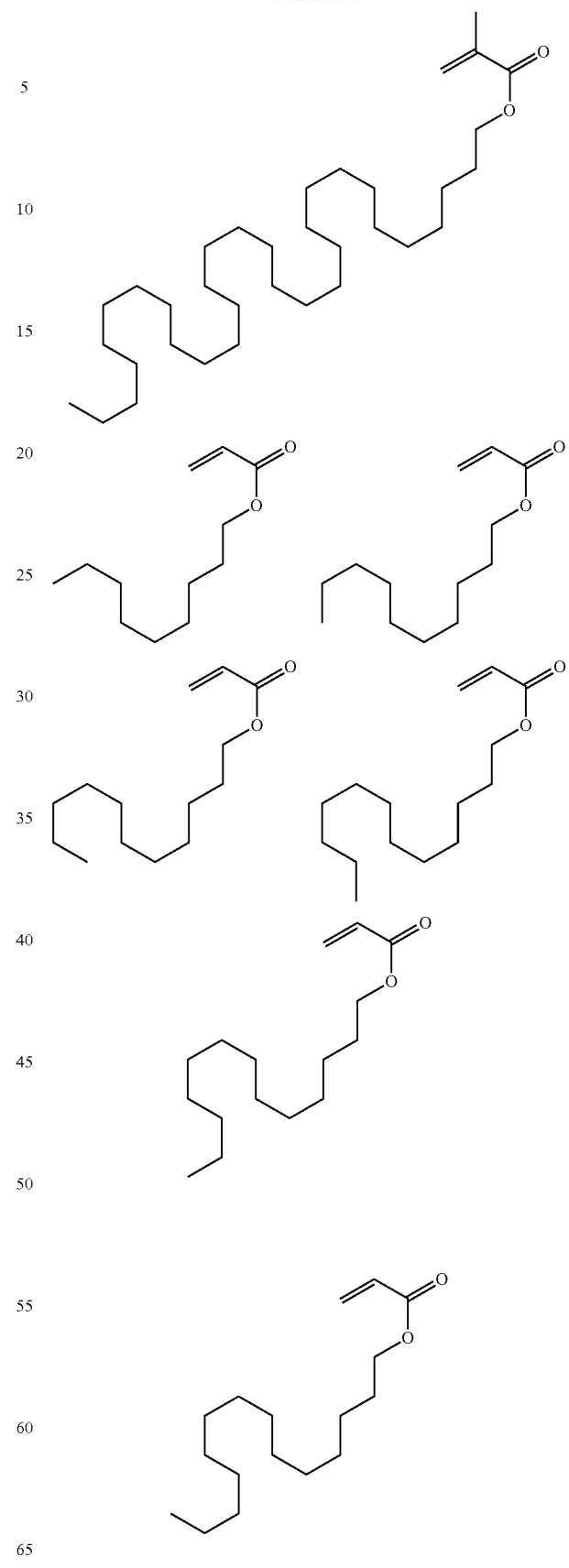

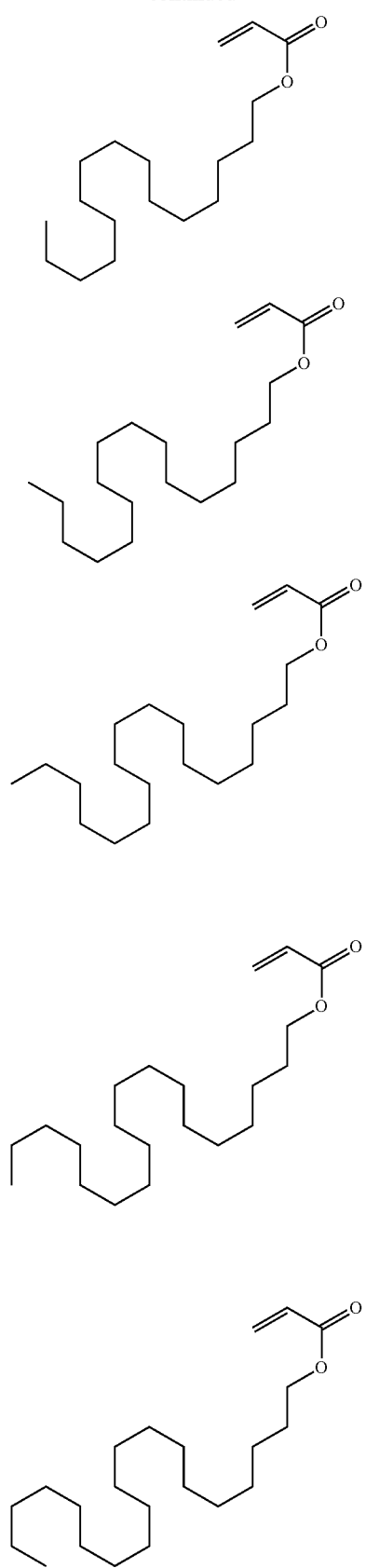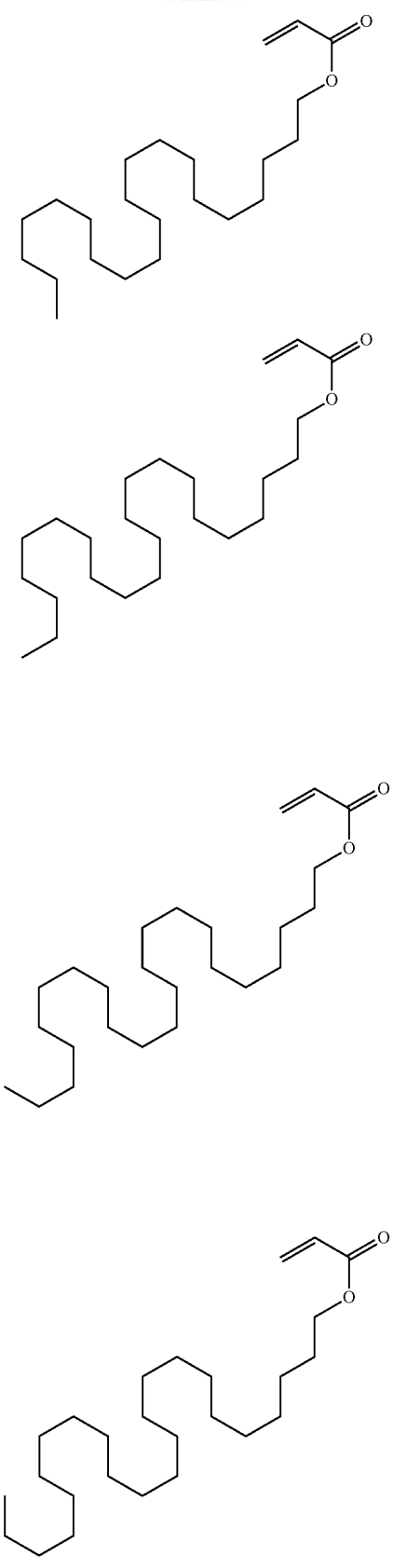

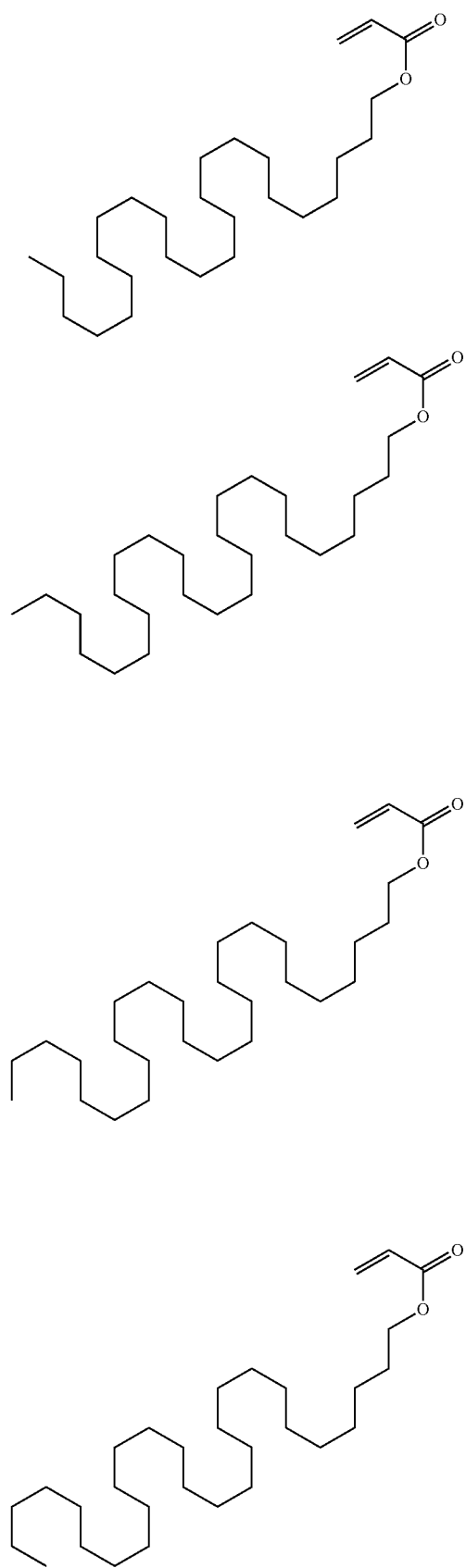
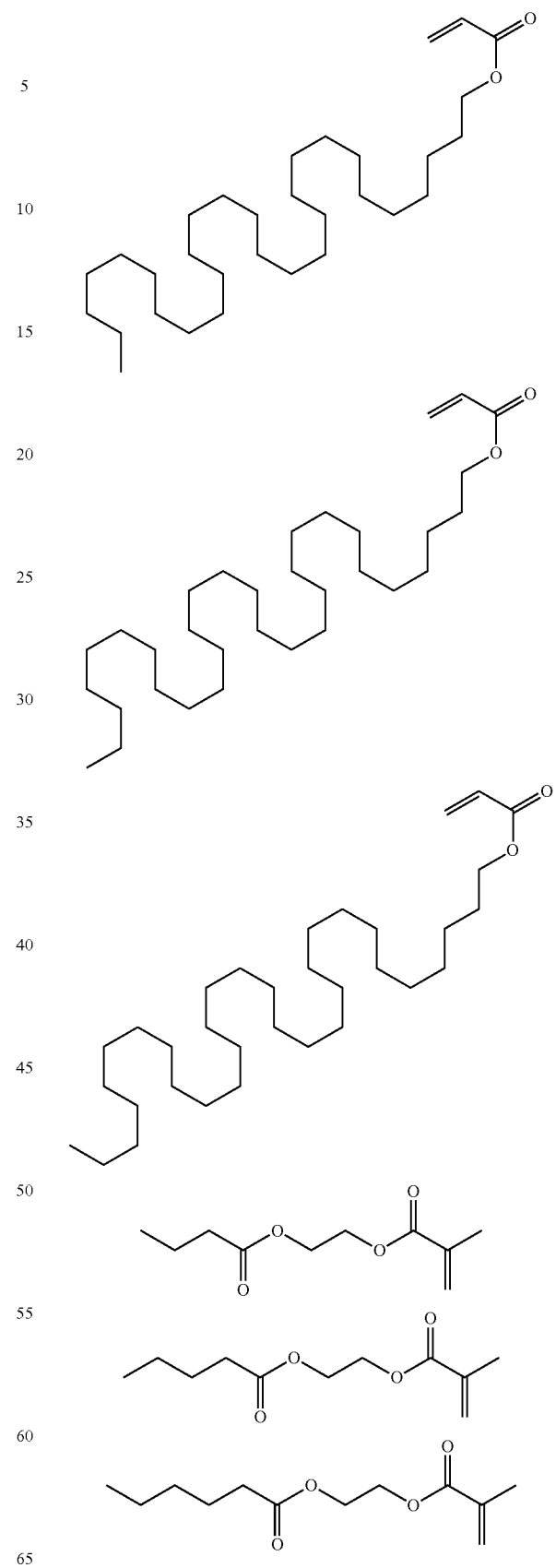

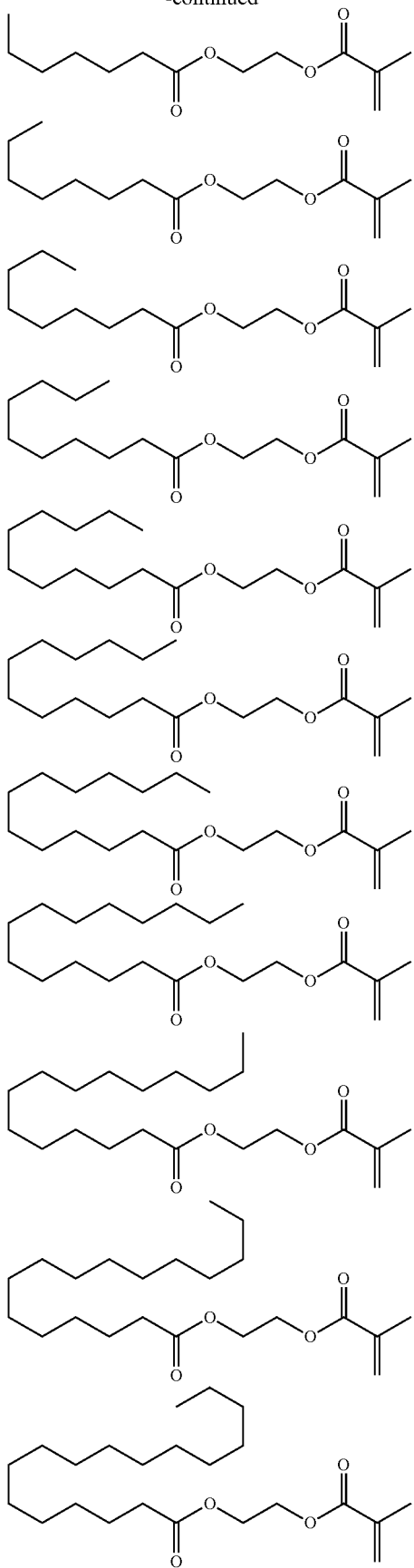
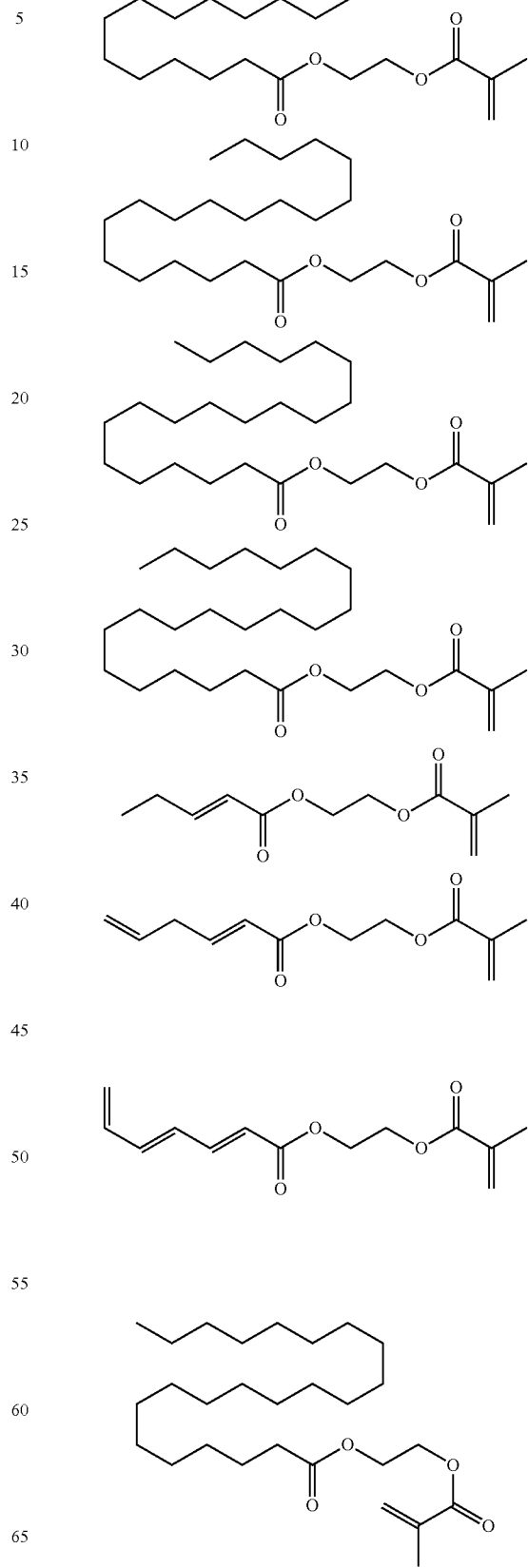

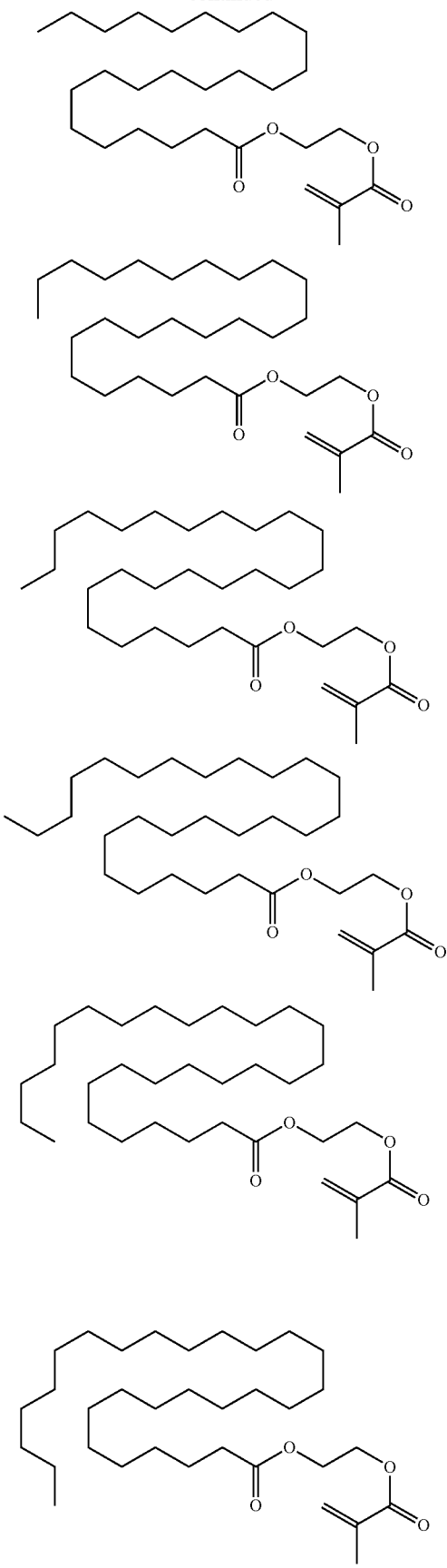
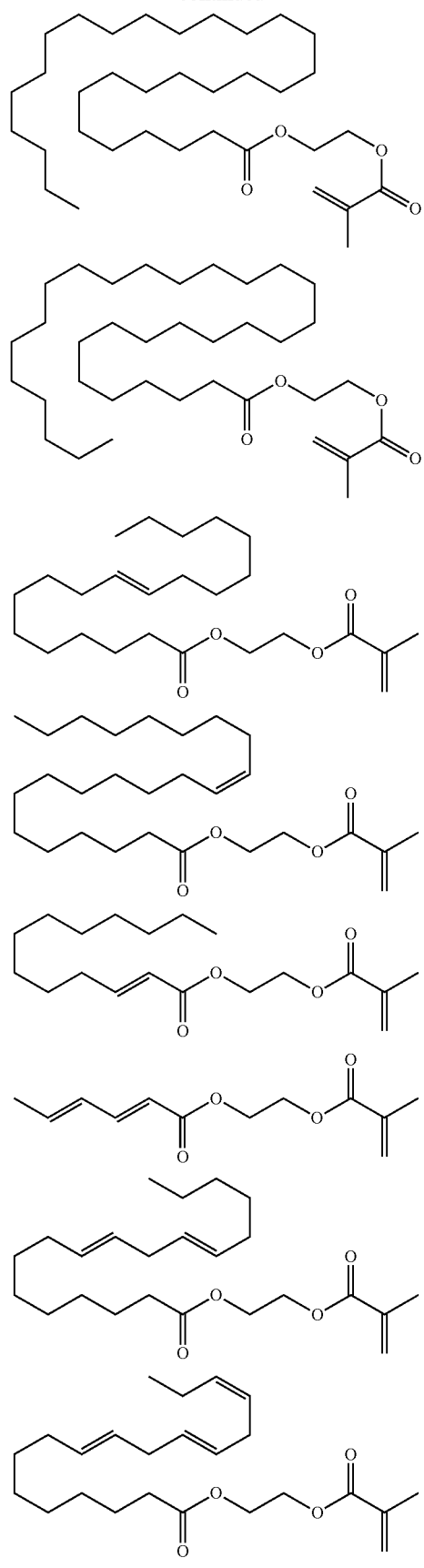

-continued
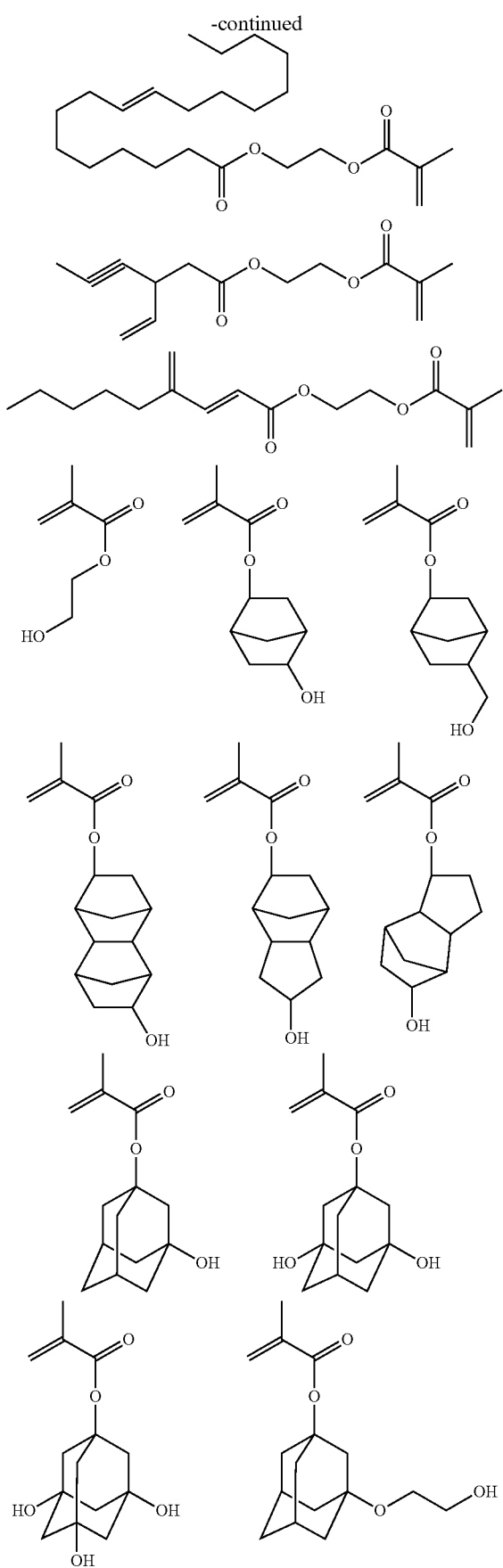
-continued
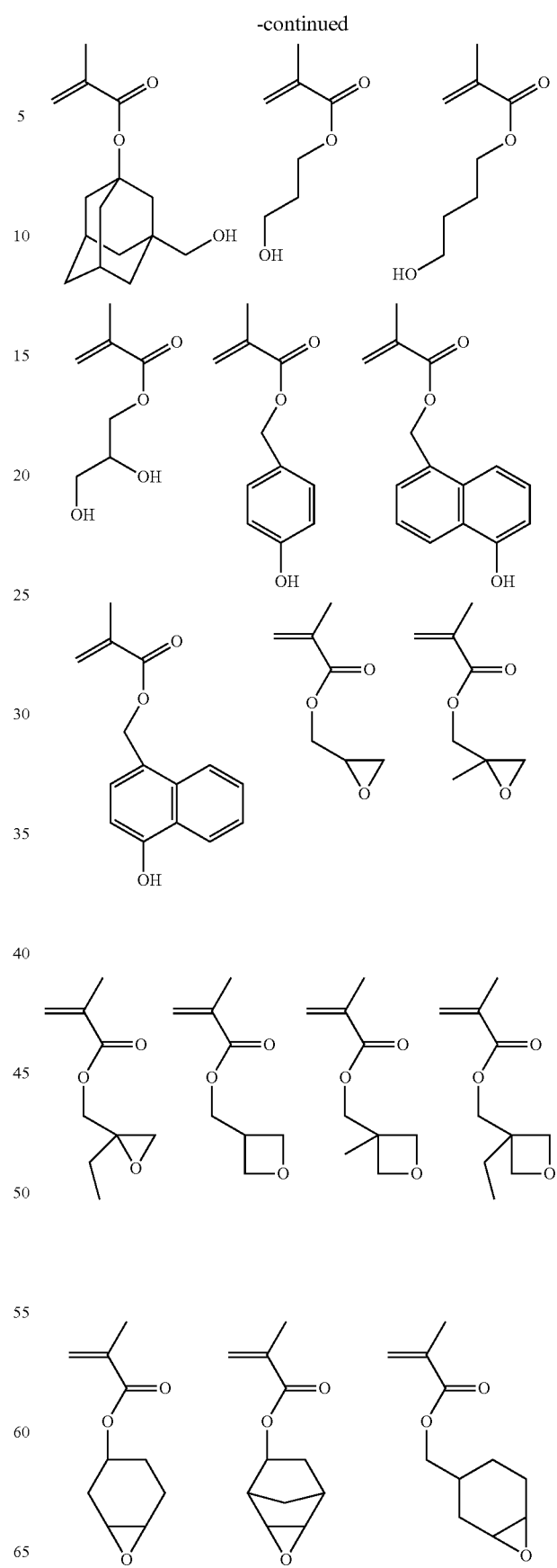

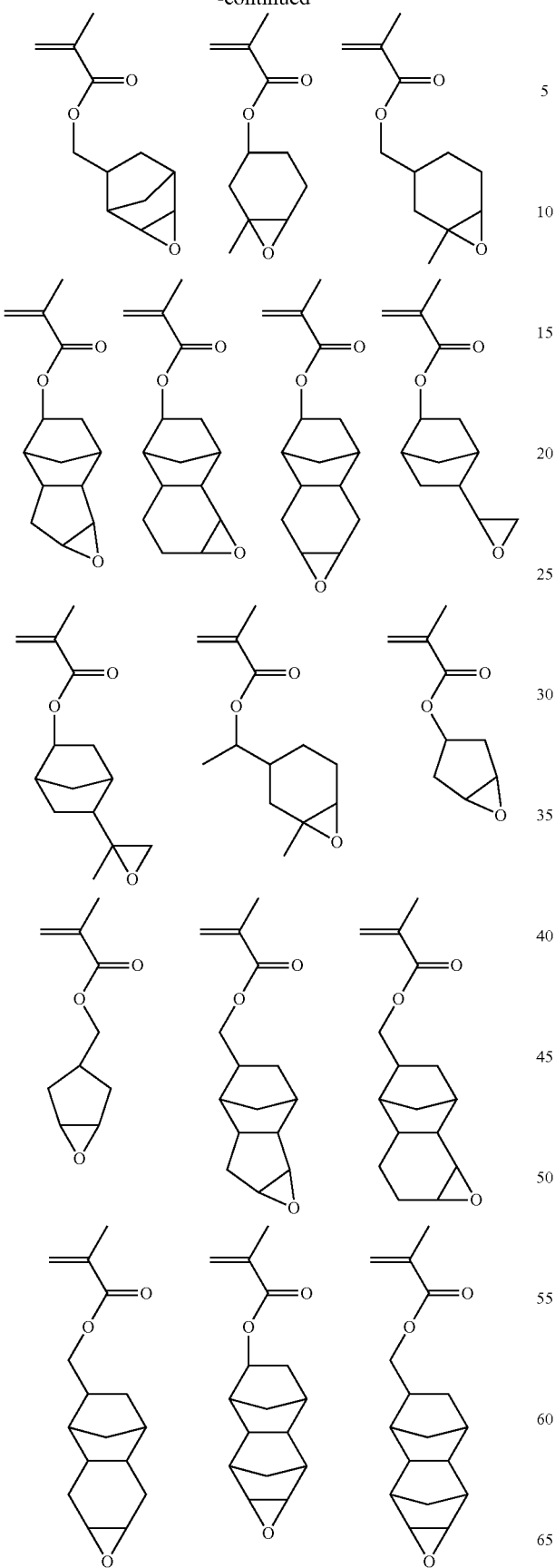
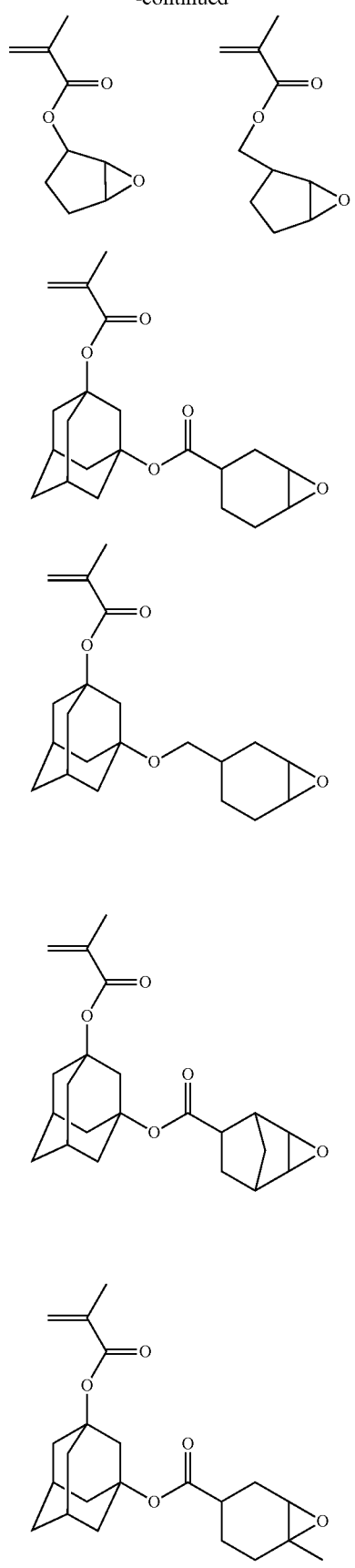

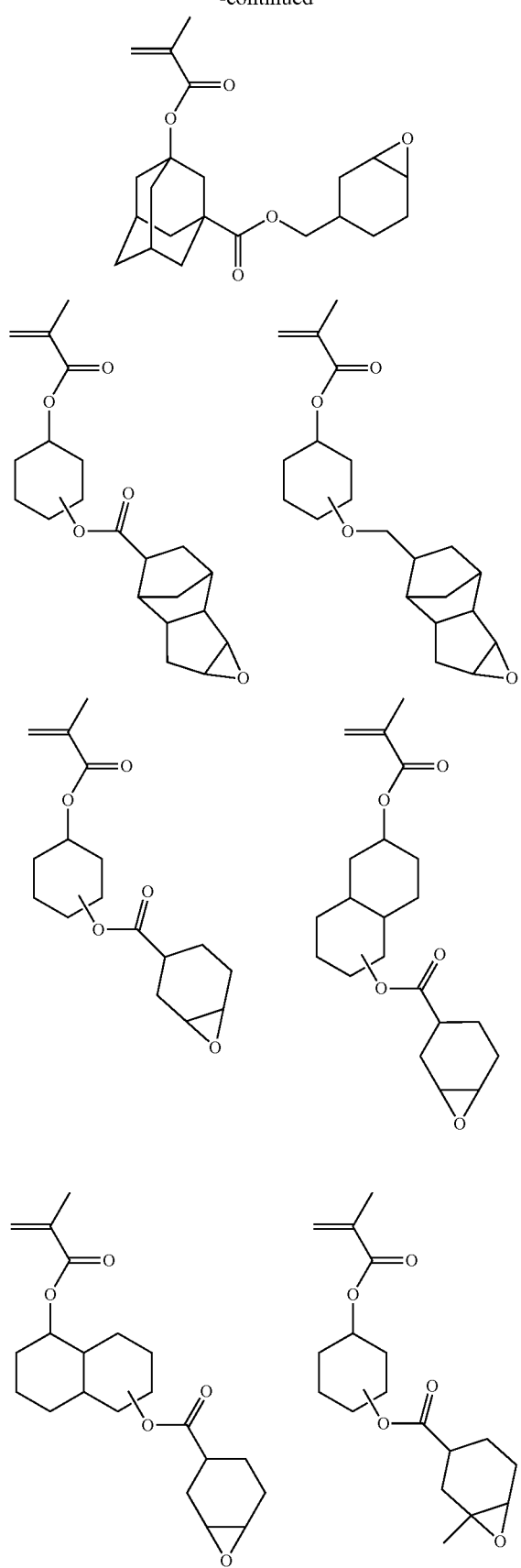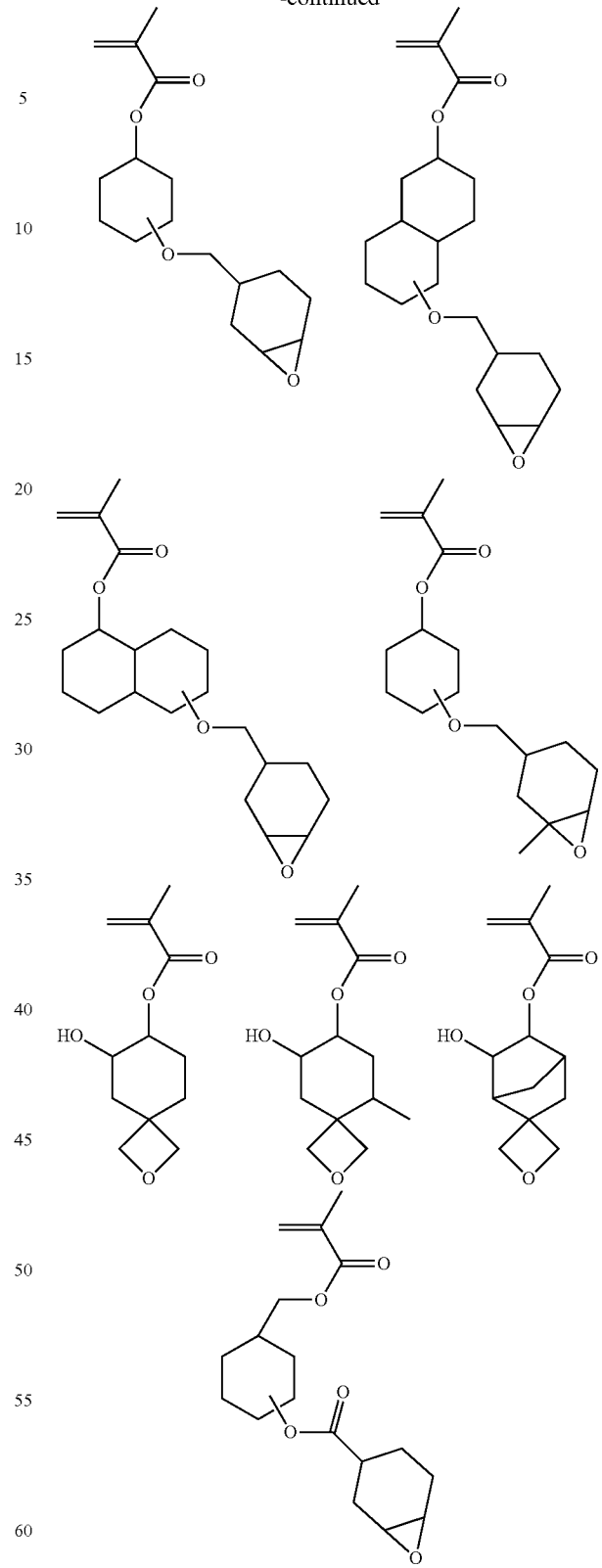
Furthermore, it is preferable that the polymer compound in the biological electrode composition of the present invention be a copolymerized polymer compound further having, in addition to the repeating unit "a" and the repeating unit "b", any one or both of a repeating unit "c" having a fluorine atom or a silicon atom and a repeating unit "d" having one or more groups selected from a hydroxy group, a carboxyl group, an oxirane group, and an oxetane group.

The repeating unit "c" is a repeating unit giving a water-repelling property, and when the repeating unit "c" is copolymerized, the change in conductivity by sweat and washing can be avoided. Also, the repeating unit "d" is a repeating unit giving a crosslinking property, and when the repeating unit "d" is copolymerized, the peeling-off from the conductive substrate can be avoided.

With regard to the monomer to obtain the repeating unit "c" which gives the water-repelling property, specifically the following monomers may be mentioned as the examples thereof,

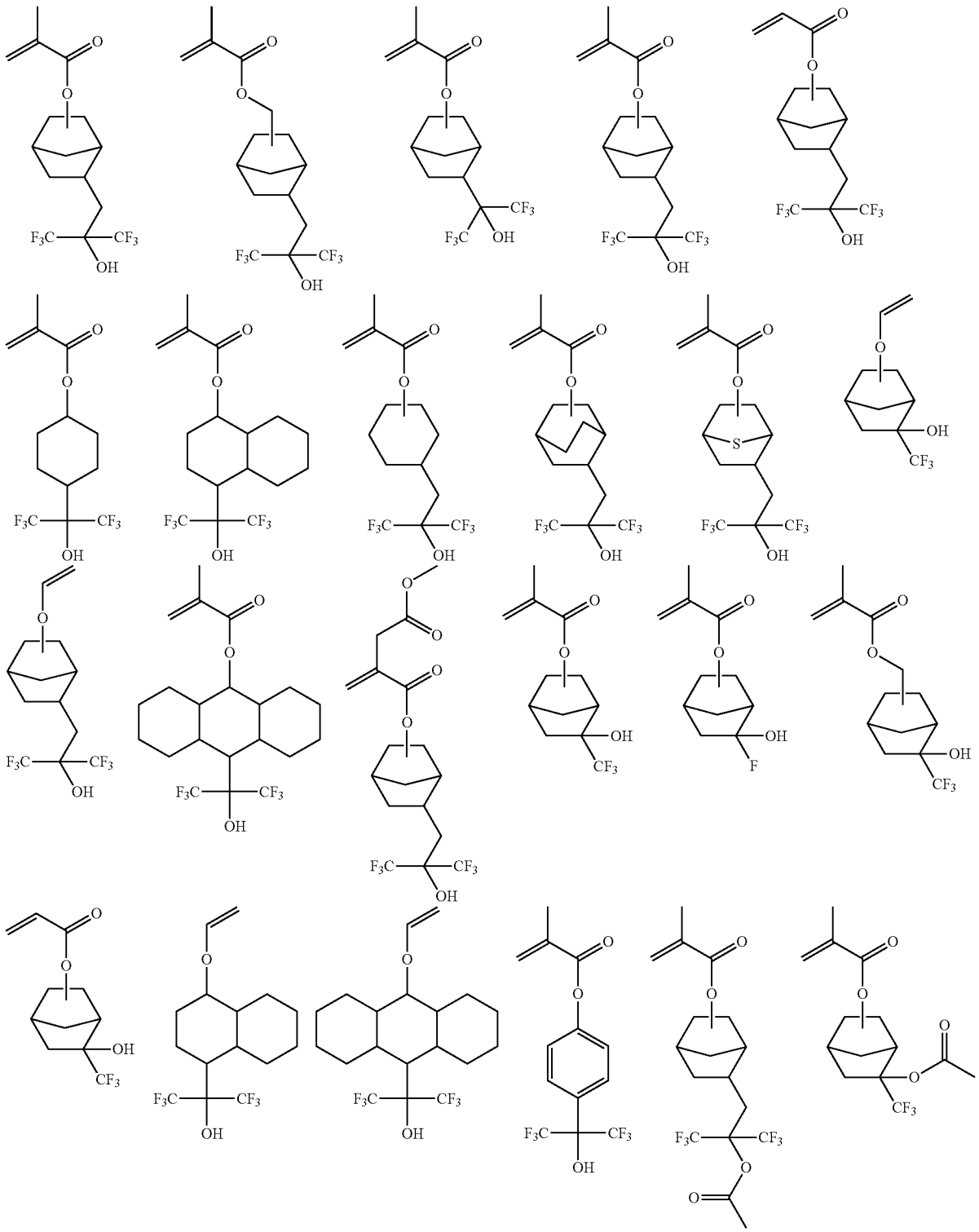

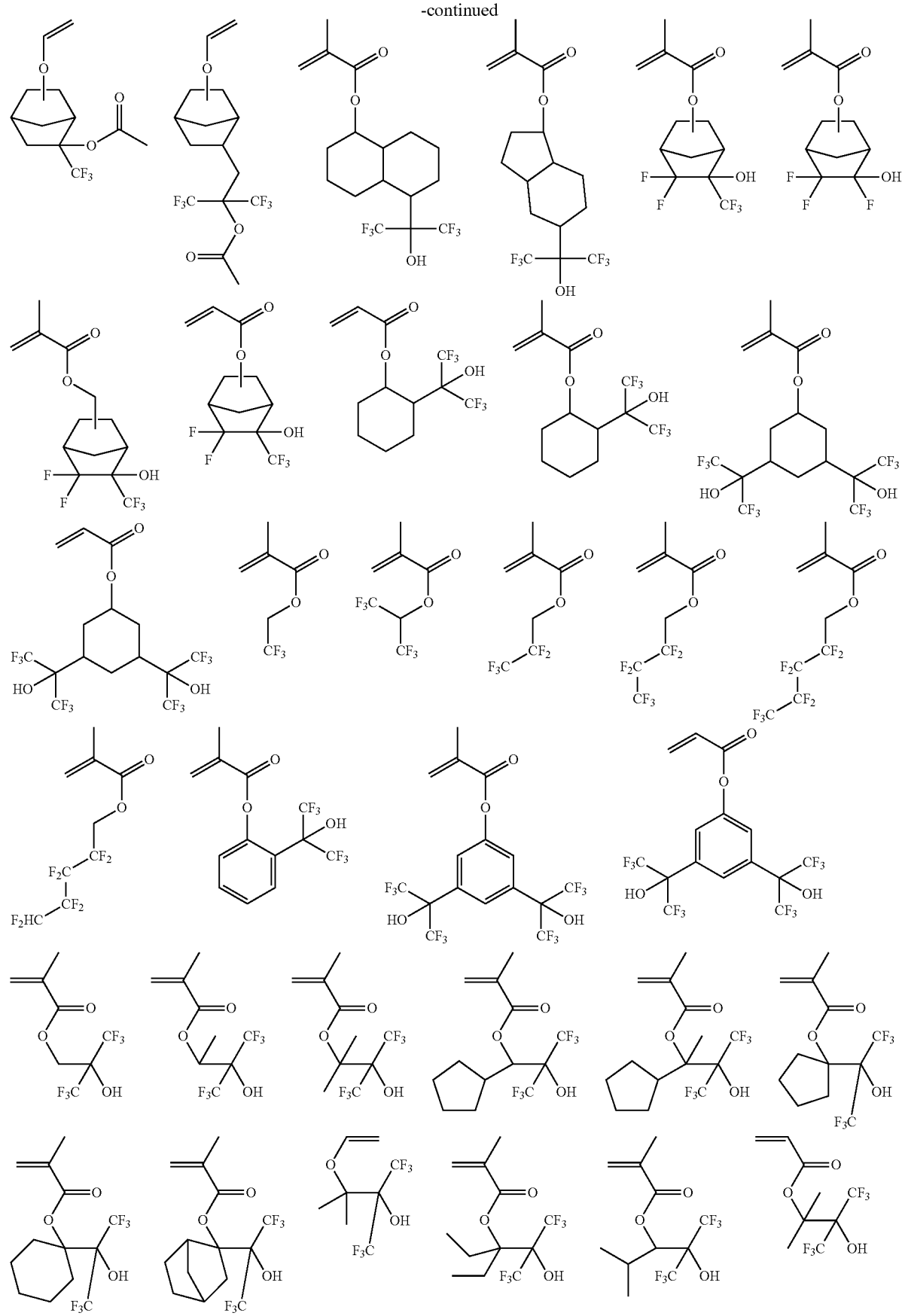

-continued
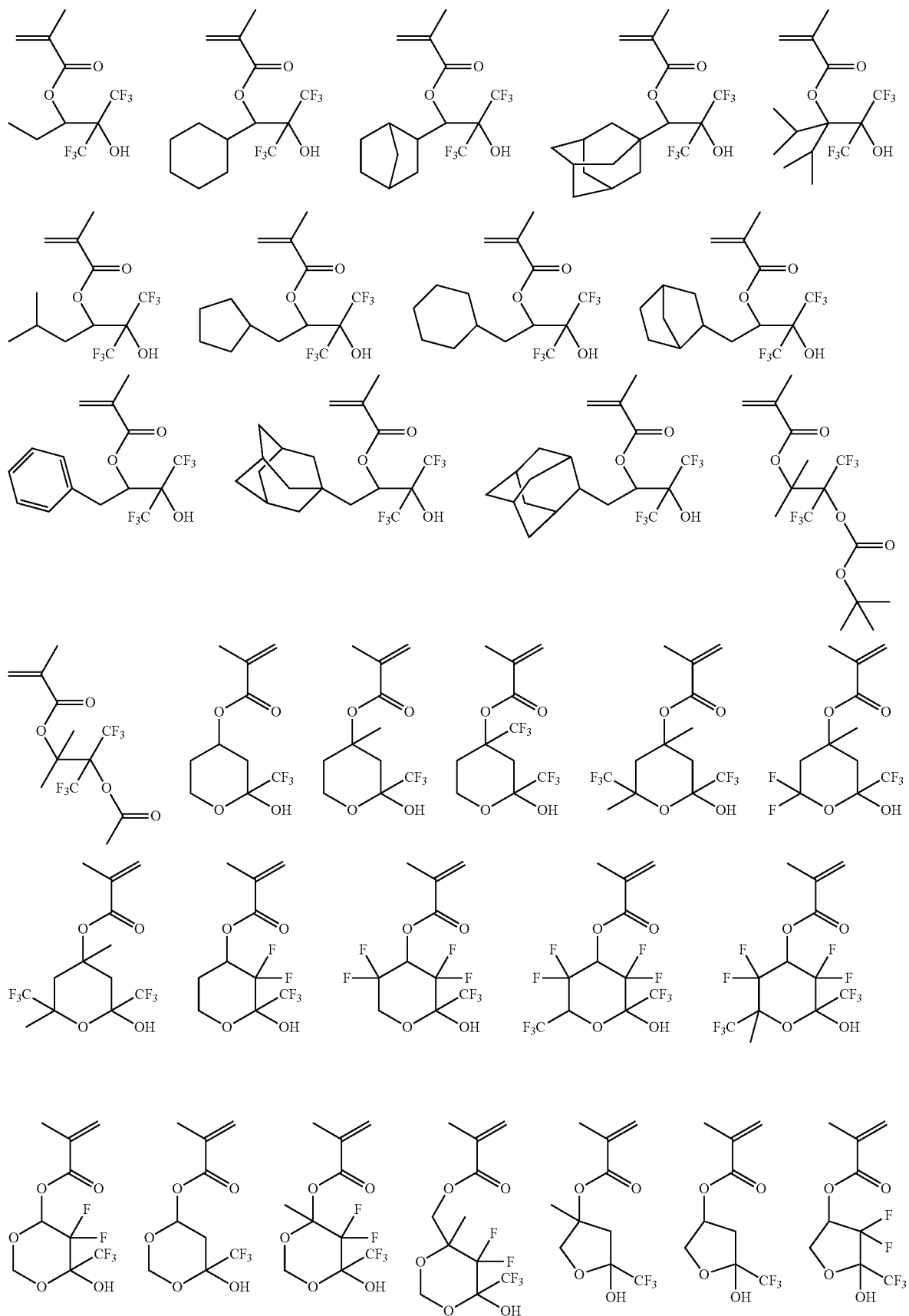

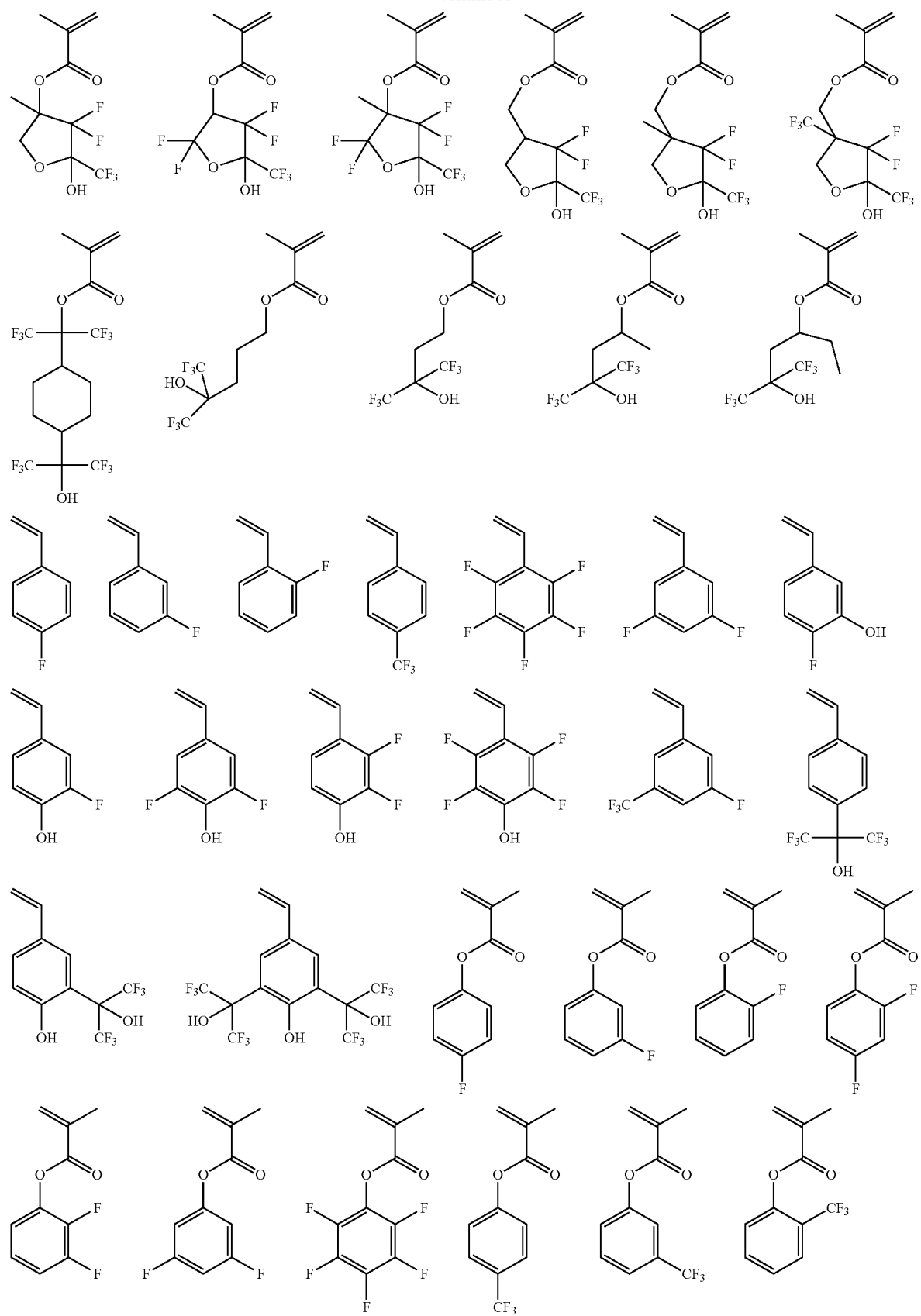

55
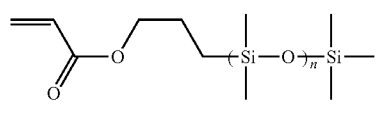
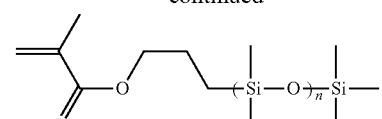
56
-continued
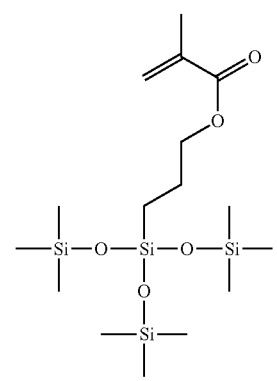
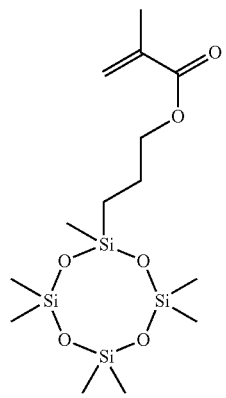
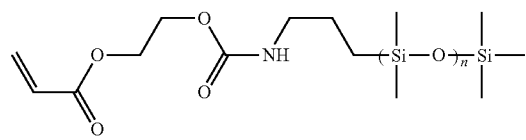
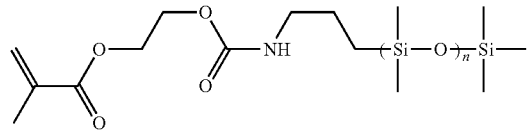
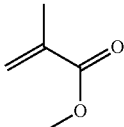
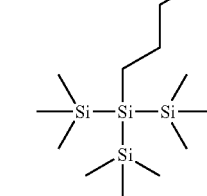
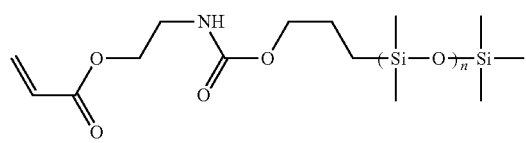
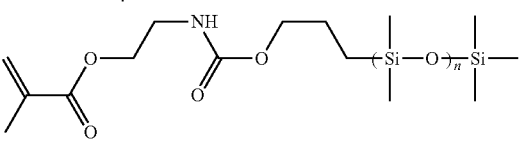
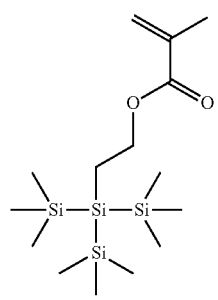
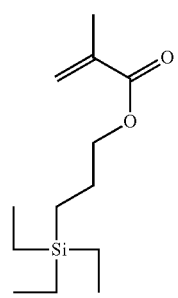
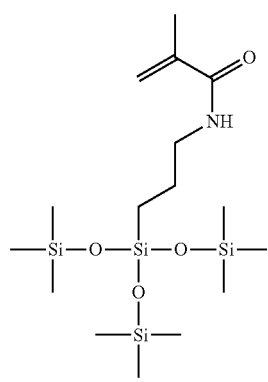
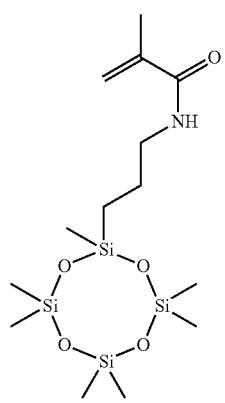

-continued
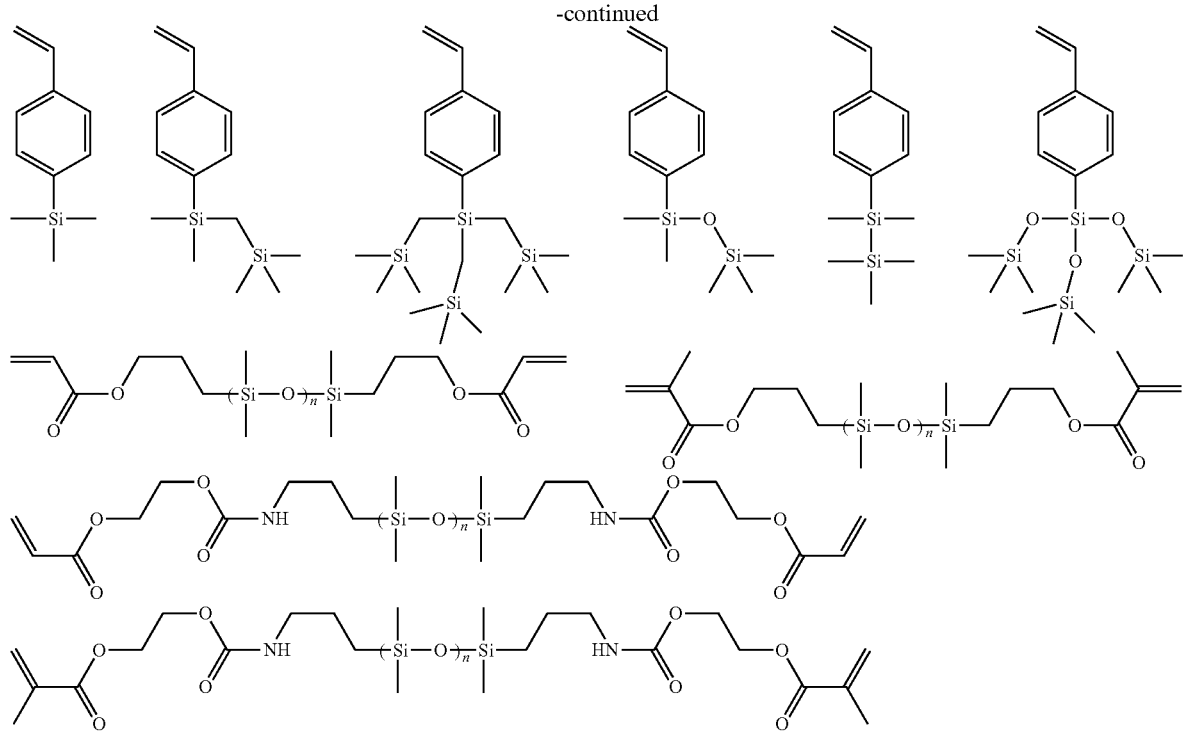
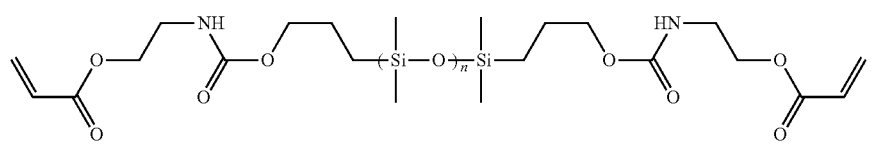
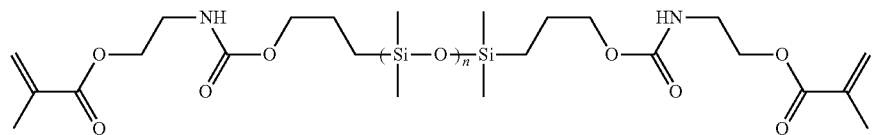
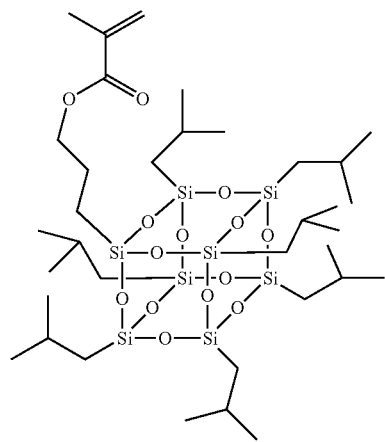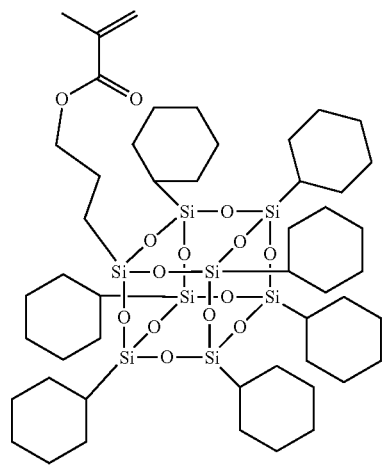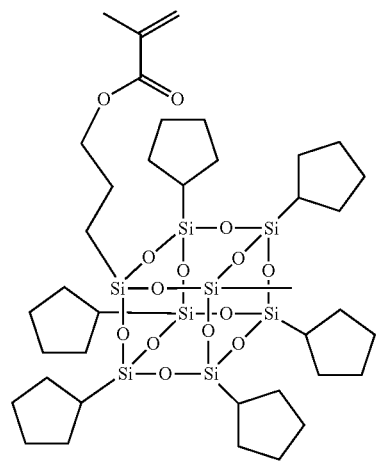
wherein, "n" represents an integer of 0 to 100.

With regard to the monomer to obtain the repeating unit "d" which gives the crosslinking property, specifically the following monomers may be mentioned as the examples thereof.
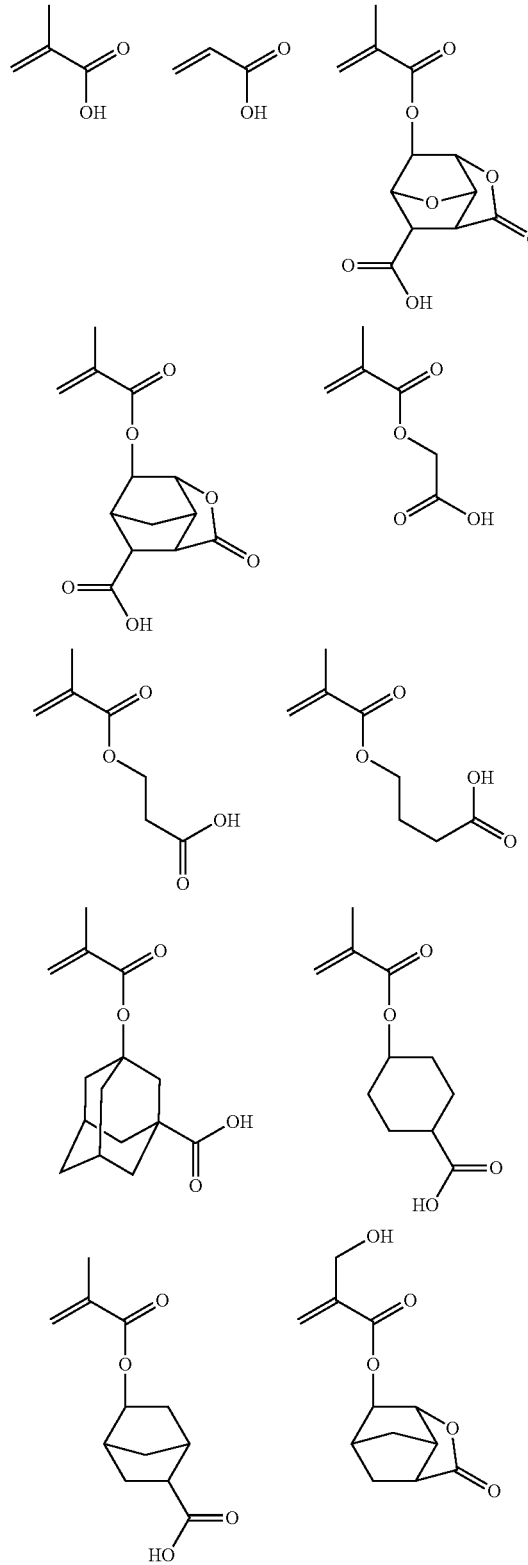
-continued
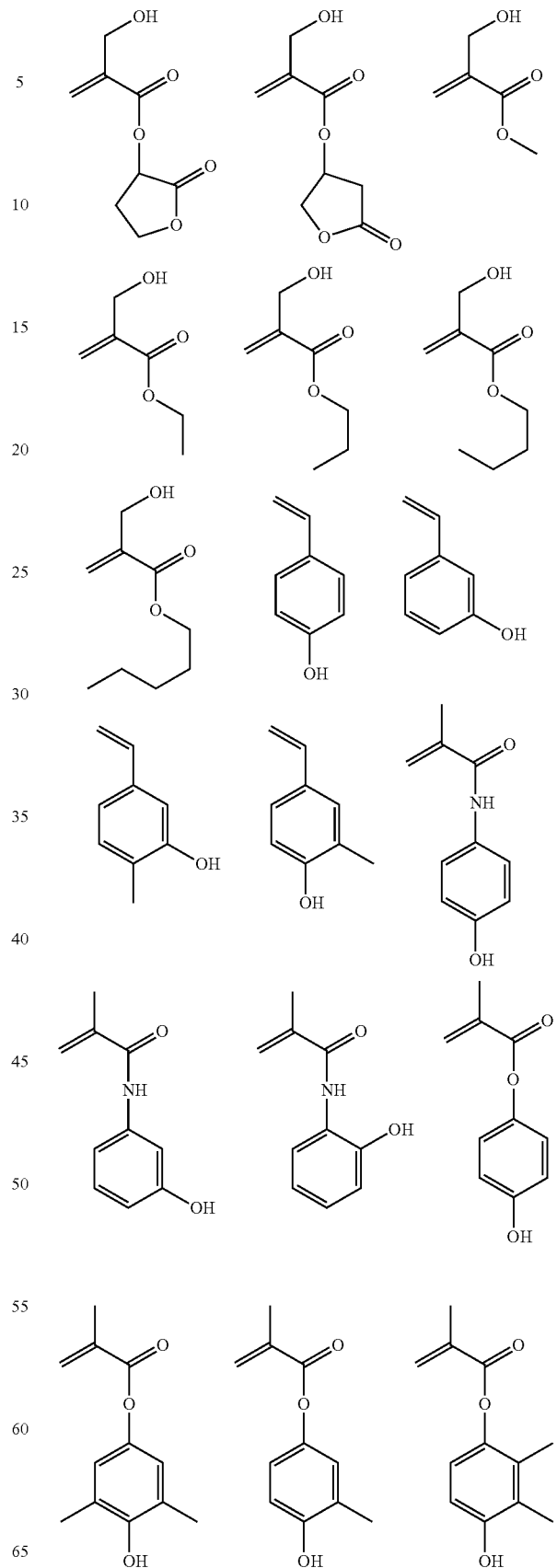

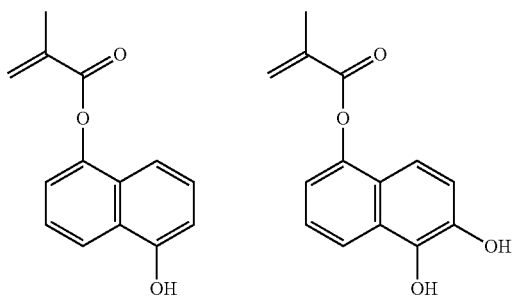
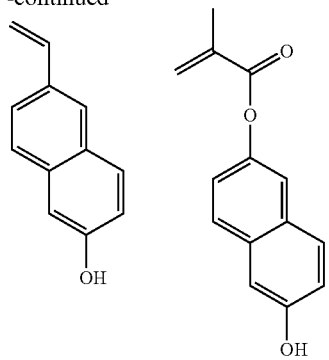
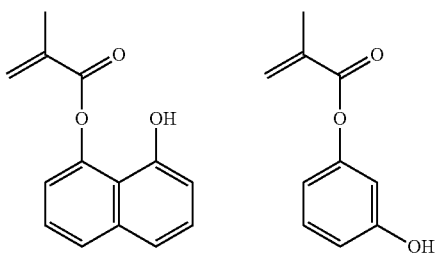
In addition, a monomer having plural polymerizable double bonds may further be copolymerized (repeating unit "e"). With these, crosslinking among polymers may be carried out after polymerization. With regard to the monomer having plural polymerizable double bonds, specifically the following monomers may be mentioned as the examples thereof,
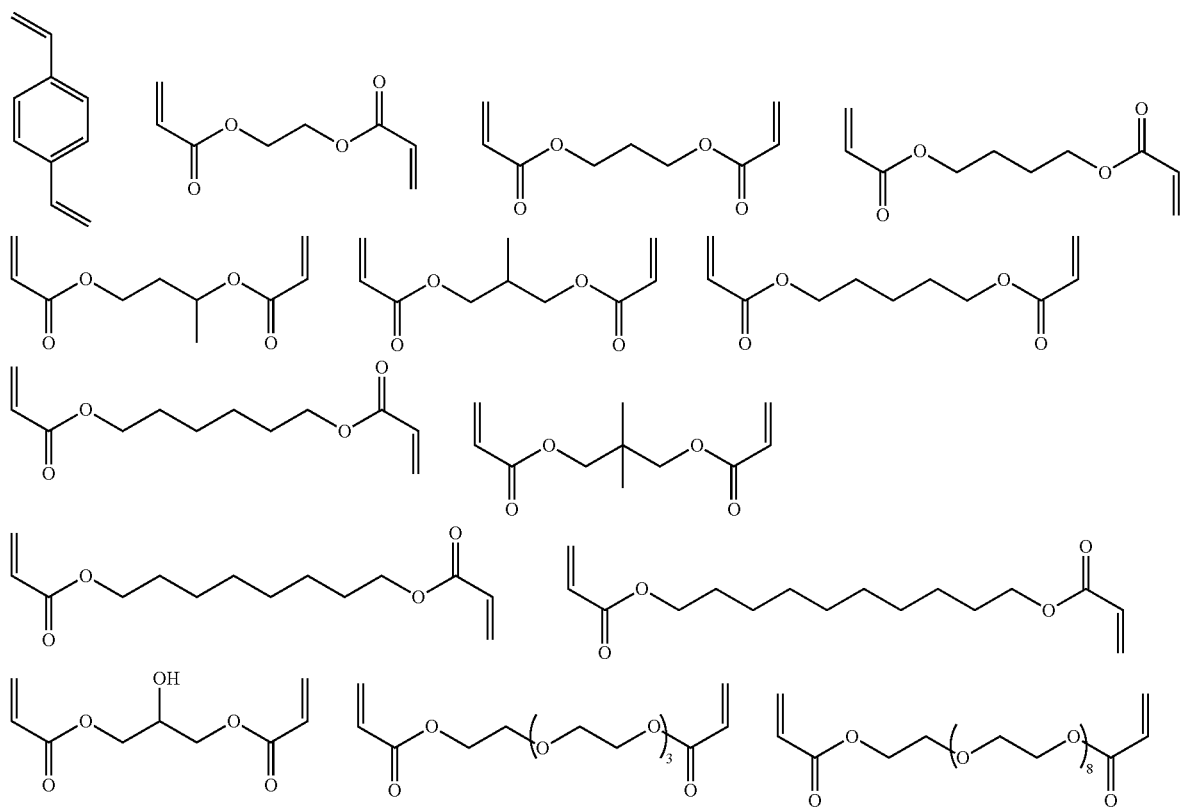

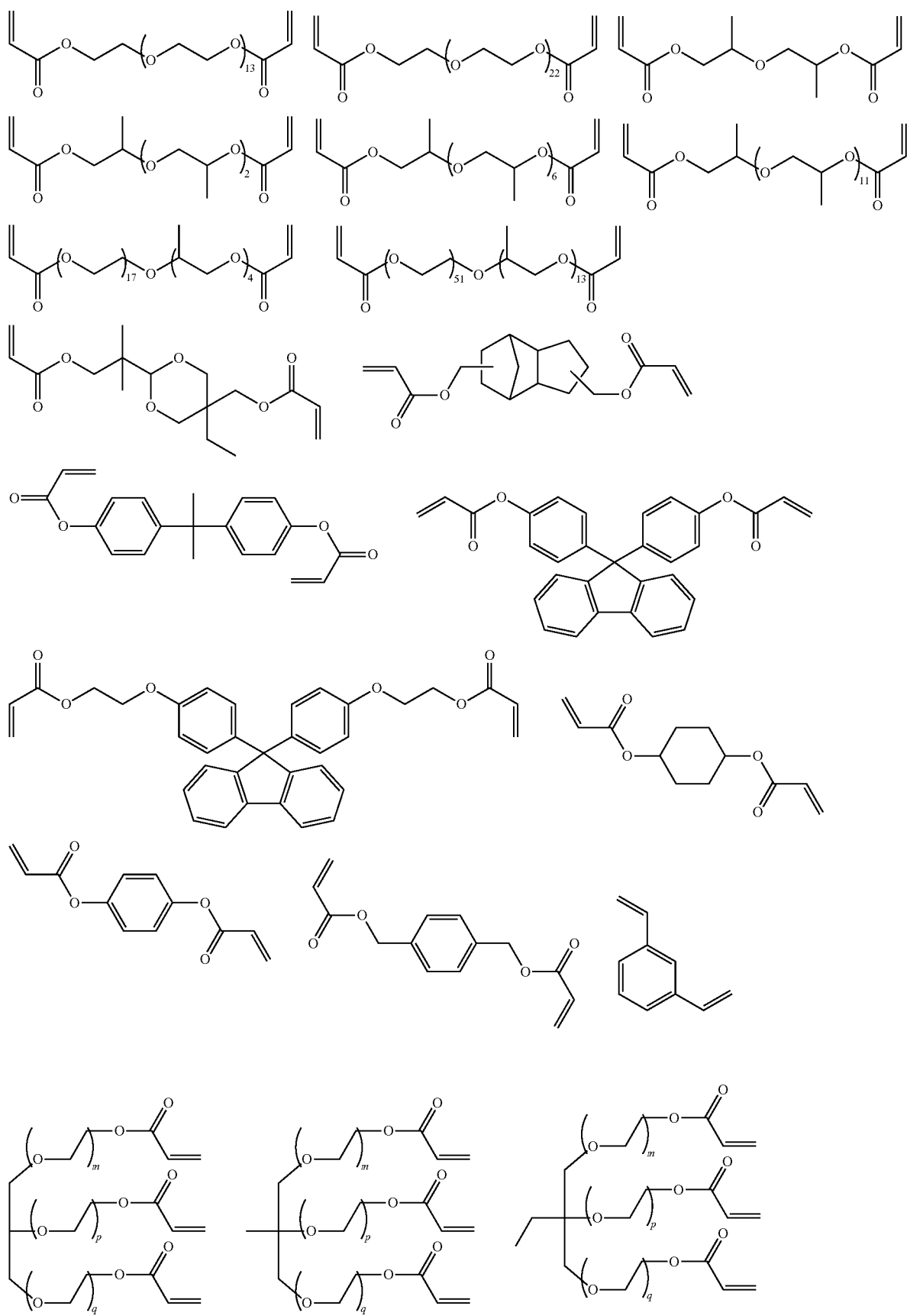

-continued
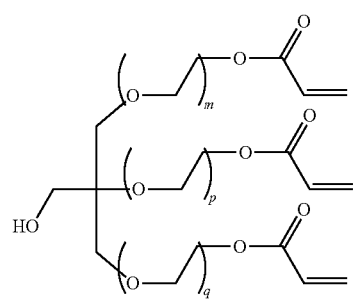
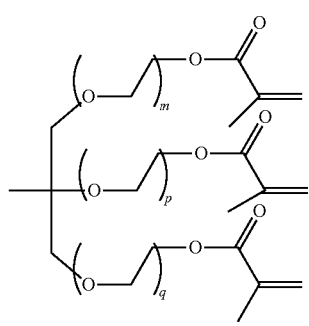
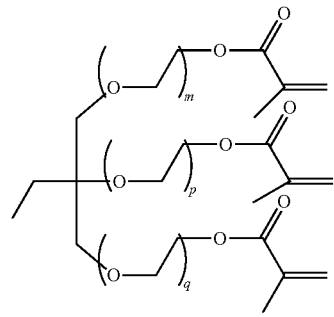
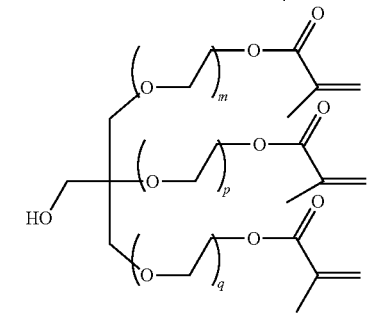
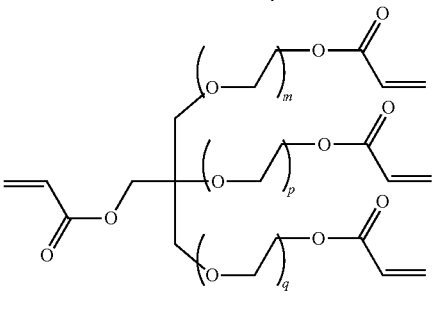
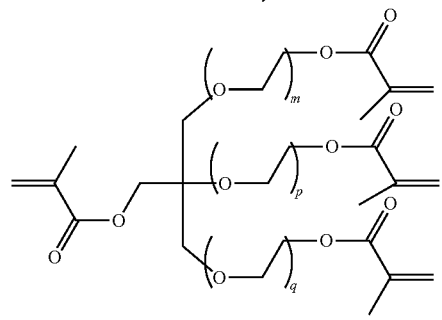
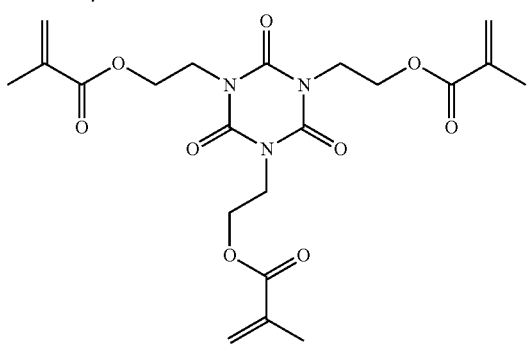
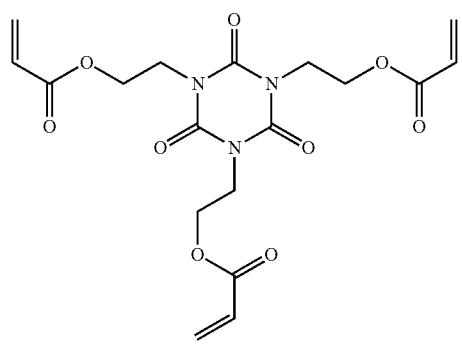
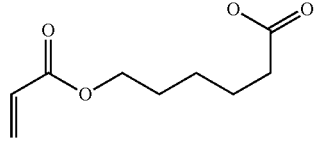
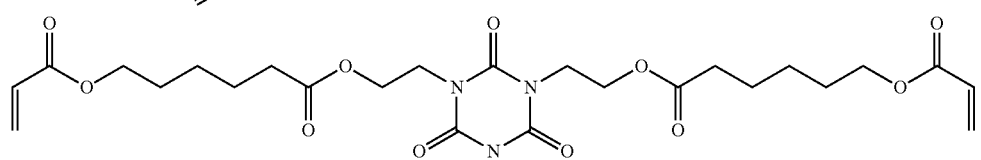
wherein, 3≤m+p+q≤30.

With regard to synthesis of the polymer compound as mentioned above, one method may be that among the monomers to give the repeating units "a", "b", "c", "d", and "e", by selecting intended monomers, a thermal polymerization is carried out in an organic solvent with adding a radical polymerization initiator to obtain a copolymer as the polymer compound.

Illustrative example of the organic solvent to be used in the polymerization includes toluene, benzene, tetrahydrofuran, diethyl ether, and dioxane. Illustrative example of the polymerization initiator includes 2,2'-azobisisobutyronitrile (AIBN), 2,2'-azobis(2,4-dimethylvaleronitrile), dimethyl-2,2-azobis(2-methylpropionate), benzoyl peroxide, and lauroyl peroxide. The polymerization can be carried out by heating the mixture thus prepared at 50 to 80° C. with the reaction time of 2 to 100 hours, while preferably 5 to 20 hours.

In the alternative way of copolymerizing hydroxy styrene or hydroxy vinyl naphthalene, in place of hydroxy styrene or hydroxy vinyl naphthalene, acetoxy styrene or acetoxy vinyl naphthalene is polymerized, and thereafter, the acetoxy group thereof is deprotected by an alkaline hydrolysis to obtain polyhydroxy styrene or hydroxy polyvinyl naphthalene.

With regard to the base to be used in the alkaline hydrolysis, an aqueous ammonia solution, triethyl amine, or the like may be mentioned. The reaction temperature is −20 to 100° C., while preferably 0 to 60° C.; and the reaction time is 0.2 to 100 hours, while preferably 0.5 to 20 hours.

When the polymer compound in the biological electrode composition of the present invention contains the repeating unit a1, the ratio of the repeating units a1, "b", "c", "d", and "e" is $0<a1<1.0$, $0<b<1.0$, $0\le c<1.0$, $0\le d\le 0.7$, and $0\le e\le 0.4$, preferably $0<a1\le 0.9$, $0.05\le b\le 0.9$, $0\le c\le 0.8$, $0\le d\le 0.6$, and $0\le e\le 0.3$, while more preferably $0<a1\le 0.8$, $0.1\le b\le 0.8$, $0\le c\le 0.7$, $0\le d\le 0.5$, and $0\le e\le 0.2$.

Meanwhile, for example, a+b+c=1 means that in the polymer compound including the repeating units "a", "b", and "c", total amount of the repeating units "a", "b", and "c" is 100% by mole relative to total amount of entire repeating units contained therein; and a+b+c<1 means that total amount of the repeating units "a", "b", and "c" is less than 100% by mole relative to total amount of entire repeating units contained therein, indicating that there is a repeating unit other than "a", "b", and "c".

The molecular weight of the polymer compound is preferably, as the weight average molecular weight, 500 or more, more preferably 1,000 or more and 1,000,000 or less, while still more preferably 2,000 or more and 500,000 or less. When amount of an ionic monomer not incorporated into the polymer compound after polymerization (i.e., residual monomer) is small, there is no risk of causing an allergy due to penetration of this residual monomer into a skin in a biocompatibility test; and thus, it is preferable to reduce the amount of the residual monomer. Preferably, the amount of the residual monomer is 10% or less by mass of 100 parts by mass of the entire polymer compound.

[Organic Solvent]

The biological electrode composition of the present invention may be added with an organic solvent. Specific example of the organic solvent includes aromatic hydrocarbon solvents such as toluene, xylene, cumene, 1,2,3-trimethyl benzene, 1,2,4-trimethyl benzene, 1,3,5-trimethyl benzene, styrene, α-methyl styrene, butyl benzene, sec-butyl benzene, isobutyl benzene, cymene, diethyl benzene, 2-ethyl-p-xylene, 2-propyl toluene, 3-propyl toluene, 4-propyl toluene, 1,2,3,5-tetramethyl toluene, 1,2,4,5-tetramethyl toluene, tetrahydronaphthalene, 4-phenyl-1-butene, tert-amyl benzene, amyl benzene, 2-tert-butyl toluene, 3-tert-butyl toluene, 4-tert-butyl toluene, 5-isopropyl-m-xylene, 3-methyl ethylbenzene, tert-butyl-3-ethyl benzene, 4-tert-butyl-o-xylene, 5-tert-butyl-m-xylene, tert-butyl-p-xylene, 1,2-diisopropyl benzene, 1,3-diisopropyl benzene, 1,4-diisopropyl benzene, dipropyl benzene, 3,9-dodecadiyne, pentamethyl benzene, hexamethyl benzene, hexyl benzene, and 1,3,5-triethyl benzene; aliphatic hydrocarbon solvents such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinyl cyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isoproyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvents such as cyclohexanone, cyclopentanone, 2-octanone, 2-nonanone, 2-heptanone, 3-heptanone, 4-heptanone, 2-hexanone, 3-hexanone, diisobutyl ketone, methyl cyclohexanone, and methyl-n-pentyl ketone; alcohol solvents such as 3-methoxybutanol, 3-methyl-3-methoxybutanol, 1-methoxy-2-propanol, and 1-ethoxy-2-propanol; ether solvents such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, diisopentyl ether, di-sec-pentyl ether, di-tert-amyl ether, di-n-hexyl ether, and anisole; ester solvents such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactone solvents such as γ-butyrolactone.

Meanwhile, addition amount of the organic solvent is preferably 10 to 50,000 parts by mass relative to 100 parts by mass of the polymer compound.

[Carbon Material]

In order to increase the conductivity furthermore, as a conductivity enhancer, a carbon material can be added to the biological electrode composition of the present invention. Illustrative example of the carbon material includes a carbon black and a carbon nanotube. With regard to the carbon nanotube, any of a monolayer and a multiple layer may be used; and they may be modified with an organic group on the surface thereof. Addition amount of the carbon material is preferably 1 to 50 parts by mass relative to 100 parts by mass of the polymer compound.

[Conductivity Enhancer Other Than the Carbon Material]

To the biological electrode composition of the present invention, a conductivity enhancer other than the carbon material may also be added. Specific example thereof includes particles of a resin coated with noble metals such as gold, silver, and platinum, as well as with copper and nickel; nanoparticles of the metals such as gold, silver, and platinum; and particles of metal oxides such as an indium tin oxide (ITO), an indium zinc oxide (IZO), a tin oxide, and a zinc oxide. Especially preferable is an ITO particle, or a particle coated with a metal selected from silver, gold, platinum, copper, and nickel.

[Crosslinking Agent]

In order to avoid attachment of the living body contact layer to a skin after the biological electrode is removed from the skin, a crosslinking agent may be added thereto. Specific example of the crosslinking agent usable in the present invention includes melamine compounds substituted with at least one group selected from a methylol group, an alkoxymethyl group, and an acyloxymethyl group; a guanamine compound; a glycoluril compound or a urea compound; an epoxy compound; an isocyanate compound; an azide compound, and a compound having a double bond such as an alkenyl ether group. These may be used as an additive; or alternatively, they may be introduced into a side chain of the polymer compound as a pendant group. Also, a compound having a hydroxy group may be used as the crosslinking agent.

Illustrative example of the epoxy crosslinking agent includes tris(2,3-epoxypropyl)isocyanurate, trimethylolmethane triglycidyl ether, trimethylolpropane triglycidyl ether, triethylolethane triglycidyl ether, and an epoxy-containing silicone. Specific example of the melamine compound includes hexamethylol melamine, hexamethoxy methyl melamine, hexamethylol melamine whose 1 to 6 methylol groups are methoxymethylated or a mixture of them, hexamethoxy ethyl melamine, hexaacyloxy methyl melamine, and hexamethylol melamine whose 1 to 6 methylol groups are acyloxymethylated or a mixture of them. Illustrative example of the guanamine compound includes tetramethylol guanamine, tetramethoxy methyl guanamine, tetramethylol guanamine whose 1 to 4 methylol groups are methoxymethylated or a mixture of them, tetramethoxyethyl guanamine, tetraacyloxy guanamine, and tetramethylol guanamine whose 1 to 4 methylol groups are acyloxymethylated or a mixture of them. Illustrative example of the glycoluril compound includes tetramethylol glycoluril, tetramethoxy glycoluril, tetramethoxy methyl glycoluril, tetramethylol glycoluril whose 1 to 4 methylol groups are methoxymethylated or a mixture of them, and tetramethylol glycoluril whose 1 to 4 methylol groups are acyloxymethylated or a mixture of them. Illustrative example of the urea compound includes tetramethylol urea, tetramethoxy methyl urea, tetramethylol urea whose 1 to 4 methylol groups are methoxymethylated or a mixture of them, and tetramethoxy ethyl urea.

Illustrative example of the isocyanate compound includes tolylene diisocyanate, diphenylmethane diisocyanate, hexamethylene diisocyanate, and cyclohexane diisocyanate. Illustrative example of the azide compound includes 1,1'-biphenyl-4,4'-bisazide, 4,4'-methylidenebisazide, and 4,4'-oxybisazide.

Illustrative example of the compound having an alkenyl ether group includes ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, and sorbitol pentavinyl ether.

As mentioned above, the biological electrode composition of the present invention can form the living body contact layer for a biological electrode which can efficiently convert the change in the ion concentration from a skin to an electric signal thereby transmitting this signal to a device (namely, this is excellent in the conductivity), which hardly causes an allergy even if it is attached to a skin for a long period of time (namely, this is excellent in the biocompatibility) because the ionic component of the polymer compound does not penetrate into a skin, which does not cause a decrease in the conductivity thereof by sweat or washing because the ionic component is not extracted even when it is contacted to water, and which is light in the weight thereof and producible at a low cost; and in addition, it can be a biological electrode composition also having a function as an adhesive. Further, when a carbon material or a particle coated with a noble metal is added thereto, the conductivity can be enhanced furthermore and the biological electrode having high adhesiveness and elasticity can be produced. In addition, by appropriately controlling the composition of the polymer compound or the thickness of the living body contact layer, the elasticity and the adhesiveness may also be controlled.

<Biological Electrode>

In addition, the present invention provides a biological electrode having a conductive substrate and a living body contact layer formed on the conductive substrate, wherein the living body contact layer is a cured product of the biological electrode composition of the present invention.

Hereunder, the biological electrode of the present invention will be explained in detail with referring to the drawings; but the present invention is not limited to these.

FIG. 1 is a rough cross section view illustrating one example of the biological electrode of the present invention. The biological electrode 1 of FIG. 1 has the conductive substrate 2 and the living body contact layer 3 formed on the conductive substrate 2. The living body contact layer 3 is a layer in which the carbon material 4 is dispersed in the polymer compound (resin) 5.

Figure 2:
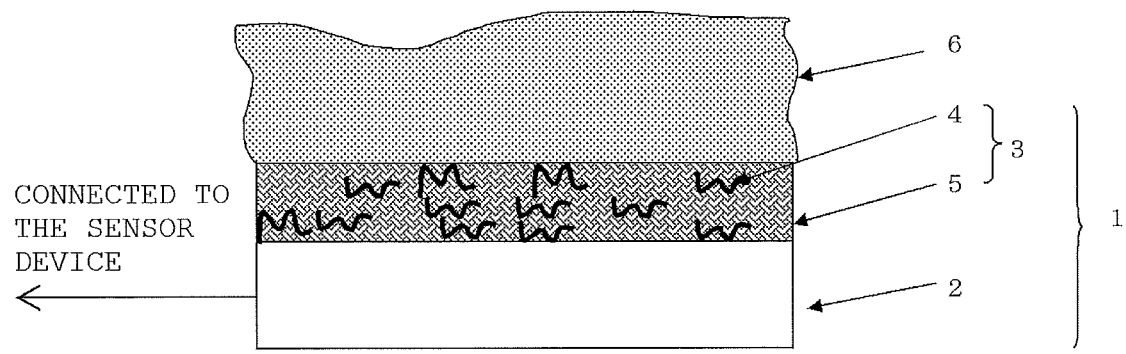
FIG. 2 is a rough cross section view illustrating one example that the biological electrode of the present invention is attached to a living body.

As illustrated in FIG. 2, when the biological electrode 1 shown in FIG. 1 is used, the living body contact layer 3 (namely, the layer in which the carbon material 4 is dispersed in the polymer compound 5) is contacted to the living body 6 thereby taking out an electric signal from the living body 6 by the polymer compound 5 and the carbon material 4; and then, this signal is transmitted to a sensor device or the like (not shown in the drawing) via the conductive substrate 2. When the biological electrode of the present invention is configured in the way as mentioned above, both the conductivity and the biocompatibility can be satisfied at the same time due to the polymer compound; and when the conductivity enhancer such as the carbon material is added as needed, the conductivity can be enhanced furthermore, and in addition, the contact area with a skin is constant because it has an adhesive property, so that the electric signal from a skin can be obtained stably with a high sensitivity.

Hereunder, each component material of the biological electrode of the present invention will be explained in more detail.

[Conductive Substrate]

The biological electrode of the present invention has a conductive substrate. Usually this conductive substrate is electrically connected to a sensor device or the like so as to transmit an electric signal taken out from a living body via the living body contact layer to the sensor device or the like.

The conductive substrate is not particularly restricted so far as it has conductivity, while it is preferable to contain one or more substances selected from, for example, gold, silver, silver chloride, platinum, aluminum, magnesium, tin, tungsten, iron, copper, nickel, stainless steel, chromium, titanium, and carbon.

Again, the conductive substrate is not particularly restricted; and thus, it may be a hard conductive substrate and so forth, a conductive film having flexibility, a cloth having a conductive paste coated on the surface thereof, or a cloth having a conductive polymer kneaded thereinto. The conductive substrate may be flat or rough in the surface thereof, or in a form of weaved mesh of metal wires. Therefore, the conductive substrate may be arbitrarily chosen in accordance with the use or the like of the biological electrode.

[Living Body Contact Layer]

The biological electrode of the present invention has a living body contact layer formed on the conductive substrate. This living body contact layer is a portion which actually contacts to a living body when the biological electrode is used, wherein it has conductivity as well as adhesiveness. The living body contact layer is a cured product of the biological electrode composition of the present invention as mentioned above, namely, the living body contact layer is an adhesive resin layer including the polymer compound having the adhesive function as mentioned before as well as an additive such as the carbon material as needed.

Meanwhile, the adhesion strength of the living body contact layer is preferably 0.1 N/25-mm or more and 20 N/25-mm or less. With regard to the measurement method of the adhesion strength, the method stipulated in JIS Z 0237 is generally used, wherein as the substrate, a metal substrate such as SUS (stainless steel) or a PET (polyethylene terephthalate) substrate may be used; however, a human skin may also be used in the measurement. The surface energy of a human skin is lower than that of a metal or various plastics, and is almost as low as Teflon (registered trade name), so that it is hard to be adhered in nature.

Thickness of the living body contact layer of the biological electrode is preferably 0.1 μm or more and 5 mm or less, while more preferably 0.2 μm or more and 3 mm or less. When the living body contact layer becomes thinner, the adhesion strength decreases, but the flexibility thereof increases and the weight thereof becomes lighter; and thus, the fitting thereof to a skin becomes better. The thickness of the living body contact layer can be chosen by taking a balance of the adhesiveness and the feeling to a skin into an account.

In addition, in the biological electrode of the present invention, similarly to conventional biological electrodes (for example, the biological electrode described in Japanese Patent Laid-Open Publication No. 2004-033468), an adhesive film may be separately arranged on the living body contact layer so as to avoid peel-off of the biological electrode from a living body while it is used. In the case that the adhesive film is separately arranged, the adhesive film may be formed by using an adhesive film material of an acryl type, a urethane type, a silicone type, or the like, wherein the silicone type is preferable not only because cutaneous respiration is possible while it is attached to a skin because of an especially high oxygen permeability thereof but also because the decrease in adhesiveness due to sweat is small due to a high water-repellent property thereof as well as a skin irritation is low. Meanwhile, as mentioned above, the biological electrode of the present invention can avoid a peel-off from a living body by adding a tackifier to the biological electrode composition or by using the polymer compound having a good adhesiveness to a living body; and thus, the separate adhesive film mentioned above is not necessarily required.

Upon using the biological electrode of the present invention as a wearable device, wiring of the biological electrode to the sensor device and other members are not particularly restricted, whereby, for example, those described in Japanese Patent Laid-Open Publication No. 2004-033468 may be used.

As mentioned above, because the biological electrode of the present invention forms the living body contact layer by the cured product of the biological electrode composition of the present invention, it can be the biological electrode which can efficiently transmit an electric signal from a skin to a device (namely, this is excellent in the conductivity), which hardly causes an allergy even if it is attached to a skin for a long period of time (namely, this is excellent in the biocompatibility), which is light in the weight thereof and producible at a low cost, and which does not cause a significant decrease in the conductivity thereof regardless of under a water-wet condition and a dry condition. In addition, when the carbon material is added thereto, the conductivity thereof can be further enhanced; and when the polymer compound having adhesiveness and elasticity is combined therewith, the biological electrode having especially high adhesiveness and elasticity can be produced. Further, the elasticity and adhesiveness to a skin can be improved with an additive and so forth; and in addition, by appropriately controlling the composition of the polymer compound or the thickness of the living body contact layer, the elasticity and the adhesiveness thereof can also be controlled. Accordingly, the biological electrode of the present invention as mentioned above is especially suitable as the biological electrode to be used in a wearable device for medical treatment.

<Method for Producing the Biological Electrode>

In addition, the present invention provides a method for producing a biological electrode, which is a method for producing a biological electrode having a conductive substrate and a living body contact layer formed on the conductive substrate, wherein the method comprises application of the biological electrode composition of the present invention as mentioned above on the conductive substrate followed by curing the composition to form the living body contact layer.

Meanwhile, the conductive substrate, the biological electrode composition, and so forth to be used in the method for producing the biological electrode of the present invention may be the same as those described before.

The method for applying the biological electrode composition onto the conductive substrate is not particularly restricted, wherein illustrative example of the method suitably usable therein includes a dip coating method, a spray coating method, a spin coating method, a roll coating method, a flow coating method, a doctor coating method, a screen printing method, a flexo printing method, a gravure printing method, and an ink jet printing method.

The method for curing the polymer compound is not particularly restricted; and thus, the method may be arbitrarily chosen in accordance with the polymer compound to be used in the biological electrode composition. The polymer compound is preferably cured, for example, by any one or both of a heat and a light. Alternatively, a catalyst capable of generating an acid or a base may be added into the biological electrode composition so as to generate a cross-linking reaction to cause the curing.

Meanwhile, the temperature in the case of heating is not particularly restricted; and thus, the temperature may be arbitrarily chosen in accordance with the polymer compound to be used in the biological electrode composition. For example, the temperature is preferably about 50 to 250° C.

When heating and light irradiation are combined, heating and light irradiation may be carried out at the same time, or heating may be carried out after light irradiation, or light irradiation may be carried out after heating. In addition, in order to evaporate the solvent after application, drying by a wind may be carried out before heating.

As mentioned above, according to the method for producing the biological electrode of the present invention, the biological electrode of the present invention which is excellent in conductivity and biocompatibility, as well as light in the weight thereof, and in addition, which does not cause a significant decrease in the conductivity thereof regardless of under a water-wet condition and a dry condition can be easily produced at a low cost.

EXAMPLE

Hereunder, the present invention will be specifically explained by using Synthesis Examples, Comparative Synthesis Examples, Examples, and Comparative Examples; however, the present invention is not limited to them.

Synthesis Example 1

Synthesis of Polymerizable Monomer (Monomer 1)

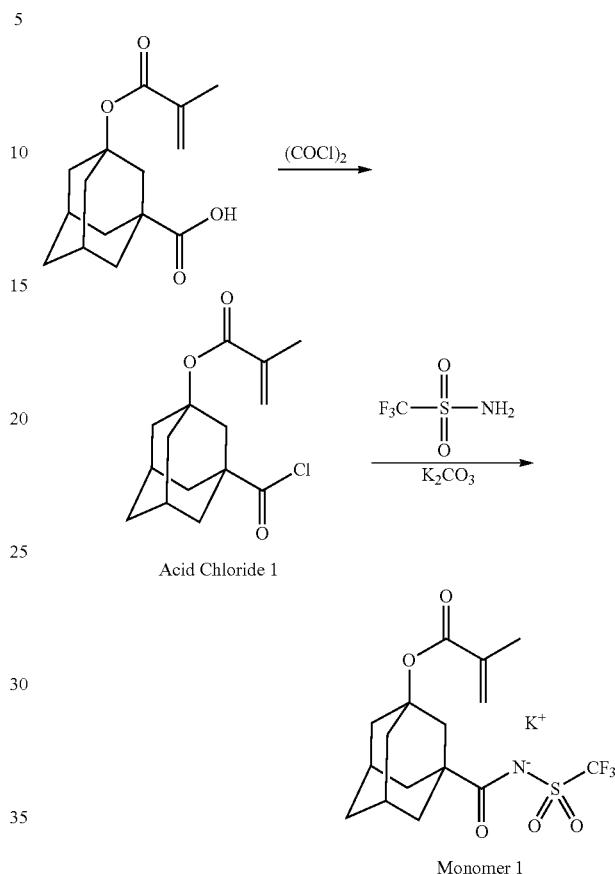

Acid Chloride 1

Monomer 1

After a mixed solution of 17.2 g of 3-(2-methylacryloyloxy)adamantane-1-carboxylic acid and 100 g of toluene was heated to 40° C., 9.5 g of oxalyl chloride was dropwisely added to the mixed solution. After completion of the dropwise addition, the temperature of the resulting solution was raised to 50° C.; and after stirring for 5 hours, it was condensed under reduced pressure to remove residual oxalyl chloride and the solvent to obtain 19.3 g of Acid Chloride 1.

Next, after a mixed solution of 7.5 g of trifluoromethane sulfonamide, 9.0 g of potassium carbonate, and 60 g of acetonitrile was cooled in an ice bath, to this solution was dropwisely added a mixed solution of 19.3 g of Acid Chloride 1 and 30 g of acetonitrile while cooling the solution in an ice bath. After the temperature of this resulting mixture was raised to room temperature, it was stirred for 22 hours. After completion of the reaction was confirmed with NMR, the reaction solution was cooled in an ice bath and the reaction was stopped by adding 150 g of pure water to it. The reaction solution was extracted twice with 100 g of methylene chloride; and then, the organic layer thus obtained was washed with 100 g of pure water for 3 times. After this layer was concentrated under reduced pressure, it was added with 100 g of diisopropyl ether, and then the resulting mixture was stirred. The separated solid was collected by filtration and dried under reduced pressure to obtain 13.5 g of the intended Monomer 1 (yield of 59%).

The measurement results of $^1$H-NMR and $^{19}$F-NMR of the Monomer 1 thus obtained are as follows.

$^1$H-NMR (500 MHz in DMSO-d6): δ=1.53 (2H, m), 1.63 (4H, m), 1.81 (3H, s), 1.96 to 2.07 (6H, m), 2.17 (2H, s), 5.56 (1H, m), and 5.91 (1H, m) ppm.

$^{19}$F-NMR (500 MHz in DMSO-d6): δ=−78.6 (3F, s).

Synthesis Example 2

Synthesis of Polymer Compound (Polymer)]

The polymer compound (Polymer) to be blended into the biological electrode composition solution was synthesized with the prescription described below.

Synthesis Examples 2-1 to 2-14

Syntheses of Ionic Polymers 1 to 14

After the PGMEA (propyleneglycol-1-monomethylether-2-acetate) solution containing 30% by mass of respective monomers was mixed in a reaction vessel, this solution was cooled to −70° C. under a nitrogen atmosphere; and then degassing under reduced pressure and blowing of nitrogen were repeated for 3 times. After the temperature thereof was raised to room temperature, AIBN (azobisisobutyronitrile) was added thereto as the polymerization initiator with the amount of 0.01 mole relative to 1 mole of total monomers; and then, after the temperature of the resulting mixture was raised to 60° C., the reaction was carried out for 15 hours to obtain a solution containing polymer (Ionic Polymer Solutions 1 to 14). Composition of the obtained polymer was confirmed with $^1$H-NMR after drying to remove the solvent; and the molecular weight (Mw) and the dispersibility (Mw/Mn) of the obtained polymer were confirmed with GPC using THF as the solvent.

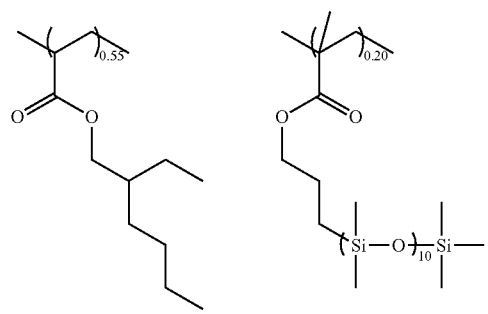

Ionic Polymer 1

Mw = 20,900
Mw/Mn = 2.21

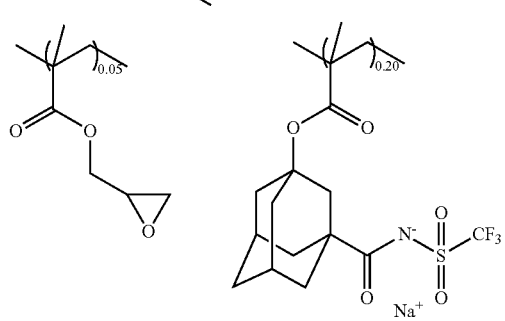

Ionic Polymer 2

Mw = 27,400
Mw/Mn = 1.94, wherein, the repeating numbers in the formula are average numbers.

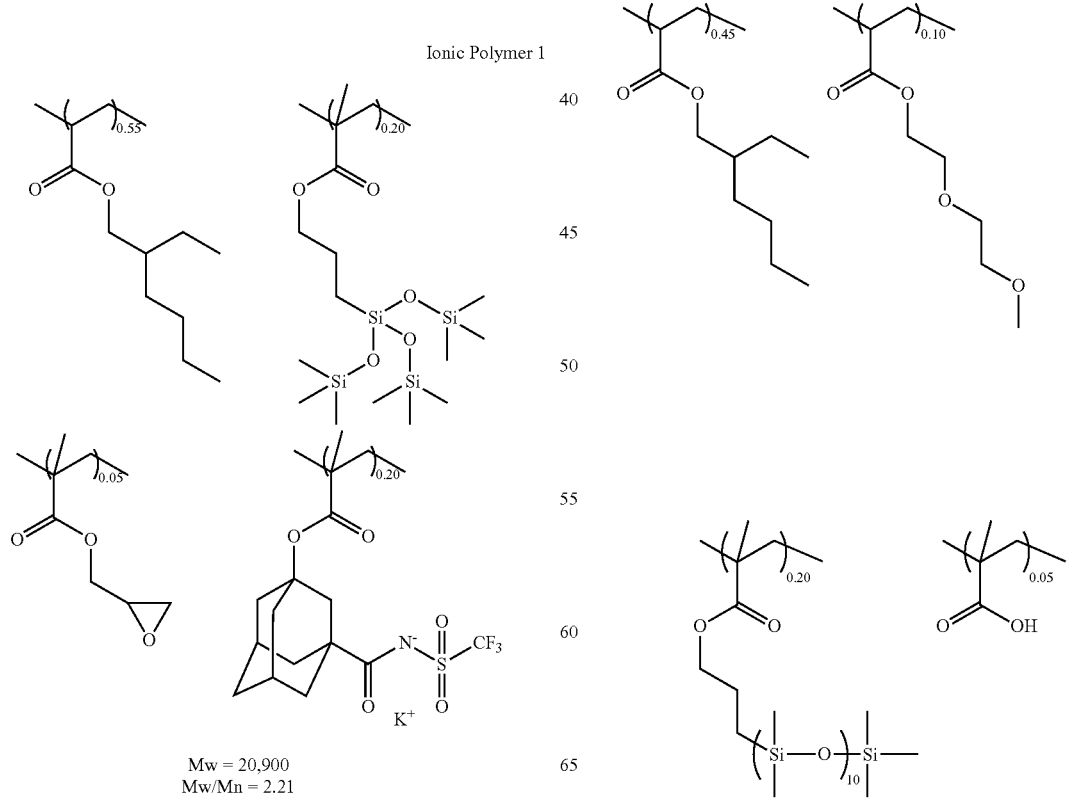

Ionic Polymer 3

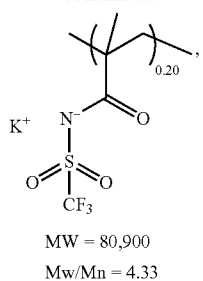
MW = 80,900
Mw/Mn = 4.33
wherein, the repeating numbers in the formula are average numbers.
Ionic Polymer 4
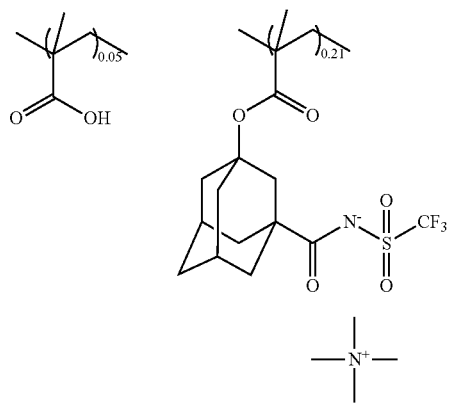
Mw = 26,600
Mw/Mn = 1.86,
wherein, the repeating numbers in the formula are average numbers.
Ionic Polymer 5
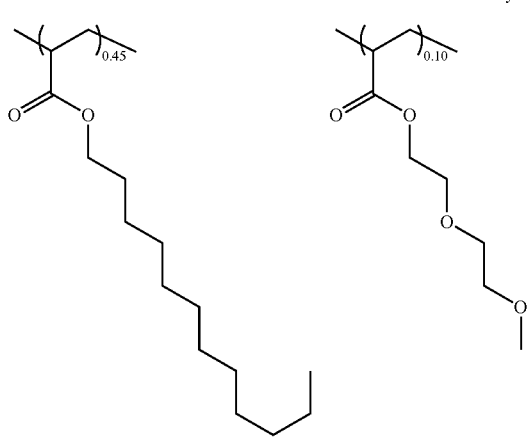
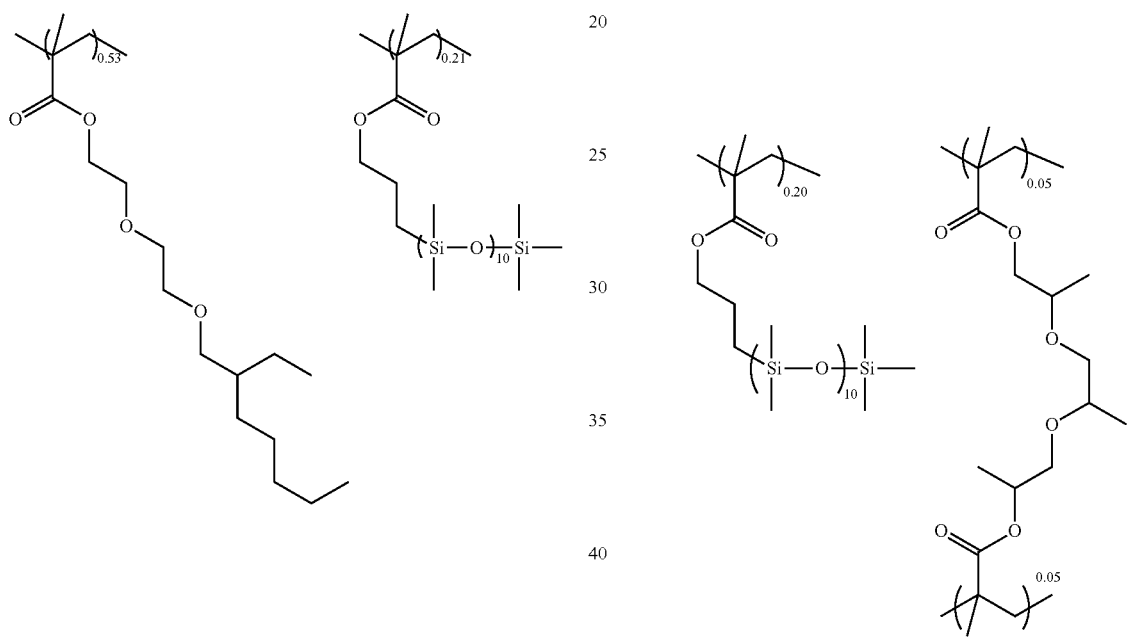
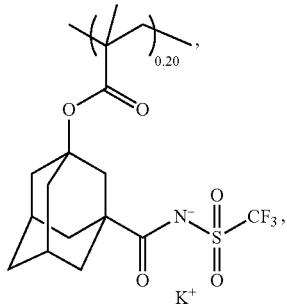
MW = 80,900
Mw/Mn = 4.33
wherein, the repeating numbers in the formula are average numbers.

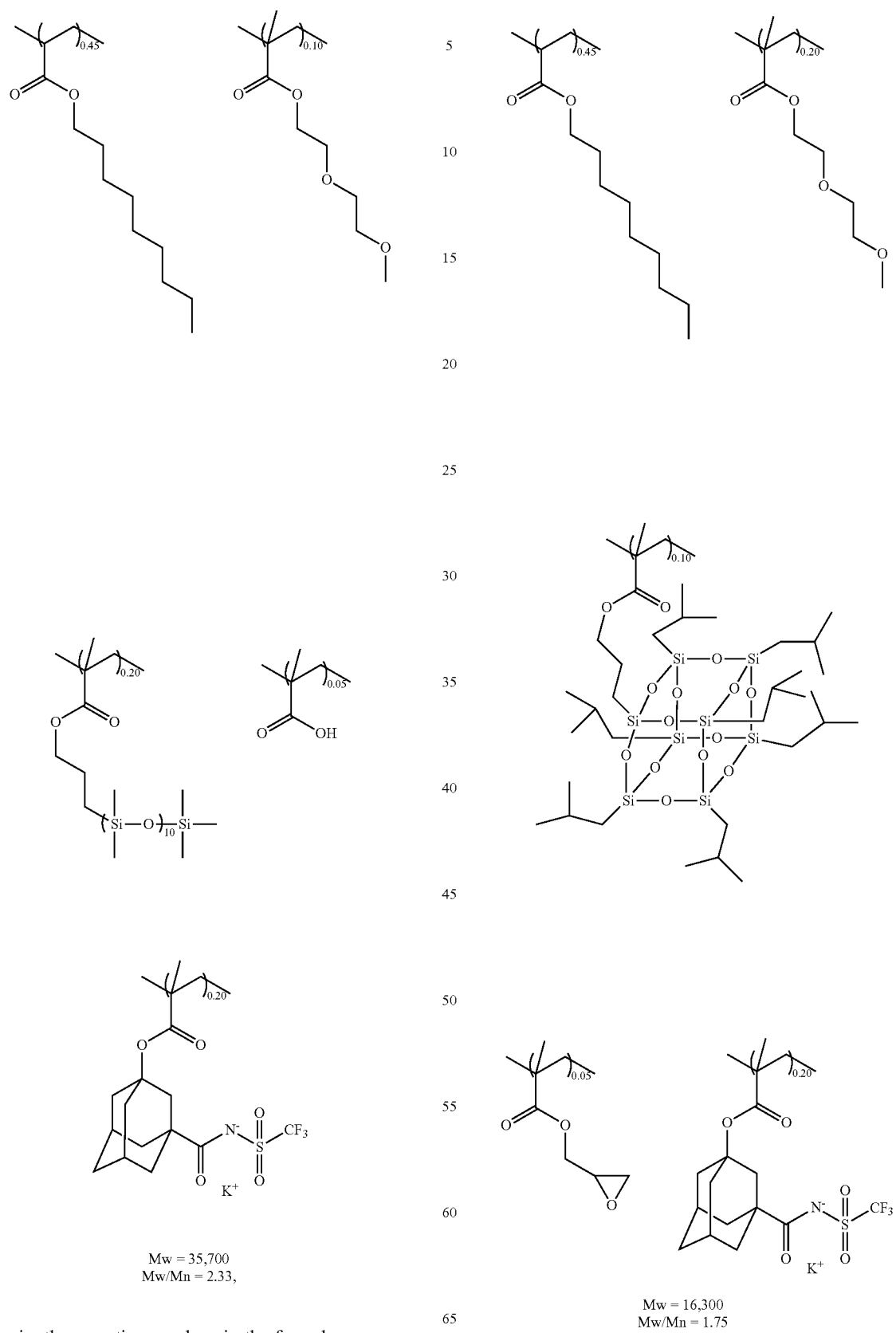
wherein, the repeating numbers in the formula are average numbers.

Ionic Polymer 8
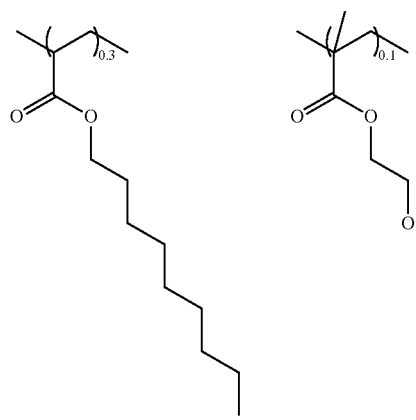
Mw = 49,300
Mw/Mn = 2.22,
wherein, the repeating numbers in the formula are average numbers.
Ionic Polymer 9
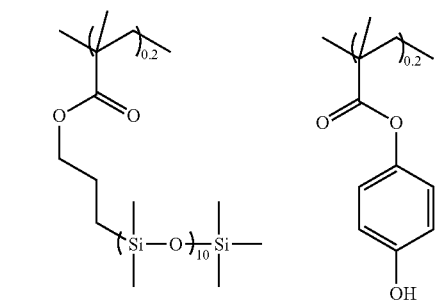
MW = 46,900
Mw/Mn = 1.90
wherein, the repeating numbers in the formula are average numbers.

Ionic Polymer 10
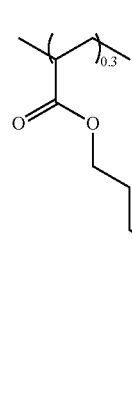 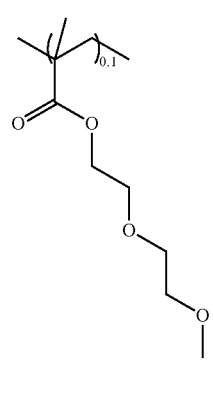
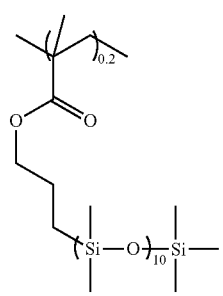 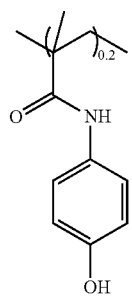 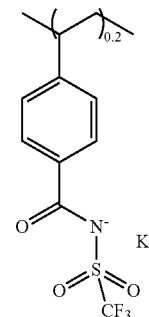
Mw = 46,900
Mw/Mn = 1.90,
wherein, the repeating numbers in the formula are average numbers.
Ionic Polymer 11
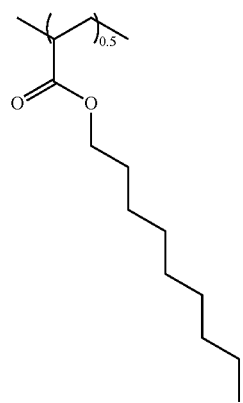 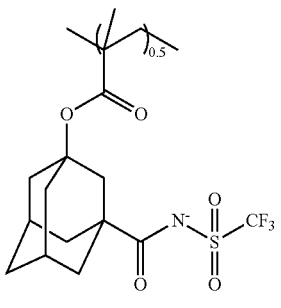
Mw = 57,300
Mw/Mn = 2.19
Ionic Polymer 12
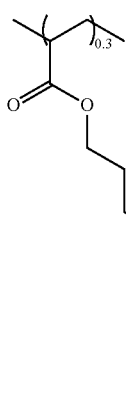 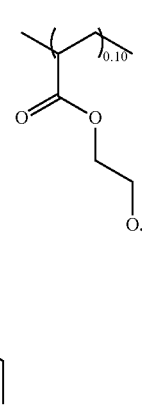
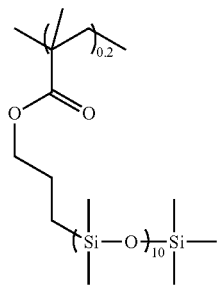 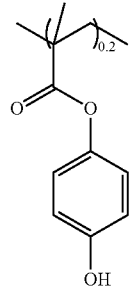
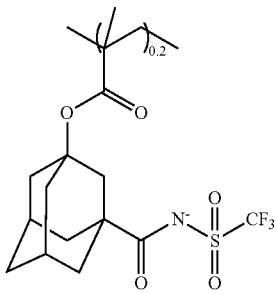
Mw = 41,300
Mw/Mn = 2.02,
wherein, the repeating numbers in the formula are average numbers.

Ionic Polymer 13

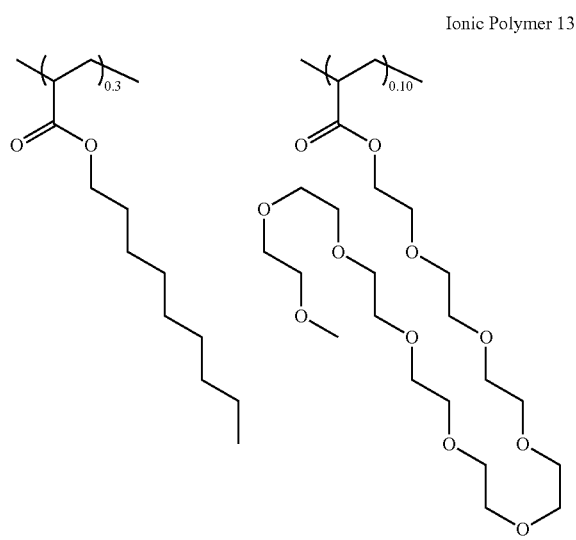

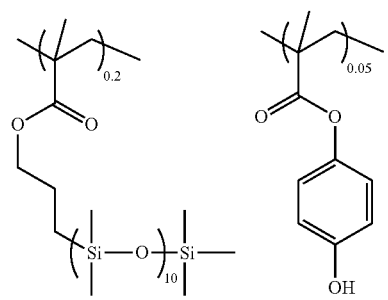

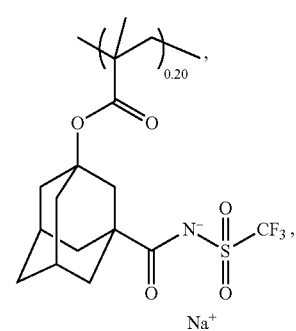

MW = 43,300
Mw/Mn = 1.98 wherein, the repeating numbers in the formula are average numbers.

Ionic Polymer 14

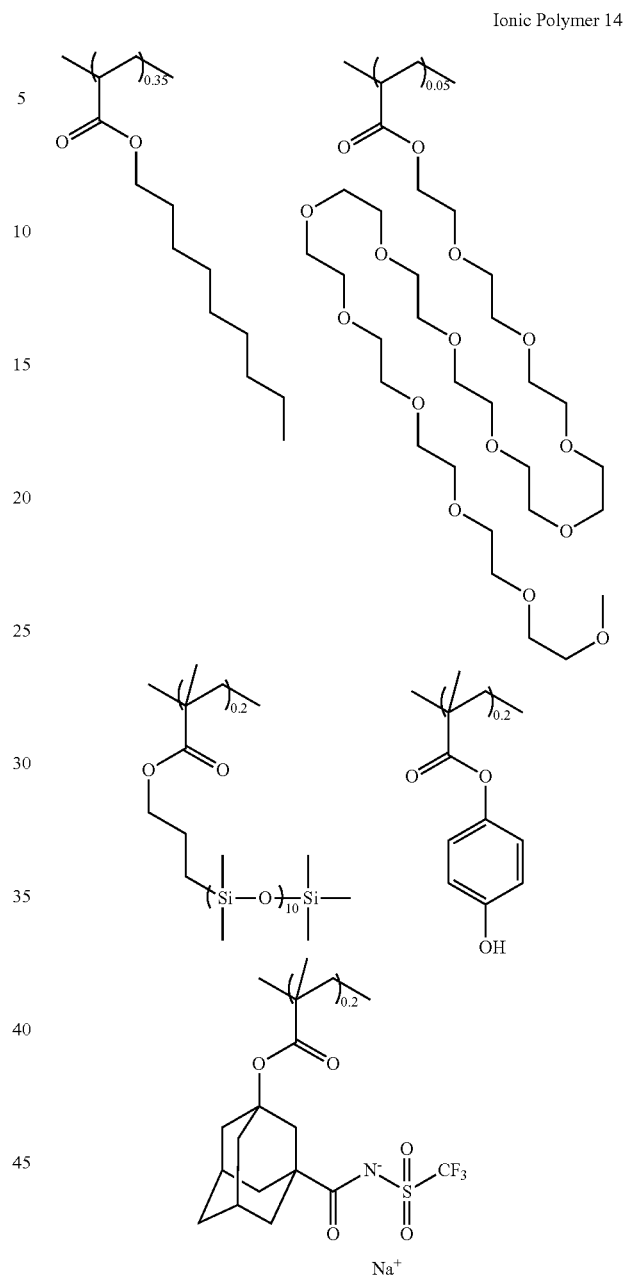

Mw = 40,900
Mw/Mn = 2.01, wherein, the repeating numbers in the formula are average numbers.

Comparative Synthesis Example 1

Synthesis of Comparative Polymer 1

Except that kinds and blending ratio of each monomer were changed, the same procedure as that of Synthesis Example 2-1 was repeated to obtain a solution containing Comparative Polymer 1 (Comparative Polymer Solution 1) shown below.

Comparative Polymer 1

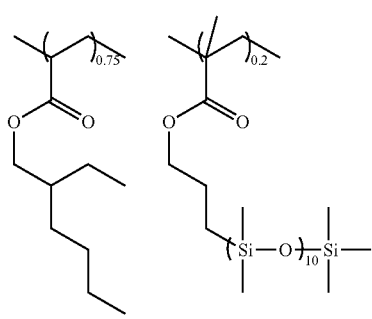

Mw = 116,000
Mw/Mn = 2.20, wherein, the repeating numbers in the formula are average numbers.

Comparative Synthesis Examples 2 and 3

Synthesis of Comparative Ionic Polymers 1 and 2

Except that kinds and blending ratio of each monomer were changed, the same procedure as that of Synthesis Example 2-1 was repeated to obtain each solution containing Comparative Ionic Polymers 1 and 2 (Comparative Ionic Polymer Solutions 1 and 2) shown below.

Comparative Ionic Polymer 1

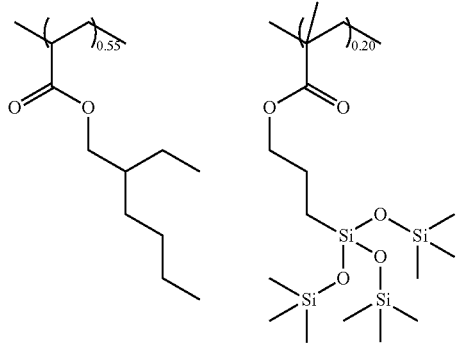

Mw = 44,900
Mw/Mn = 2.59

Comparative Ionic Polymer 2

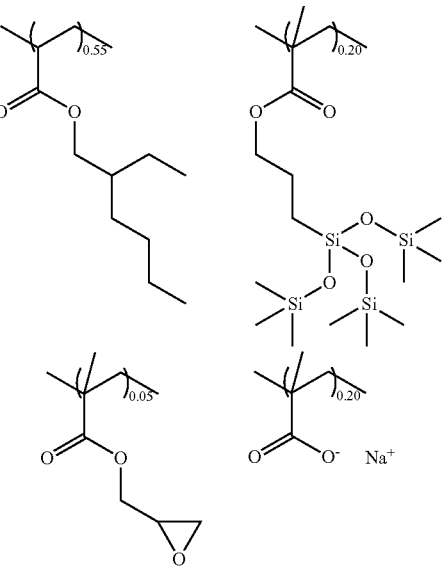

Mw = 57,900
Mw/Mn = 1.89

Examples 1 to 18 and Comparative Examples 1 to 5

By using the solutions containing polymer compounds obtained in Synthesis Examples 2-1 to 2-14 and Comparative Synthesis Examples 1 to 3, the respective polymer compound solutions, comparative salts, and additives were blended with the compositions described in Table 1 to obtain the respective biological electrode composition solutions (Biological Electrode Composition Solutions 1 to 18 and Comparative Biological Electrode Composition Solutions 1 to 5).

TABLE 1

| Biological Electrode Composition Solution | Polymer Compound Solution (part by mass) | Comparative Salt (parts by mass) | Additive (parts by mass) |
|---|---|---|---|
| Biological Electrode Composition Solution 1 | Ionic Polymer Solution 1 (10) | — | Carbon Black (0.3) |
| Biological Electrode Composition Solution 2 | Ionic Polymer Solution 2 (10) | — | Carbon Black (0.3) |
| Biological Electrode Composition Solution 3 | Ionic Polymer Solution 3 (10) | — | Carbon Black (0.3) |
| Biological Electrode Composition Solution 4 | Ionic Polymer Solution 4 (10) | — | Carbon Black (0.3) |
| Biological Electrode Composition Solution | Ionic Polymer | — | Carbon Black |

TABLE 1-continued

| Biological Electrode Composition Solution | Polymer Compound Solution (part by mass) | Comparative Salt (parts by mass) | Additive (parts by mass) |
|---|---|---|---|
| Solution 5 | Solution 5 (10) | | (0.3) |
| Biological Electrode Composition Solution 6 | Ionic Polymer Solution 6 (10) | — | Carbon Nanotube (0.2) |
| Biological Electrode Composition Solution 7 | Ionic Polymer Solution 7 (10) | — | Crosslinking Agent 1 (0.05) Carbon Black (0.3) |
| Biological Electrode Composition Solution 8 | Ionic Polymer Solution 1 (10) | — | Gold-Coated Particle (0.5) |
| Biological Electrode Composition Solution 9 | Ionic Polymer Solution 1 (10) | — | Silver-Coated Particle (0.5) |
| Biological Electrode Composition Solution 10 | Ionic Polymer Solution 1 (10) | — | ITO Particle (0.7) |
| Biological Electrode Composition Solution 11 | Ionic Polymer Solution 1 (10) | — | — |
| Biological Electrode Composition Solution 12 | Ionic Polymer Solution 8 (10) | — | Carbon Black (0.3) |
| Biological Electrode Composition Solution 13 | Ionic Polymer Solution 9 (10) | — | Carbon Black (0.3) |
| Biological Electrode Composition Solution 14 | Ionic Polymer Solution 10 (10) | — | Carbon Black (0.3) |
| Biological Electrode Composition Solution 15 | Ionic Polymer Solution 10 (5) Ionic Polymer Solution 11 (5) | — | Carbon Black (0.3) |
| Biological Electrode Composition Solution 16 | Ionic Polymer Solution 12 (10) | — | Carbon Black (0.3) |
| Biological Electrode Composition Solution 17 | Ionic Polymer Solution 13 (10) | — | Carbon Black (0.3) |
| Biological Electrode Composition Solution 18 | Ionic Polymer Solution 14 (10) | — | Carbon Black (0.3) |
| Comparative Biological Electrode Composition Solution 1 | Comparative Polymer Solution 1 (10) | Comparative Salt 1 (0.3) | Carbon Black (0.3) |
| Comparative Biological Electrode Composition Solution 2 | Comparative Polymer Solution 1 (10) | Comparative Salt 2 (0.3) | Carbon Black (0.3) |
| Comparative Biological Electrode Composition Solution 3 | Comparative Polymer Solution 1 (10) | Comparative Salt 3 (0.3) | Carbon Black (0.3) |
| Comparative Biological Electrode Composition Solution 4 | Comparative Ionic Polymer Solution 1 (10) | — | Carbon Black (0.3) |
| Comparative Biological Electrode Composition Solution 5 | Comparative Ionic Polymer Solution 2 (10) | — | Carbon Black (0.3) |

Structures of Comparative Salts 1 to 3 that were blended to the biological electrode composition solutions are shown below.

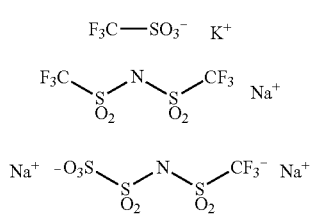

Comparative Salt 1
Comparative Salt 2
Comparative Salt 3

The structure of Crosslinking Agent 1 that was blended as the additive to the biological electrode composition solutions is shown below.

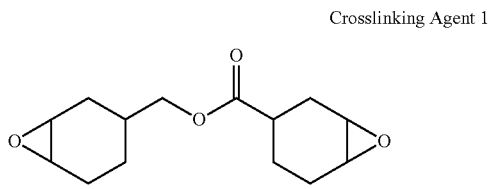

Crosslinking Agent 1

The conductivity enhancers (carbon black, carbon nanotube, gold-coated particle, silver-coated particle, and ITO particle) that were blended as the additive to the biological electrode composition solutions are shown below.

Carbon black: Denka Black HS-100 (manufactured by Denka Co., Ltd.)
Carbon nanotube: Multi-walled, diameter of 60 to 100 nm, and length of 5 μm (manufactured by Sigma-Aldrich, Inc.) Gold-coated particle: Micro Pearle AU, diameter of 100 μm (manufactured by Sekisui Chemical Co., Ltd.)
Silver-coated particle: Silver-coated powder, diameter of 30 μm (manufactured by Mitsubishi Material Corp.)
ITO particle: ITO powder, diameter of 0.03 μm (manufactured by Mitsubishi Material Corp.)

(Evaluation of Conductivity)

Figure 3:
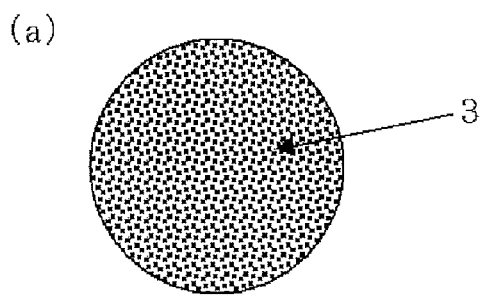
FIG. 3 is (a) a rough drawing of the biological electrode produced in Example of the present invention that is viewed from the side of the living body contact layer and (b) a rough drawing of the same that is viewed from the side of the conductive substrate.
Figure 3:
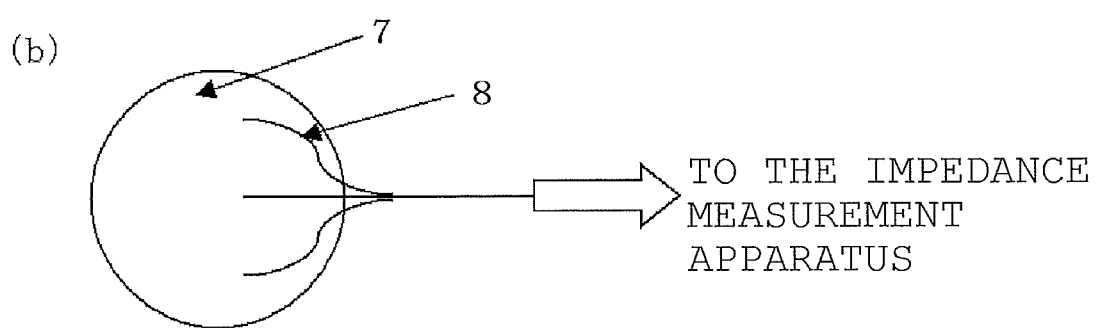
Figure 4:
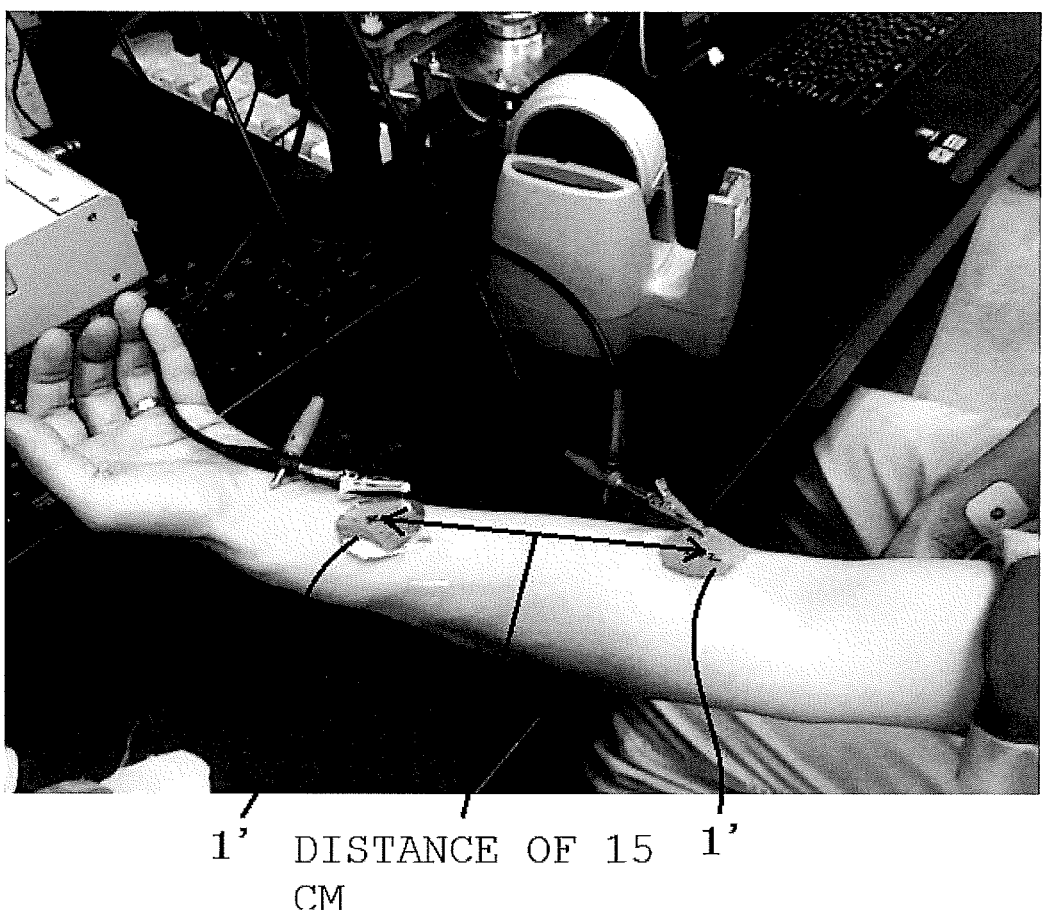
FIG. 4 is a picture of the impedance measurement on a skin surface by using the biological electrode produced in Example of the present invention.

The biological electrode composition solution was applied by using an applicator onto an aluminum-made disk having a diameter of 3 cm and a thickness of 0.2 mm; and after it was dried by a wind at room temperature for 6 hours, it was cured by baking in an oven at 130° C. under a nitrogen atmosphere for 30 minutes to obtain 4 sheets of the biological electrodes for each biological electrode composition solution. The biological electrode obtained in the way as described above had the living body contact layer 3 on one surface and the aluminum-made disk 7 as the conductive substrate on the other surface, as illustrated in FIG. 3(*a*) and FIG. 3(*b*). Next, as illustrated in FIG. 3(*b*), the copper wire 8 was adhered by using an adhesive tape onto a surface of the aluminum-made disc 7, i.e., the surface not covered with the living body contact layer, thereby making it the takingout electrode; and then, this electrode was connected to an impedance measurement apparatus. Next, as illustrated in FIG. 4, two sheets of the biological electrode 1' were adhered such that the skin of a human arm may contact to the side of the living body contact layer with the distance of 15 cm between the two sheets. Then, the initial impedance was measured with changing the frequency by using an AC impedance measurement apparatus SI 1260 (Manufactured by Solarton Group, Ltd.). Next, remaining two sheets of the biological electrode were immersed in pure water for 1 hour, and dried to remove water; and then, the impedance on the skin was measured in the same way as before. The impedances at the frequency of 1,000 Hz are summarized in Table 2.

(Evaluation of Adhesiveness)

The biological electrode composition solution was applied by using an applicator onto a PEN (polyethylene naphthalate) substrate having a thickness of 100 μm; and after it was dried by a wind at room temperature for 6 hours, it was cured by baking in an oven at 130° C. under a nitrogen atmosphere for 30 minutes to obtain an adhesive film. From this adhesive film, a tape having a wideness of 25 mm was cut out and press-adhered to a stainless steel plate (SUS 304). After this was allowed to stand at room temperature for 20 hours, the force (N/25-mm) to peel-off the tape attached with the adhesive from the stainless steel plate (SUS 304) was measured by using a tension testing instrument with the angle of 180 degrees and the rate of 300 mm/minute. The measurement results of the tests are summarized in Table 2.

(Measurement of Thickness of the Living Body Contact Layer)

With regard to the biological electrode obtained in the evaluation test of the conductivity as mentioned above, the thickness of the living body contact layer thereof was measured by using a micrometer. The measurement results of the tests are summarized in Table 2.

TABLE 2

|  | Biological Electrode Composition Solution | Adhesion Strength (N/25-mm) | Living Body Contact Layer Thickness (μm) | Initial Impedance (Ω) | Inpedance after Water Immersion (Ω) |
|---|---|---|---|---|---|
| Example 1 | Biological Electrode Composition Solution 1 | 1.6 | 150 | $8.6E^2$ | $7.1E^2$ |
| Example 2 | Biological Electrode Composition Solution 2 | 1.8 | 133 | $7.6E^2$ | $7.4E^2$ |
| Example 3 | Biological Electrode Composition Solution 3 | 1.1 | 150 | $4.8E^2$ | $4.1E^2$ |
| Example 4 | Biological Electrode Composition Solution 4 | 2.0 | 130 | $9.2E^2$ | $8.9E^2$ |
| Example 5 | Biological Electrode Composition Solution 5 | 2.9 | 160 | $3.2E^2$ | $3.6E^2$ |
| Example 6 | Biological Electrode Composition Solution 6 | 2.5 | 170 | $4.6E^2$ | $4.3E^2$ |
| Example 7 | Biological Electrode Composition Solution 7 | 1.3 | 160 | $1.8E^3$ | $1.9E^3$ |
| Example 8 | Biological Electrode Composition Solution 8 | 1.6 | 150 | $7.6E^3$ | $8.1E^3$ |
| Example 9 | Biological Electrode Composition Solution 9 | 1.9 | 120 | $8.8E^3$ | $7.9E^3$ |
| Example 10 | Biological Electrode Composition Solution 10 | 1.9 | 250 | $3.2E^3$ | $3.3E^3$ |
| Example 11 | Biological Electrode Composition Solution 11 | 2.6 | 160 | $7.4E^3$ | $8.8E^3$ |
| Example 12 | Biological Electrode Composition Solution 12 | 1.6 | 150 | $8.6E^2$ | $7.1E^2$ |
| Example 13 | Biological Electrode Composition Solution 13 | 1.8 | 133 | $7.6E^2$ | $7.4E^2$ |
| Example 14 | Biological Electrode Composition Solution 14 | 1.1 | 150 | $4.8E^2$ | $4.1E^2$ |
| Example 15 | Biological Electrode Composition Solution 15 | 2.0 | 130 | $9.2E^2$ | $8.9E^2$ |
| Example 16 | Biological Electrode Composition Solution 16 | 1.6 | 146 | $6.6E^2$ | $5.4E^2$ |
| Example 17 | Biological Electrode Composition Solution 17 | 1.3 | 157 | $3.8E^2$ | $4.1E^2$ |
| Example 18 | Biological Electrode Composition Solution 18 | 1.0 | no | $2.2E^2$ | $2.9E^2$ |
| Comparative Example 1 | Comparative Biological Electrode Composition Solution 1 | 2.3 | 120 | $2.2E^4$ | $5.3E^5$ |
| Comparative Example 2 | Comparative Biological Electrode Composition Solution 2 | 2.2 | 130 | $3.2E^4$ | $7.3E^5$ |
| Comparative Example 3 | Comparative Biological Electrode Composition Solution 3 | 1.6 | 120 | $1.2E^4$ | $9.3E^5$ |
| Comparative Example 4 | Comparative Biological Electrode Composition Solution 4 | 4.5 | 140 | $2.9E^7$ | $1.9E^7$ |
| Comparative Example 5 | Comparative Biological Electrode Composition Solution 5 | 4.5 | 140 | $7.9E^7$ | $8.9E^7$ |

As can be seen in Table 2, in Examples 1 to 18 in which the living body contact layer was formed by using the biological electrode composition of the present invention in which the polymer compound having a specific structure was blended, the initial impedance was low; and even after it was immersed in water and dried, the impedance did not change. Namely, in Examples 1 to 18, the biological electrode which has a high initial conductivity and does not significantly change the conductivity when it is wetted with water and then dried could be obtained. In addition, the biological electrode like this in Examples 1 to 18 has the adhesion strength almost as high as the biological electrodes of Comparative Examples 1 to 5; and in addition, it is light in the weight thereof, excellent in biocompatibility, and producible at a low cost.

On the other hand, in Comparative Examples 1 to 3 in which the living body contact layer is formed by using the biological electrode composition that is blended with the comparative salt and the polymer compound not having the repeating unit "a", the initial impedance was low, but after it was immersed into water and then dried, an increase in the impedance so large as to give almost a different digit was observed. Namely, in Comparative Examples 1 to 3, only the biological electrode whose conductivity was significantly decreased after it was wet with water and then dried was obtained although the initial conductivity thereof was high.

In Comparative Examples 4 and 5 in which the polymer compound not copolymerized with the salt of sulfonamide having a nitrogen atom sandwiched between a fluoroalkyl sulfonyl group on one side and a carbonyl group on another side (namely the polymer compound not having the repeating unit "a") was used, the initial impedance was high. Namely, in Comparative Example 4 and 5, only the biological electrode having a low initial conductivity was obtained.

As mentioned above, in the biological electrode formed with the living body contact layer by using the biological electrode composition of the present invention, it became clear that conductivity, biocompatibility, and adhesiveness to the conductive substrate are excellent, and that because of excellent holding power of the conductive material the conductivity does not significantly decrease even if it is wet to water and then dried, and that it is light in the weight thereof and producible at a low cost.

Meanwhile, the present invention is not limited to the embodiments described above. The above embodiments are just examples; and thus, any embodiment having substantially the same composition and effect as those of the technological idea described in Claims of the present invention is included in the technological scope of the present invention.

EXPLANATION OF NUMERAL SYMBOLS 1 and 1': Biological electrode
2: Conductive substrate
3: Living body contact layer
4: Carbon material
5: Polymer compound (resin)
6: Living body
7: Aluminum-made disc
8: Copper wire

What is claimed is:

1. A polymerizable monomer represented by following general formula (1),

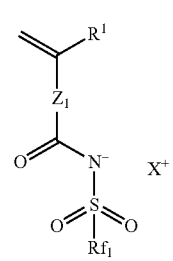

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

2. A polymer compound having a repeating unit represented by following general formula (2) and a weight average molecular weight of 500 or more,

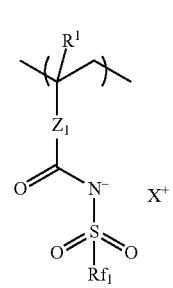

wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^1$ represents a hydrogen atom or a methyl group; $Z_1$ represents a single bond, an arylene group having 6 to 12 carbon atoms, or a group of —C(=O)—O—$R^2$—; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein.

3. A biological electrode composition comprising a polymer compound having both an ionic repeating unit "a" and a (meth)acrylate repeating unit "b", wherein the ionic repeating unit "a" is a repeating unit having a partial structure of a sodium salt, a potassium salt, or an ammonium salt, as represented by following general formula (3), and the (meth)acrylate repeating unit "b" is a repeating unit represented by following general formula (4),

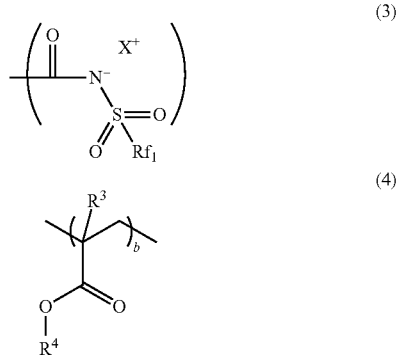

and wherein, $Rf_1$ represents a linear or a branched alkyl group having 1 to 4 carbon atoms and includes one or more fluorine atoms; $X^+$ represents any of a sodium ion, a potassium ion, and an ammonium ion; $R^3$ represents a hydrogen atom or a methyl group; $R^4$ represents a linear, a branched, or a cyclic alkyl group having 1 to 39 carbon atoms, or a linear, a branched, or a cyclic alkenyl group having 2 to 30 carbon atoms, or a linear, a branched, or a cyclic alkynyl group having 2 to 30 carbon atoms, or a phenyl group, or a naphthyl group, and wherein, when $R^4$ is the alkyl group, the alkenyl group, or the alkynyl group, $R^4$ may contain a hydroxy group, an ether group, an ester group, or an aromatic group therein; and $0<a<1.0$, $0<b<1.0$, and, $0<a+b\le1.0$.

4. The biological electrode composition according to claim 3, wherein the repeating unit "a" is a repeating unit a1 represented by following general formula (2'),

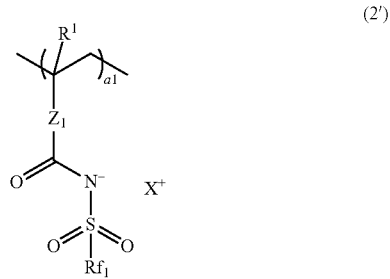

and wherein, $Rf_1$ and $X^+$ represent the same groups as those mentioned before; $R^1$ represents a hydrogen atom or a methyl group; $Z_1$ represents a single bond, an arylene group having 6 to 12 carbon atoms, or a group of $-C(=O)-O-R^2-$; $R^2$ represents a linear, a branched, or a cyclic alkylene group having 1 to 12 carbon atoms, or a divalent aromatic hydrocarbon group having 6 to 10 carbon atoms, and wherein, $R^2$ may contain an ether group, a carbonyl group, or an ester group therein; and $0<a1<1.0$.

5. The biological electrode composition according to claim 3, wherein the polymer compound is a copolymerized polymer compound further having, in addition to the repeating unit "a" and the repeating unit "b", any one or both of a repeating unit "c" having a fluorine atom or a silicon atom and a repeating unit "d" having one or more groups selected from a hydroxy group, a carboxyl group, an oxirane group, and an oxetane group.

6. The biological electrode composition according to claim 4, wherein the polymer compound is a copolymerized polymer compound further having, in addition to the repeating unit "a" and the repeating unit "b", any one or both of a repeating unit "c" having a fluorine atom or a silicon atom and a repeating unit "d" having one or more groups selected from a hydroxy group, a carboxyl group, an oxirane group, and an oxetane group.

7. The biological electrode composition according to any one of claim 3, wherein the biological electrode composition further contains a carbon material, an ITO particle, or a particle coated with a metal selected from silver, gold, platinum, copper, and nickel.

8. The biological electrode composition according to any one of claim 4, wherein the biological electrode composition further contains a carbon material, an ITO particle, or a particle coated with a metal selected from silver, gold, platinum, copper, and nickel.

9. The biological electrode composition according to any one of claim 5, wherein the biological electrode composition further contains a carbon material, an ITO particle, or a particle coated with a metal selected from silver, gold, platinum, copper, and nickel.

10. The biological electrode composition according to any one of claim 6, wherein the biological electrode composition further contains a carbon material, an ITO particle, or a particle coated with a metal selected from silver, gold, platinum, copper, and nickel.

11. The biological electrode composition according to claim 7, wherein the carbon material is any one or both of a carbon black and a carbon nanotube.

12. The biological electrode composition according to claim 8, wherein the carbon material is any one or both of a carbon black and a carbon nanotube.

13. The biological electrode composition according to claim 9, wherein the carbon material is any one or both of a carbon black and a carbon nanotube.

14. The biological electrode composition according to claim 10, wherein the carbon material is any one or both of a carbon black and a carbon nanotube.

15. A biological electrode, which is a biological electrode having a conductive substrate and a living body contact layer formed on the conductive substrate, wherein the living body contact layer is a cured product of the biological electrode composition according to any one of claim 3.

16. A biological electrode, which is a biological electrode having a conductive substrate and a living body contact layer formed on the conductive substrate, wherein the living body contact layer is a cured product of the biological electrode composition according to any one of claim 4.

17. The biological electrode according to claim 15, wherein the conductive substrate contains one or more substances selected from gold, silver, silver chloride, platinum, aluminum, magnesium, tin, tungsten, iron, copper, nickel, stainless steel, chromium, titanium, and carbon.

18. The biological electrode according to claim 16, wherein the conductive substrate contains one or more substances selected from gold, silver, silver chloride, platinum, aluminum, magnesium, tin, tungsten, iron, copper, nickel, stainless steel, chromium, titanium, and carbon.

19. A method for producing a biological electrode, which is a method for producing a biological electrode having a conductive substrate and a living body contact layer formed on the conductive substrate, wherein the method comprises application of the biological electrode composition according to any one of claim 3 on the conductive substrate followed by curing the composition to form the living body contact layer.

20. The method for producing the biological electrode according to claim 19, wherein the conductive substrate containing one or more substances selected from gold, silver, silver chloride, platinum, aluminum, magnesium, tin, tungsten, iron, copper, nickel, stainless steel, chromium, titanium, and carbon is used.

* * * * *